(12) United States Patent
Brown et al.

(10) Patent No.: US 10,760,114 B2
(45) Date of Patent: Sep. 1, 2020

(54) METHODS FOR DELIVERING AN ANALYTE TO TRANSMEMBRANE PORES

(71) Applicant: Oxford Nanopore Technologies Ltd., Oxford (GB)

(72) Inventors: Clive Gavin Brown, Oxford (GB); Daniel Ryan Garalde, Oxford (GB); Andrew John Heron, Oxford (GB); Daniel John Turner, Oxford (GB); James White, Oxford (GB)

(73) Assignee: Oxford Nanopore Technologies Ltd., Oxford (GB)

( * ) Notice: Subject to any disclaimer, the term of this patent is extended or adjusted under 35 U.S.C. 154(b) by 434 days.

(21) Appl. No.: 15/519,606

(22) PCT Filed: Oct. 6, 2015

(86) PCT No.: PCT/GB2015/052919
§ 371 (c)(1),
(2) Date: Apr. 17, 2017

(87) PCT Pub. No.: WO2016/059375
PCT Pub. Date: Apr. 21, 2016

(65) Prior Publication Data
US 2017/0253910 A1 Sep. 7, 2017

(30) Foreign Application Priority Data

Oct. 17, 2014 (GB) .................................. 1418469.1

(51) Int. Cl.
*C12Q 1/6804* (2018.01)
*C12Q 1/6869* (2018.01)
(Continued)

(52) U.S. Cl.
CPC ............. *C12Q 1/6804* (2013.01); *C12N 9/52* (2013.01); *C12N 15/1013* (2013.01);
(Continued)

(58) Field of Classification Search
CPC .............. C12Q 1/6804; G01N 33/6872; C12N 15/1013
See application file for complete search history.

(56) References Cited

U.S. PATENT DOCUMENTS 5,576,204 A 11/1996 Blanco et al.
5,712,126 A 1/1998 Weissman et al.
(Continued)

FOREIGN PATENT DOCUMENTS

| AU | 2006/336262 B2 | 7/2007 |
| CN | 102317310 A | 1/2012 |

(Continued)

OTHER PUBLICATIONS

Peng et al, Reverse DNA translocation through a solid-state nanopore by magnetic tweezers, 2009, 20, 185101 (8pp) (Year: 2009).*
(Continued)

*Primary Examiner* — Narayan K Bhat
(74) *Attorney, Agent, or Firm* — Wolf, Greenfield & Sacks, P.C.

(57) ABSTRACT

The invention relates to a new method of delivering an analyte to a transmembrane pore in a membrane. The method involves the use of microparticles.

25 Claims, 15 Drawing Sheets

Specification includes a Sequence Listing.

(51) Int. Cl.
*C12N 9/52* (2006.01)
*C12N 15/10* (2006.01)
*G01N 33/487* (2006.01)
*G01N 33/68* (2006.01)

(52) U.S. Cl.
CPC ..... *C12Q 1/6869* (2013.01); *G01N 33/48721* (2013.01); *G01N 33/48728* (2013.01); *G01N 33/6872* (2013.01); *B03C 2201/18* (2013.01); *C12Q 2523/303* (2013.01); *C12Q 2525/197* (2013.01); *C12Q 2563/149* (2013.01); *C12Q 2563/155* (2013.01); *C12Q 2565/631* (2013.01)

(56) References Cited

U.S. PATENT DOCUMENTS

| | | | |
|---|---|---|---|
| 8,431,337 B2 * | 4/2013 | Kim | B82Y 30/00 204/403.06 |
| 8,828,208 B2 | 9/2014 | Canas et al. | |
| 9,057,102 B2 | 6/2015 | Turner et al. | |
| 9,222,082 B2 | 12/2015 | Jayasinghe et al. | |
| 9,447,152 B2 | 9/2016 | Clarke et al. | |
| 9,546,400 B2 | 1/2017 | Turner et al. | |
| 9,556,480 B2 | 1/2017 | Turner et al. | |
| 9,678,056 B2 | 6/2017 | Turner et al. | |
| 9,738,929 B2 | 8/2017 | Turner et al. | |
| 10,246,741 B2 | 4/2019 | Clarke et al. | |
| 10,337,060 B2 | 7/2019 | Crawford et al. | |
| 2002/0192769 A1 | 12/2002 | Park et al. | |
| 2010/0331194 A1 | 12/2010 | Turner et al. | |
| 2011/0229877 A1 | 9/2011 | Jayasinghe et al. | |
| 2012/0100530 A1 | 4/2012 | Moysey et al. | |
| 2013/0146456 A1 | 6/2013 | Gundlach et al. | |
| 2014/0134618 A1 * | 5/2014 | Kokoris | C12Q 1/6806 435/6.11 |
| 2014/0186823 A1 | 7/2014 | Clarke et al. | |
| 2014/0235462 A1 | 8/2014 | Kosteroglou et al. | |
| 2014/0262784 A1 | 9/2014 | Clarke et al. | |
| 2017/0022557 A1 | 1/2017 | Clarke et al. | |
| 2017/0204457 A1 | 7/2017 | Crawford et al. | |
| 2019/0241949 A1 | 8/2019 | Clarke et al. | |
| 2019/0382834 A1 | 12/2019 | Clarke et al. | |

FOREIGN PATENT DOCUMENTS

| | | |
|---|---|---|
| EP | 2682460 A1 | 1/2014 |
| JP | 2009-519705 A1 | 5/2009 |
| JP | 2012-516146 A | 7/2012 |
| JP | 2014-519823 A | 8/2014 |
| WO | WO 2000/028312 A1 | 5/2000 |
| WO | WO 2000/078668 A1 | 12/2000 |
| WO | WO 2000/079257 A1 | 12/2000 |
| WO | WO 2005/124888 A1 | 12/2005 |
| WO | WO 2006/100484 A2 | 9/2006 |
| WO | WO 2007/057668 A1 | 5/2007 |
| WO | WO 2008/092760 A1 | 8/2008 |
| WO | WO 2008/102120 A1 | 8/2008 |
| WO | WO 2008/102121 A1 | 8/2008 |
| WO | WO 2008/124107 A1 | 10/2008 |
| WO | WO 2009/020682 A2 | 2/2009 |
| WO | WO 2009/035647 A1 | 3/2009 |
| WO | WO 2009/077734 A2 | 6/2009 |
| WO | WO 2009/132124 A2 | 10/2009 |
| WO | WO 2009/151788 A2 | 12/2009 |
| WO | WO 2010/004265 A1 | 1/2010 |
| WO | WO 2010/004273 A1 | 1/2010 |
| WO | WO 2010/034018 * | 3/2010 |
| WO | WO 2010/086602 A1 | 8/2010 |
| WO | WO 2010/086603 A1 | 8/2010 |
| WO | WO 2010/086622 A2 | 8/2010 |
| WO | WO 2010/122293 A1 | 10/2010 |
| WO | WO 2011/067559 A1 | 6/2011 |
| WO | WO 2012/033524 A2 | 3/2012 |
| WO | WO 2012/107778 A2 | 8/2012 |
| WO | WO 2012/164270 A1 | 12/2012 |
| WO | WO 2013/014451 A1 | 1/2013 |
| WO | WO 2013/041878 A1 | 3/2013 |
| WO | WO 2013/057495 A2 | 4/2013 |
| WO | WO 2013/098561 A1 | 7/2013 |
| WO | WO 2013/098562 A2 | 7/2013 |
| WO | WO 2013/119784 A1 | 8/2013 |
| WO | WO 2013/153359 A1 | 10/2013 |
| WO | WO 2014/013259 A1 | 1/2014 |
| WO | WO 2014/013260 A1 | 1/2014 |
| WO | WO 2014/013262 A1 | 1/2014 |
| WO | WO 2014/064443 A2 | 5/2014 |
| WO | WO 2014/064444 A1 | 5/2014 |
| WO | WO 2014/135838 A1 | 9/2014 |
| WO | WO 2015/022544 A1 | 2/2015 |
| WO | WO 2015/055981 A2 | 4/2015 |
| WO | WO 2015/061509 A1 | 4/2015 |
| WO | WO 2015/110777 A1 | 7/2015 |
| WO | WO 2015/124935 A1 | 8/2015 |
| WO | WO 2015/150786 A1 | 10/2015 |
| WO | WO 2015/150787 A1 | 10/2015 |

OTHER PUBLICATIONS

[No Author Listed] Lambda Exonuclease product. 2017. Last accessed at https://www.neb.com/products/m0262-lambda-exonuclease on Feb. 8, 2017.

Albrecht, Nanobiotechnology: A new look for nanopore sensing. Nat Nanotechnol. Apr. 2011;6(4):195-6. doi: 10.1038/nnano.2011.52.

Ali et al., Sequence-specific recognition of DNA oligomer using peptide nucleic acid (PNA)-modified synthetic ion channels: PNA/DNA hybridization in nanoconfined environment. ACS Nano. Dec. 28, 2010;4(12):7267-74. doi: 10.1021/nn102119q. Epub Nov. 17, 2010.

Andersson et al., Detection of single ion channel activity on a chip using tethered bilayer membranes. Langmuir. Mar. 13, 2007;23(6):2924-7. Epub Feb. 8, 2007.

Astier et al., Toward single molecule DNA sequencing: direct identification of ribonucleoside and deoxyribonucleoside 5'-monophosphates by using an engineered protein nanopore equipped with a molecular adapter. J Am Chem Soc. Feb. 8, 2006;128(5):1705-10.

Case 1:17-cv-00275-LPS Document 18. Notice of subsequent events relating to Oxford's motion to dismiss (D.I. 9). Oct. 18, 2017.

Case 1:17-cv-00275-LPS Document 19. Oxford Nanopore Technologies, Inc.'s response to Pacific Biosciences of California, Inc.'s notice of subsequent events. Oct. 24, 2017.

Case 1:17-cv-00275-RGA Document 10. Oxford's opening brief in support of its motion to dismiss PacBio's complaint for patent infringement. May 8, 2017.

Case 1:17-cv-00275-RGA Document 14. PacBio's response to Oxford's motion to dismiss. Jun. 5, 2017.

Case 1:17-cv-00275-RGA Document 16. Oxford's reply brief in support of its motion to dismiss PacBio's complaint for patent infringement. Jun. 26, 2017.

Case 1:17-cv-01353-LPS Document 13. First Amended Complaint for Patent Infringement. Nov. 30, 2017.

Case 1:17-cv-01353-LPS Document 15. Plaintiff's response to Oxford Nanopore Technologies, Inc.'s Motion to Dismiss and Request for Scheduling Conference. Nov. 30, 2017.

Case 1:17-cv-01353-RGA Document 10. Oxford's opening brief in support of its motion to partially dismiss Pacbio's complaint for patent infringement. Nov. 16, 2017.

Chandler et al., Membrane surface dynamics of DNA-threaded nanopores revealed by simultaneous single-molecule optical and ensemble electrical recording. Langmuir. Feb. 3, 2004;20(3):898-905

Clarke et al., Continuous base identification for single-molecule nanopore DNA sequencing. Nat Nanotechnol. Apr. 2009;4(4):265-70. doi: 10.1038/nnano.2009.12. Epub Feb. 22, 2009.

(56) References Cited

OTHER PUBLICATIONS

Cockroft et al., A single-molecule nanopore device detects DNA polymerase activity with single-nucleotide resolution. J Am Chem Soc. Jan. 23, 2008;130(3):818-20. doi: 10.1021/ja077082c. Epub Jan. 1, 2008.

Dekker, Solid-state nanopores. Nat Nanotechnol. Apr. 2007;2(4):209-15. doi:10.1038/nnano.2007.27. Epub Mar. 4, 2007.

Feng et al., Nanopore-based fourth-generation DNA sequencing technology. Genomics Proteomics Bioinformatics. Feb. 2015;13(1):4-16. doi: 10.1016/j.gpb.2015.01.009. Epub Mar. 2, 2015. Review. Erratum in: Genomics Proteomics Bioinformatics. Dec. 2015;13(6):383. Genomics Proteomics Bioinformatics. Jun. 2015;13(3):200-201.

Gu et al., Interaction of the noncovalent molecular adapter, beta-cyclodextrin, with the staphylococcal alpha-hemolysin pore. Biophys J. Oct. 2000;79(4):1967-75.

Holden et al., Direct introduction of single protein channels and pores into lipid bilayers. J Am Chem Soc. May 11, 2005;127(18):6502-3.

Howorka et al., Nanopore analytics: sensing of single molecules. Chem Soc Rev. Aug. 2009;38(8):2360-84. doi: 10.1039/b813796j. Epub Jun. 15, 2009.

Howorka et al., Sequence-specific detection of individual DNA strands using engineered nanopores. Nat Biotechnol. Jul. 2001;19(7):636-9.

Ivanov et al., DNA tunneling detector embedded in a nanopore. Nano Lett. Jan. 12, 2011;11(1):279-85. doi: 10.1021/nl103873a. Epub Dec. 6, 2010.

Kasianowicz et al., Characterization of individual polynucleotide molecules using a membrane channel. Proc Natl Acad Sci U S A. Nov. 26, 1996;93(24):13770-3.

Keyser, Controlling molecular transport through nanopores. J R Soc Interface. Oct. 7, 2011;8(63):1369-78. doi: 10.1098/rsif.2011.0222.

Langecker et al., Synthetic lipid membrane channels formed by designed DNA nanostructures. Science. Nov. 16, 2012;338(6109):932-6. doi: 10.1126/science.1225624.

Lieberman et al., Processive replication of single DNA molecules in a nanopore catalyzed by phi29 DNA polymerase. J Am Chem Soc. Dec. 22, 2010;132(50):17961-72. doi:10.1021/ja1087612. Epub Dec. 1, 2010.

Nikolov et al., Behavior of giant vesicles with anchored DNA molecules. Biophys J. Jun. 15, 2007;92(12):4356-68. Epub Mar. 23, 2007.

Pfeiffer et al., Bivalent cholesterol-based coupling of oligonucletides to lipid membrane assemblies. J Am Chem Soc. Aug. 25, 2004;126(33):10224-5.

Stoddart et al., Single-nucleotide discrimination in immobilized DNA oligonucleotides with a biological nanopore. Proc Natl Acad Sci U S A. May 12, 2009;106(19):7702-7. doi: 10.1073/pnas. 0901054106. Epub Apr. 20, 2009.

United States District Court for the District of Delaware Order. *Pacific Biosciences of California, Inc.* v. *Oxford Nanopore Technolgoies, Inc.* Civil Action No. 17-275-RGA. Nov. 9, 2017.

Van Lengerich et al., Covalent attachment of lipid vesicles to a fluid-supported bilayer allows observation of DNA-mediated vesicle interactions. Langmuir. Jun. 1, 2010;26(11):8666-72. doi: 10.1021/la904822f.

Wanunu et al., DNA translocation governed by interactions with solid-state nanopores. Biophys J. Nov. 15, 2008;95(10):4716-25. doi: 10.1529/biophysj.108.140475. Epub Aug. 15, 2008.

Wilson et al., Electronic control of DNA polymerase binding and unbinding to single DNA molecules. ACS Nano. Apr. 28, 2009;3(4):995-1003. doi: 10.1021/nn9000897.

Yoshina-Ishii et al., Arrays of mobile tethered vesicles on supported lipid bilayers. J Am Chem Soc. Apr. 2, 2003;125(13):3696-7.

Heredia et al., In vitro double transposition for DNA identification. Anal Biochem. Apr. 1, 2010;399(1):78-83. doi:10.1016/j.ab.2009. 11.030. Epub Nov. 26, 2009.

Ohvo et al., Cyclodextrin-mediated removal of sterols from monolayers:effects of sterol structure and phospholipids on desorption rate. Biochemistry. Jun. 18, 1996;35(24):8018-24.

\* cited by examiner (A)

(B)

ered an analyte to a transmembrane pore in a membrane, comprising (a) providing the analyte attached to a microparticle and (b) delivering the microparticle towards the membrane and thereby delivering the analyte to the transmembrane pore.

METHODS FOR DELIVERING AN ANALYTE TO TRANSMEMBRANE PORES

This Application is a national stage filing under 35 U.S.C. § 371 of PCT International Application No. PCT/GB2015/052919, which has an international filing date of Oct. 6, 2015, and claims foreign priority benefits under 35 U.S.C. § 119(a)-(d) or 35 U.S.C. § 365(b) of British application number 1418469.1, filed Oct. 17, 2014. The contents of the aforementioned applications are herein incorporated by reference in their entireties.

FIELD OF THE INVENTION

The invention relates to a new method of delivering an analyte to a transmembrane pore in a membrane. The method involves the use of microparticles.

BACKGROUND OF THE INVENTION

There is currently a need for rapid and cheap polynucleotide (e.g. DNA or RNA) sequencing and identification technologies across a wide range of applications. Existing technologies are slow and expensive mainly because they rely on amplification techniques to produce large volumes of polynucleotide and require a high quantity of specialist fluorescent chemicals for signal detection.

Transmembrane pores (nanopores) have great potential as direct, electrical biosensors for polymers and a variety of small molecules. In particular, recent focus has been given to nanopores as a potential DNA sequencing technology.

When a potential is applied across a nanopore, there is a change in the current flow when an analyte, such as a nucleotide, resides transiently in the barrel for a certain period of time. Nanopore detection of the nucleotide gives a current change of known signature and duration. In the strand sequencing method, a single polynucleotide strand is passed through the pore and the identities of the nucleotides are derived. Strand sequencing can involve the use of a polynucleotide binding protein to control the movement of the polynucleotide through the pore.

It has previously been demonstrated that ultra low concentration analyte delivery can be achieved by coupling the analyte to a membrane in which the relevant detector is present. This lowers by several orders of magnitude the amount of analyte required in order to be detected (WO 2012/164270).

SUMMARY OF THE INVENTION

The inventors have surprisingly demonstrated that it is possible to increase the efficiency of delivery of an analyte to a transmembrane pore in a membrane using a microparticle. The microparticle lowers by several orders of magnitude the amount of analyte required in order to be detected using the transmembrane pore.

Accordingly, the invention provides a method for delivering an analyte to a transmembrane pore in a membrane, comprising (a) providing the analyte attached to a microparticle and (b) delivering the microparticle towards the membrane and thereby delivering the analyte to the transmembrane pore.

The invention also provides:

a method for characterising a polynucleotide analyte, comprising (a) carrying out the method of the invention on a polynucleotide analyte; (b) allowing the polynucleotide to interact with the transmembrane pore such that the polynucleotide moves through the pore; and (c) taking one or more measurements as the polynucleotide moves with respect to the pore, wherein the measurements are indicative of one or more characteristics of the polynucleotide, and thereby characterising the polynucleotide;

a method for determining the presence, absence or one or more characteristics of an analyte using a transmembrane pore, comprising (a) carrying out the method of the invention; (b) allowing the analyte to interact with the transmembrane pore; and (c) taking one or more measurements during the interaction, wherein the measurements are indicative of the presence, absence or one or more characteristics of the analyte; and a kit for delivering an analyte to a transmembrane pore in a membrane, comprising (a) a microparticle and (b) one or more anchors which are capable of coupling the analyte to the membrane.

DESCRIPTION OF THE SEQUENCE LISTING

Figure 1:
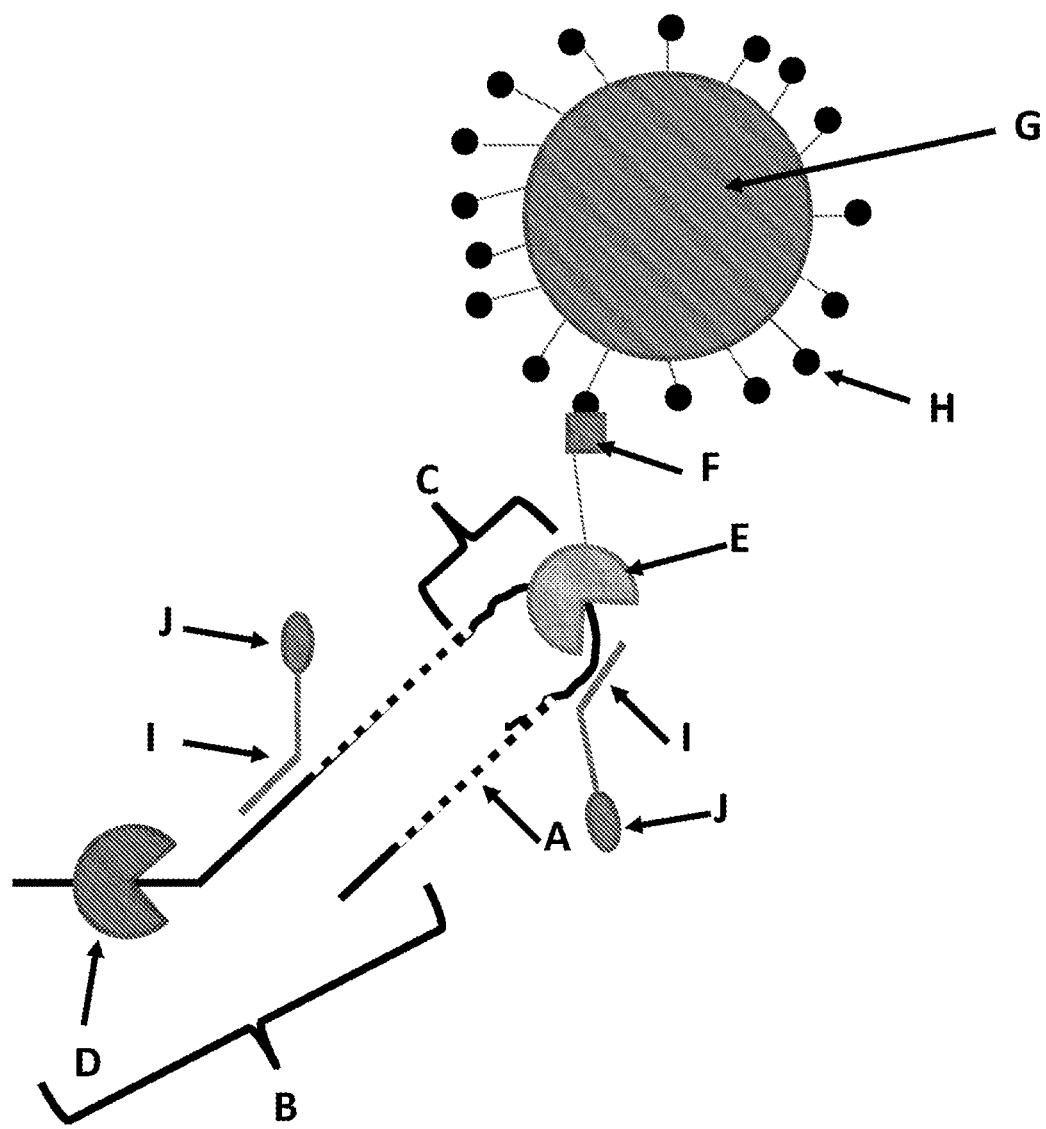
FIG. 1 shows a cartoon representation (not to scale) of how the DNA was attached to the Dynabead® in Example 1. The double-stranded DNA (dsDNA) sample was obtained by the fragmentation of lambda DNA, (shown as a dotted line and labelled A) and has a Y-adapter (labelled B) and a hairpin adapter (labelled C) attached to either end of the lambda DNA. Two different helicases are bound to the dsDNA sample. The helicase that binds to the Y-adapter (labelled D) did not have a his-tag (6 consecutive histidines) present in its amino acid sequence, whereas the helicase (labelled E) that binds to the hairpin did have a his-tag (6 consecutive histidines; shown in the figure as a grey square and labelled F) present in its amino acid sequence. When the His-Tag Isolation and Pulldown Dynabead® (labelled G) is pre-incubated with the dsDNA sample, the cobalt on the surface of the bead (shown as a black circles and labelled H) then binds to the histidines on the enzyme. The dsDNA sample also has two anchors (labelled J) which were attached to DNA strands that were (labelled I) hybridised to the sample, these are used to associate the DNA with the membrane. This figure shows the attachment of a single dsDNA sample however the bead is covered in cobalt so it is likely to bind multiple dsDNA samples on a single bead.

SEQ ID NO: 1 shows the codon optimised polynucleotide sequence encoding the MS-B1 mutant MspA monomer. This mutant lacks the signal sequence and includes the following mutations: D90N, D91N, D93N, D118R, D134R and E139K.

SEQ ID NO: 2 shows the amino acid sequence of the mature form of the MS-B1 mutant of the MspA monomer. This mutant lacks the signal sequence and includes the following mutations: D90N, D91N, D93N, D118R, D134R and E139K.

SEQ ID NO: 3 shows the polynucleotide sequence encoding one monomer of α-hemolysin-E111N/K147N (α-HL-NN; Stoddart et al., PNAS, 2009; 106(19): 7702-7707).

SEQ ID NO: 4 shows the amino acid sequence of one monomer of α-HL-NN.

SEQ ID NOs: 5 to 7 show the amino acid sequences of MspB, C and D.

SEQ ID NO: 8 shows the polynucleotide sequence encoding the Phi29 DNA polymerase.

SEQ ID NO: 9 shows the amino acid sequence of the Phi29 DNA polymerase.

SEQ ID NO: 10 shows the codon optimised polynucleotide sequence derived from the sbcB gene from E. coli. It encodes the exonuclease I enzyme (EcoExo I) from E. coli.

SEQ ID NO: 11 shows the amino acid sequence of exonuclease I enzyme (EcoExo I) from *E. coli*.

SEQ ID NO: 12 shows the codon optimised polynucleotide sequence derived from the xthA gene from *E. coli*. It encodes the exonuclease III enzyme from *E. coli*.

SEQ ID NO: 13 shows the amino acid sequence of the exonuclease III enzyme from *E. coli*. This enzyme performs distributive digestion of 5' monophosphate nucleosides from one strand of double stranded DNA (dsDNA) in a 3'-5' direction. Enzyme initiation on a strand requires a 5' overhang of approximately 4 nucleotides.

SEQ ID NO: 14 shows the codon optimised polynucleotide sequence derived from the recJ gene from *T. thermophilus*. It encodes the RecJ enzyme from *T. thermophilus* (TthRecJ-cd).

SEQ ID NO: 15 shows the amino acid sequence of the RecJ enzyme from *T. thermophilus* (TthRecJ-cd). This enzyme performs processive digestion of 5' monophosphate nucleosides from ssDNA in a 5'-3' direction. Enzyme initiation on a strand requires at least 4 nucleotides.

SEQ ID NO: 16 shows the codon optimised polynucleotide sequence derived from the bacteriophage lambda exo (redX) gene. It encodes the bacteriophage lambda exonuclease.

SEQ ID NO: 17 shows the amino acid sequence of the bacteriophage lambda exonuclease. The sequence is one of three identical subunits that assemble into a trimer. The enzyme performs highly processive digestion of nucleotides from one strand of dsDNA, in a 5'-3' direction (http://www.neb.com/nebecomm/products/productM0262.asp). Enzyme initiation on a strand preferentially requires a 5' overhang of approximately 4 nucleotides with a 5' phosphate.

SEQ ID NO: 18 shows the amino acid sequence of Hel308 Mbu.

SEQ ID NO: 19 shows the amino acid sequence of Hel308 Csy.

SEQ ID NO: 20 shows the amino acid sequence of Hel308 Tga.

SEQ ID NO: 21 shows the amino acid sequence of Hel308 Mhu.

SEQ ID NO: 22 shows the amino acid sequence of TraI Eco.

SEQ ID NO: 23 shows the amino acid sequence of XPD Mbu.

SEQ ID NO: 24 shows the amino acid sequence of Dda 1993.

SEQ ID NO: 25 shows the amino acid sequence of Trwc Cba.

DETAILED DESCRIPTION OF THE INVENTION

It is to be understood that different applications of the disclosed products and methods may be tailored to the specific needs in the art. It is also to be understood that the terminology used herein is for the purpose of describing particular embodiments of the invention only, and is not intended to be limiting.

In addition as used in this specification and the appended claims, the singular forms "a", "an", and "the" include plural referents unless the content clearly dictates otherwise. Thus, for example, reference to "an analyte" includes two or more analytes, reference to "a microparticle" includes two or more microparticles, reference to "a polynucleotide" includes two or more polynucleotides, reference to "an anchor" refers to two or more anchors, reference to "a helicase" includes two or more helicases, reference to "a transmembrane pore" includes two or more pores and the like.

All publications, patents and patent applications cited herein, whether supra or infra, are hereby incorporated by reference in their entirety.

Method of the Invention

The invention provides a method for delivering an analyte to a transmembrane pore in a membrane. The method comprises providing the analyte attached to a microparticle. The method may comprise attaching the analyte to the microparticle. The microparticle is then delivered towards the membrane and this delivers the analyte to the transmembrane pore.

The inventors have surprisingly demonstrated that ultra low concentration analyte delivery to the pore can be achieved by attaching the analyte to a microparticle. This lowers by several orders of magnitude the amount of analyte required in order to be detected. The extent to which the amount of analyte needed is reduced could not have been predicted. In particular, the inventors surprisingly report an increase in the capture of single stranded polynucleotide by at least 10 orders of magnitude over that previously reported. This has dramatic implications on the sample preparation requirements that are of key concern for diagnostic devices such as next-generation sequencing systems.

The method of the invention is preferably for delivering an increased concentration of the analyte to the transmembrane pore in the membrane. The method of the invention is preferably an improved method of characterising an analyte using a transmembrane pore in a membrane by delivering an increased concentration of the analyte to the transmembrane pore. The concentration of the analyte delivered to the transmembrane pore is preferably increased by at least about 1000 fold, at least about 10000 fold, at least about 100000 fold, at least about 1000000 fold at least about 10000000 fold, at least about 100000000 relative to analytes which have not been coupled to the membrane.

The delivery efficiency using microparticles is particularly increased when the analyte is also coupled to the membrane. Coupling the analyte to a membrane has added advantages for various nanopore-enzyme sequencing applications. In strand sequencing, when the polynucleotide analyte is introduced the pore may become blocked permanently or temporarily, preventing the sequencing of the polynucleotide. When one end of the polynucleotide analyte is localised away from the pore, for example by coupling or tethering to the membrane, surprisingly it was found that this temporary or permanent blocking is no longer observed. By occupying one end of the polynucleotide by coupling it to the membrane it also acts to effectively increase the analyte concentration over the pore and so increase the sequencing systems duty cycle. The concentration of the analyte delivered to the transmembrane pore is preferably increased by at least about 5, 6, 7, 8, 9, 10, 11, 12, 13, 14, 15, 16, 17, 18, 19 fold, at least about 20 fold, at least about 25 fold, at least about 30 fold, at least about 35 fold, at least about 40 fold, at least about 45 fold, at least about 50 fold or at least about 100 fold relative to analytes which have been coupled to the membrane.

The method of the invention is preferably for delivering an increased concentration of the polynucleotide to the transmembrane pore in the membrane for characterisation or sequencing. The method of the invention is preferably an improved method of characterising or sequencing a polynucleotide using a transmembrane pore in a membrane by delivering an increased concentration of the analyte to the transmembrane pore. The concentration of the polynucleotide delivered to the transmembrane pore is preferably increased by any of the amounts discussed above. The method is of course advantageous for detecting an analyte that is present at low concentrations. The method preferably allows the analyte to be delivered to the transmembrane pore (and optionally the presence or one or more characteristics of the analyte to be determined) when the analyte is present at a concentration of from about 0.001 pM to about 1 nM, such as less than about 0.01 pM, less than about 0.1 pM, less than about 1 pM, less than about 10 pM or less than about 100 pM. The method is of course advantageous for detecting an analyte that is present at low concentrations. The method preferably allows the presence or one or more characteristics of the analyte to be determined when the analyte is present at a concentration of from about 0.001 pM to about 1 nM, such as less than about 0.01 pM, less than about 0.1 pM, less than about 1 pM, less than about 10 pM or less than about 100 pM.

The method preferably allows the analyte to be delivered to the transmembrane pore (and optionally the presence or one or more characteristics of the analyte to be determined) when about 10 ng or less, such as about 5 ng or less, about 2.5 ng or less, about 1.0 ng or less, about 0.5 ng or less, about 0.1 ng or less, about 0.01 ng or less or about 0.001 ng or less, of the analyte is present. The method preferably allows the analyte to be delivered to the transmembrane pore (and optionally the presence or one or more characteristics of the analyte to be determined) when about 5.0 femtomole (fmol) or less, such as about 4.0 fmol or less, about 3.0 fmol or less, about 2.0 fmol or less, about 1.0 fmol or less, about 0.5 fmol or less, about 0.1 fmol or less, about 0.01 fmol or less or about 0.001 fmol or less, of the analyte is present.

The method of the invention is particularly advantageous for polynucleotide sequencing because only small amounts of purified polynucleotide can be obtained from human blood. The method preferably allows delivery of a polynucleotide to a transmembrane pore (and optionally estimating the sequence of, or allows sequencing of, the polynucleotide) that is present at a concentration of from about 0.001 pM to about 1 nM, such as less than 0.01 pM, less than 0.1 pM, less than 1 pM, less than 10 pM or less than 100 pM.

The method preferably allows the polynucleotide to be delivered to the transmembrane pore (and optionally estimating the sequence of, or allows sequencing of, the polynucleotide) when 10 ng or less, such as about 5 ng or less, about 2.5 ng or less, about 1.0 ng or less, about 0.5 ng or less, about 0.1 ng or less, about 0.01 ng or less or about 0.001 ng or less, of the polynucleotide is present. The method preferably allows the polynucleotide to be delivered to the transmembrane pore (and optionally estimating the sequence of, or allows sequencing of, the polynucleotide) when about 5.0 femtomole (fmol) or less, such as about 4.0 fmol or less, about 3.0 fmol or less, about 2.0 fmol or less, about 1.0 fmol or less, about 0.5 fmol or less, about 0.1 fmol or less, about 0.01 fmol or less or about 0.001 fmol or less, of the polynucleotide is present.

The method of the invention preferably allows the delivery to the transmembrane pore of (and optionally the characterisation of) a single molecule of the analyte or polynucleotide.

As discussed in more detail below, two or more versions of the same or similar analytes can be characterised using the invention. This is advantageous in polynucleotide sequencing because it allows the sequence of a polynucleotide to be investigated more than once. This leads to increased sequencing efficiency and accuracy.

Coupling one end of a polynucleotide to the membrane (even temporarily) also means that the end will be prevented from interfering with the nanopore-based sequencing process.

The method of the invention also has other advantages. The microparticle used in the invention can be designed to select or capture the target analyte from a sample containing other analytes and deliver the analyte to the transmembrane pore. This is discussed in more detail below.

The sample preparation for nanopore characterisation or sequencing typically involves purifying the analyte, such as the polynucleotide, using microparticles. The microparticles are then removed prior to characterisation or sequencing. If the microparticles are used to deliver the analyte or polynucleotide to the transmembrane pore, the sample preparation method involves one fewer step and so is quicker and easier to perform.

Analyte

The method of the invention concerns delivering an analyte to a transmembrane pore in a membrane. Any number of analytes can be delivered. For instance, the method of the invention may concern delivering two or more analytes, such as 3 or more, 4 or more, 5 or more, 6 or more, 7 or more, 8 or more, 9 or more, 10 or more, 20 or more, 30 or more, 50 or more, 100 or more, 500 or more, 1,000 or more, 5,000 or more, 10,000 or more, 100,000 or more, 1000,000 or more or 5000,000 or more, analytes. The two or more analytes may be delivered using the same microparticle or different microparticles.

If two or more analytes are delivered, they may be different from one another. For instance, the first analyte may be a protein and the second analyte may be a polynucleotide. Alternatively, the two or more analytes may be different polynucleotides. The two or more analytes may be the product of random fragmentation of multiple copies of a longer polynucleotide sequence (such as multiple copies of a genome) and so may be different, but overlapping polynucleotide fragments. The two or more analytes may be two or more instances of the same analyte. The two or more analytes may be identical. This allows proof reading, particularly if the analytes are polynucleotides. If the method concerns investigating three or more analytes, they may all be three or more instances of the same analyte or some of them may be separate instances of the same analyte.

The method of the invention may concern determining or measuring one or more characteristics of the analyte. The method may involve determining or measuring two, three, four or five or more characteristics of the analyte. The one or more characteristics are preferably selected from (i) the size of the analyte, (ii) the identity of the analyte, (iii) the secondary structure of the analyte and (iv) whether or not the analyte is modified. Any combination of (i) to (iv) may be measured in accordance with the invention, such as {i}, {ii}, {iii}, {iv}, {i,ii}, {i,iii}, {i,iv}, {ii,iii}, {ii,iv}, {iii,iv}, {i,ii,iv}, {i,iii,iv}, {ii,iii,iv} or {i,ii,iii,iv}. The method of the invention preferably comprises estimating the sequence of or sequencing a polynucleotide. This is discussed in more detail below.

The analyte can be any substance. Suitable analytes include, but are not limited to, metal ions, inorganic salts, polymers, such as a polymeric acids or bases, dyes, bleaches, pharmaceuticals, diagnostic agents, recreational drugs, explosives and environmental pollutants.

The analyte can be an analyte that is secreted from cells. Alternatively, the analyte can be an analyte that is present inside cells such that the analyte must be extracted from the cells before the invention can be carried out.

The analyte is preferably an amino acid, peptide, polypeptide, a protein or a polynucleotide. The amino acid, peptide, polypeptide or protein can be naturally-occurring or non-naturally-occurring. The polypeptide or protein can include within it synthetic or modified amino acids. A number of different types of modification to amino acids are known in the art. For the purposes of the invention, it is to be understood that the analyte can be modified by any method available in the art.

The protein can be an enzyme, antibody, hormone, growth factor or growth regulatory protein, such as a cytokine. The cytokine may be selected from an interleukin, preferably IFN-1, IL-2, IL-4, IL-5, IL-6, IL-10, IL-12 or IL-13, an interferon, preferably IL-γ or other cytokines such as TNF-α. The protein may be a bacterial protein, fungal protein, virus protein or parasite-derived protein. Before it is contacted with the pore, the protein may be unfolded to form a polypeptide chain.

The analyte is most preferably a polynucleotide, such as a nucleic acid. Polynucleotides are discussed in more detail below. A polynucleotide may be coupled to the membrane at its 5' end or 3' end or at one or more intermediate points along the strand. The polynucleotide can be single stranded or double stranded as discussed below. The polynucleotide may be circular. The polynucleotide may be an aptamer, a probe which hybridises to microRNA or microRNA itself (Wang, Y. et al, Nature Nanotechnology, 2011, 6, 668-674). The analyte may be a polynucleotide which binds to a protein and may be used to characterise the protein, for instance to determine their concentration.

When the analyte is a probe which hybridises to microRNA, the probe may be coupled permanently or transiently to the membrane. This is discussed in more detail below. The probe itself may be adapted to couple directly to the membrane or may hybridise to a complementary polynucleotide which has been adapted to couple to the membrane. The analyte may be a complex of microRNA hybridised to a probe where the probe has distinctive sequences or barcodes enabling it to be identified unambiguously.

When the analyte is an aptamer, the aptamer may be coupled permanently or transiently to the membrane. The aptamer itself may be adapted to couple directly to the membrane or may hybridise to a complementary polynucleotide which has been adapted to couple to the membrane. The aptamer may be bound or unbound to a protein analyte and the ultimate purpose of detecting the aptamer may be to detect the presence, absence or one or more characteristics of a protein analyte to which it binds.

Polynucleotide

The analyte is preferably a polynucleotide. A polynucleotide, such as a nucleic acid, is a macromolecule comprising two or more nucleotides. The polynucleotide or nucleic acid may comprise any combination of any nucleotides. The nucleotides can be naturally occurring or artificial. One or more nucleotides in the polynucleotide can be oxidized or methylated. One or more nucleotides in the polynucleotide may be damaged. For instance, the polynucleotide may comprise a pyrimidine dimer. Such dimers are typically associated with damage by ultraviolet light and are the primary cause of skin melanomas. One or more nucleotides in the polynucleotide may be modified, for instance with a label or a tag. Suitable labels are described below. The polynucleotide may comprise one or more spacers.

A nucleotide typically contains a nucleobase, a sugar and at least one phosphate group. The nucleobase and sugar form a nucleoside.

The nucleobase is typically heterocyclic. Nucleobases include, but are not limited to, purines and pyrimidines and more specifically adenine (A), guanine (G), thymine (T), uracil (U) and cytosine (C).

The sugar is typically a pentose sugar. Nucleotide sugars include, but are not limited to, ribose and deoxyribose. The sugar is preferably a deoxyribose.

The polynucleotide preferably comprises the following nucleosides: deoxyadenosine (dA), deoxyuridine (dU) and/or thymidine (dT), deoxyguanosine (dG) and deoxycytidine (dC).

The nucleotide is typically a ribonucleotide or deoxyribonucleotide. The nucleotide typically contains a monophosphate, diphosphate or triphosphate. The nucleotide may comprise more than three phosphates, such as 4 or 5 phosphates. Phosphates may be attached on the 5' or 3' side of a nucleotide. Nucleotides include, but are not limited to, adenosine monophosphate (AMP), guanosine monophosphate (GMP), thymidine monophosphate (TMP), uridine monophosphate (UMP), 5-methylcytidine monophosphate, 5-hydroxymethylcytidine monophosphate, cytidine monophosphate (CMP), cyclic adenosine monophosphate (cAMP), cyclic guanosine monophosphate (cGMP), deoxyadenosine monophosphate (dAMP), deoxyguanosine monophosphate (dGMP), deoxythymidine monophosphate (dTMP), deoxyuridine monophosphate (dUMP), deoxycytidine monophosphate (dCMP) and deoxymethylcytidine monophosphate. The nucleotides are preferably selected from AMP, TMP, GMP, CMP, UMP, dAMP, dTMP, dGMP, dCMP and dUMP.

A nucleotide may be abasic (i.e. lack a nucleobase). A nucleotide may also lack a nucleobase and a sugar (i.e. is a C3 spacer).

The nucleotides in the polynucleotide may be attached to each other in any manner. The nucleotides are typically attached by their sugar and phosphate groups as in nucleic acids. The nucleotides may be connected via their nucleobases as in pyrimidine dimers.

The polynucleotide may be single stranded or double stranded. At least a portion of the polynucleotide is preferably double stranded.

The polynucleotide can be a nucleic acid, such as deoxyribonucleic acid (DNA) or ribonucleic acid (RNA). The polynucleotide can comprise one strand of RNA hybridised to one strand of DNA. The polynucleotide may be any synthetic nucleic acid known in the art, such as peptide nucleic acid (PNA), glycerol nucleic acid (GNA), threose nucleic acid (TNA), locked nucleic acid (LNA) or other synthetic polymers with nucleotide side chains. The PNA backbone is composed of repeating N-(2-aminoethyl)-glycine units linked by peptide bonds. The GNA backbone is composed of repeating glycol units linked by phosphodiester bonds. The TNA backbone is composed of repeating threose sugars linked together by phosphodiester bonds. LNA is formed from ribonucleotides as discussed above having an extra bridge connecting the 2' oxygen and 4' carbon in the ribose moiety.

The polynucleotide is most preferably ribonucleic acid (RNA) or deoxyribonucleic acid (DNA).

The polynucleotide can be any length. For example, the polynucleotide can be at least 10, at least 50, at least 100, at least 150, at least 200, at least 250, at least 300, at least 400 or at least 500 nucleotides or nucleotide pairs in length. The polynucleotide can be 1000 or more nucleotides or nucleotide pairs, 5000 or more nucleotides or nucleotide pairs in length or 100000 or more nucleotides or nucleotide pairs in length.

Sample

The analyte may be present in any suitable sample. The sample may be a biological sample. The invention may be carried out in vitro using at least one sample obtained from or extracted from any organism or microorganism. The organism or microorganism is typically archaeal, prokaryotic or eukaryotic and typically belongs to one of the five kingdoms: plantae, animalia, fungi, monera and protista. The invention may be carried out in vitro on at least one sample obtained from or extracted from any virus. The sample is preferably a fluid sample. The sample typically comprises a body fluid of the patient. The sample may be urine, lymph, saliva, mucus or amniotic fluid but is preferably blood, plasma or serum. Typically, the sample is human in origin, but alternatively it may be from another mammal animal such as from commercially farmed animals such as horses, cattle, sheep, fish, chickens or pigs or may alternatively be pets such as cats or dogs. Alternatively, the sample may be of plant origin, such as a sample obtained from a commercial crop, such as a cereal, legume, fruit or vegetable, for example wheat, barley, oats, canola, maize, soya, rice, rhubarb, bananas, apples, tomatoes, potatoes, grapes, tobacco, beans, lentils, sugar cane, cocoa, cotton.

The sample may be a non-biological sample. The non-biological sample is preferably a fluid sample. Examples of non-biological samples include surgical fluids, water such as drinking water, sea water or river water, and reagents for laboratory tests.

The sample is typically processed prior to being used in the invention, for example by centrifugation or by passage through a membrane that filters out unwanted molecules or cells, such as red blood cells. The sample may be measured immediately upon being taken. The sample may also be typically stored prior to assay, preferably below −70° C.

Membrane

Any membrane may be used in accordance with the invention. Suitable membranes are well-known in the art. The membrane is preferably an amphiphilic layer. An amphiphilic layer is a layer formed from amphiphilic molecules, such as phospholipids, which have both hydrophilic and lipophilic properties. The amphiphilic molecules may be synthetic or naturally occurring. Non-naturally occurring amphiphiles and amphiphiles which form a monolayer are known in the art and include, for example, block copolymers (Gonzalez-Perez et al., Langmuir, 2009, 25, 10447-10450). Block copolymers are polymeric materials in which two or more monomer sub-units that are polymerised together to create a single polymer chain. Block copolymers typically have properties that are contributed by each monomer sub-unit. However, a block copolymer may have unique properties that polymers formed from the individual sub-units do not possess. Block copolymers can be engineered such that one of the monomer sub-units is hydrophobic (i.e. lipophilic), whilst the other sub-unit(s) are hydrophilic whilst in aqueous media. In this case, the block copolymer may possess amphiphilic properties and may form a structure that mimics a biological membrane. The block copolymer may be a diblock (consisting of two monomer sub-units), but may also be constructed from more than two monomer sub-units to form more complex arrangements that behave as amphiphiles. The copolymer may be a triblock, tetrablock or pentablock copolymer. The membrane is preferably a triblock copolymer membrane.

Archaebacterial bipolar tetraether lipids are naturally occurring lipids that are constructed such that the lipid forms a monolayer membrane. These lipids are generally found in extremophiles that survive in harsh biological environments, thermophiles, halophiles and acidophiles. Their stability is believed to derive from the fused nature of the final bilayer. It is straightforward to construct block copolymer materials that mimic these biological entities by creating a triblock polymer that has the general motif hydrophilic-hydrophobic-hydrophilic. This material may form monomeric membranes that behave similarly to lipid bilayers and encompass a range of phase behaviours from vesicles through to laminar membranes. Membranes formed from these triblock copolymers hold several advantages over biological lipid membranes. Because the triblock copolymer is synthesised, the exact construction can be carefully controlled to provide the correct chain lengths and properties required to form membranes and to interact with pores and other proteins.

Block copolymers may also be constructed from sub-units that are not classed as lipid sub-materials; for example a hydrophobic polymer may be made from siloxane or other non-hydrocarbon based monomers. The hydrophilic sub-section of block copolymer can also possess low protein binding properties, which allows the creation of a membrane that is highly resistant when exposed to raw biological samples. This head group unit may also be derived from non-classical lipid head-groups.

Triblock copolymer membranes also have increased mechanical and environmental stability compared with biological lipid membranes, for example a much higher operational temperature or pH range. The synthetic nature of the block copolymers provides a platform to customise polymer based membranes for a wide range of applications.

The membrane is most preferably one of the membranes disclosed in International Application No. PCT/GB2013/052766 or PCT/GB2013/052767.

The amphiphilic molecules may be chemically-modified or functionalised to facilitate coupling of the analyte.

Figure 8:
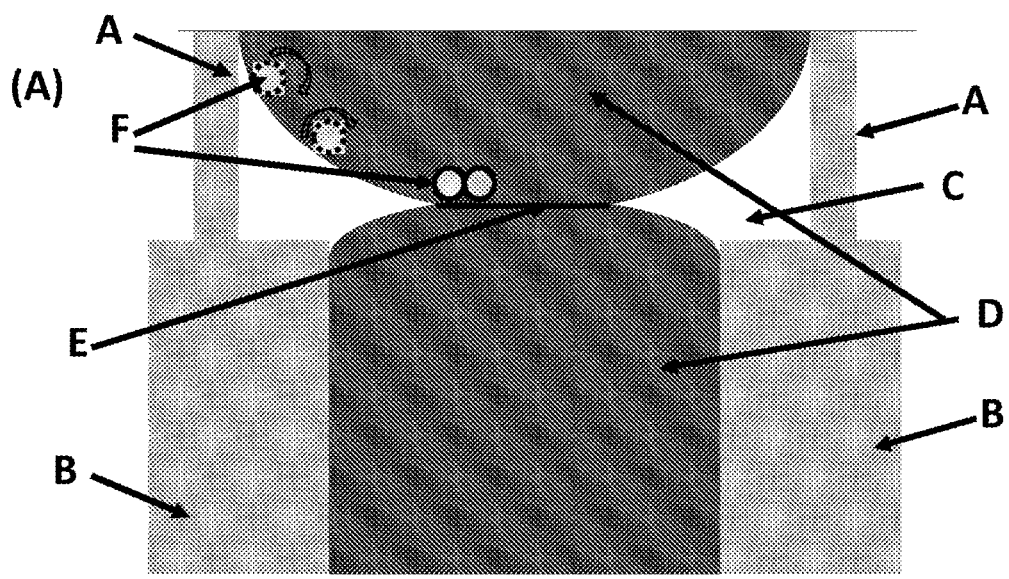
FIG. 8A shows a cartoon representation of the side of a single well on an array chip. The pillars made of TOK photoresist are labelled A, the side of the well is labelled B, the buffer inside and above the well is labelled D and shown as dark grey, the membrane (amphiphilic layer) is labelled E and shown as a black line and F represents the microparticles coated in DNA. This figure shows that the microparticles are deposited on the edge of the oil layer and the microparticles then roll along the edge of the oil layer and collect on top of the membrane.
FIG. 8B shows a top view and a side on view image of the same single well in an array chip (10× magnification). There was a fluorophore added to the buffer solution and a different coloured fluorophore added to the pre-treatment (oil) to illustrate where these solutions were present in the system. These images illustrate that the system shown in cartoon form in FIG. 8A is produced in the array chip, as these are images taken using a Confocal microscope.
Figure 8:
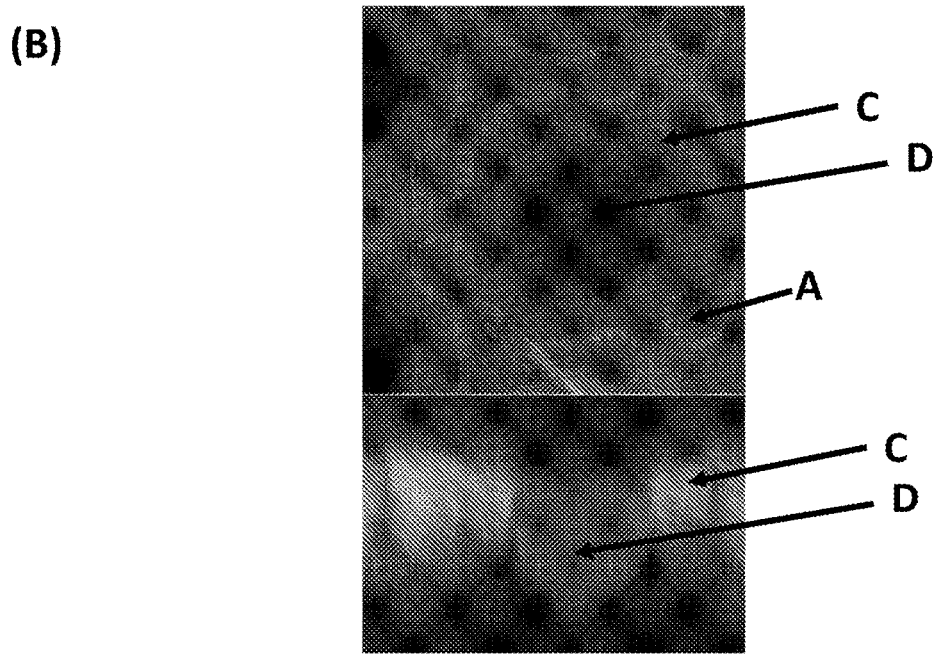

The amphiphilic layer may be a monolayer or a bilayer. The amphiphilic layer is typically planar. The amphiphilic layer may be curved. The amphiphilic layer may be supported. The amphiphilic layer may be concave. The amphiphilic layer may be suspended from raised pillars (labelled A) as shown in FIG. 8 such that the peripheral region of the amphiphilic layer (which is attached to the pillars labelled A) is higher than the amphiphilic layer region shown in FIG. 8 and labelled E. This may allow the microparticle to travel, move, slide or roll along the membrane as described above.

Amphiphilic membranes are typically naturally mobile, essentially acting as two dimensional fluids with lipid diffusion rates of approximately $10^{-8}$ cm s-1. This means that the pore and coupled analyte can typically move within an amphiphilic membrane.

The membrane may be a lipid bilayer. Lipid bilayers are models of cell membranes and serve as excellent platforms for a range of experimental studies. For example, lipid bilayers can be used for in vitro investigation of membrane proteins by single-channel recording. Alternatively, lipid bilayers can be used as biosensors to detect the presence of a range of substances. The lipid bilayer may be any lipid bilayer. Suitable lipid bilayers include, but are not limited to, a planar lipid bilayer, a supported bilayer or a liposome. The lipid bilayer is preferably a planar lipid bilayer. Suitable lipid bilayers are disclosed in International Application No. PCT/GB08/000563 (published as WO 2008/102121), International Application No. PCT/GB08/004127 (published as WO 2009/077734) and International Application No. PCT/GB2006/001057 (published as WO 2006/100484).

Methods for forming lipid bilayers are known in the art. Suitable methods are disclosed in the Example. Lipid bilayers are commonly formed by the method of Montal and Mueller (Proc. Natl. Acad. Sci. USA., 1972; 69: 3561-3566), in which a lipid monolayer is carried on aqueous solution/air interface past either side of an aperture which is perpendicular to that interface. The lipid is normally added to the surface of an aqueous electrolyte solution by first dissolving it in an organic solvent and then allowing a drop of the solvent to evaporate on the surface of the aqueous solution on either side of the aperture. Once the organic solvent has evaporated, the solution/air interfaces on either side of the aperture are physically moved up and down past the aperture until a bilayer is formed. Planar lipid bilayers may be formed across an aperture in a membrane or across an opening into a recess.

The method of Montal & Mueller is popular because it is a cost-effective and relatively straightforward method of forming good quality lipid bilayers that are suitable for protein pore insertion. Other common methods of bilayer formation include tip-dipping, painting bilayers and patch-clamping of liposome bilayers.

Tip-dipping bilayer formation entails touching the aperture surface (for example, a pipette tip) onto the surface of a test solution that is carrying a monolayer of lipid. Again, the lipid monolayer is first generated at the solution/air interface by allowing a drop of lipid dissolved in organic solvent to evaporate at the solution surface. The bilayer is then formed by the Langmuir-Schaefer process and requires mechanical automation to move the aperture relative to the solution surface.

For painted bilayers, a drop of lipid dissolved in organic solvent is applied directly to the aperture, which is submerged in an aqueous test solution. The lipid solution is spread thinly over the aperture using a paintbrush or an equivalent. Thinning of the solvent results in formation of a lipid bilayer. However, complete removal of the solvent from the bilayer is difficult and consequently the bilayer formed by this method is less stable and more prone to noise during electrochemical measurement.

Patch-clamping is commonly used in the study of biological cell membranes. The cell membrane is clamped to the end of a pipette by suction and a patch of the membrane becomes attached over the aperture. The method has been adapted for producing lipid bilayers by clamping liposomes which then burst to leave a lipid bilayer sealing over the aperture of the pipette. The method requires stable, giant and unilamellar liposomes and the fabrication of small apertures in materials having a glass surface.

Liposomes can be formed by sonication, extrusion or the Mozafari method (Colas et al. (2007) Micron 38:841-847).

In a preferred embodiment, the lipid bilayer is formed as described in International Application No. PCT/GB08/004127 (published as WO 2009/077734). Advantageously in this method, the lipid bilayer is formed from dried lipids. In a most preferred embodiment, the lipid bilayer is formed across an opening as described in WO2009/077734 (PCT/GB08/004127).

A lipid bilayer is formed from two opposing layers of lipids. The two layers of lipids are arranged such that their hydrophobic tail groups face towards each other to form a hydrophobic interior. The hydrophilic head groups of the lipids face outwards towards the aqueous environment on each side of the bilayer. The bilayer may be present in a number of lipid phases including, but not limited to, the liquid disordered phase (fluid lamellar), liquid ordered phase, solid ordered phase (lamellar gel phase, interdigitated gel phase) and planar bilayer crystals (lamellar sub-gel phase, lamellar crystalline phase).

Any lipid composition that forms a lipid bilayer may be used. The lipid composition is chosen such that a lipid bilayer having the required properties, such as surface charge, ability to support membrane proteins, packing density or mechanical properties, is formed. The lipid composition can comprise one or more different lipids. For instance, the lipid composition can contain up to 100 lipids. The lipid composition preferably contains 1 to 10 lipids. The lipid composition may comprise naturally-occurring lipids and/or artificial lipids.

The lipids typically comprise a head group, an interfacial moiety and two hydrophobic tail groups which may be the same or different. Suitable head groups include, but are not limited to, neutral head groups, such as diacylglycerides (DG) and ceramides (CM); zwitterionic head groups, such as phosphatidylcholine (PC), phosphatidylethanolamine (PE) and sphingomyelin (SM); negatively charged head groups, such as phosphatidylglycerol (PG); phosphatidylserine (PS), phosphatidylinositol (PI), phosphatic acid (PA) and cardiolipin (CA); and positively charged headgroups, such as trimethylammonium-Propane (TAP). Suitable interfacial moieties include, but are not limited to, naturally-occurring interfacial moieties, such as glycerol-based or ceramide-based moieties. Suitable hydrophobic tail groups include, but are not limited to, saturated hydrocarbon chains, such as lauric acid (n-Dodecanolic acid), myristic acid (n-Tetradecononic acid), palmitic acid (n-Hexadecanoic acid), stearic acid (n-Octadecanoic) and arachidic (n-Eicosanoic); unsaturated hydrocarbon chains, such as oleic acid (cis-9-Octadecanoic); and branched hydrocarbon chains, such as phytanoyl. The length of the chain and the position and number of the double bonds in the unsaturated hydrocarbon chains can vary. The length of the chains and the position and number of the branches, such as methyl groups, in the branched hydrocarbon chains can vary. The hydrophobic tail groups can be linked to the interfacial moiety as an ether or an ester. The lipids may be mycolic acid.

The lipids can also be chemically-modified. The head group or the tail group of the lipids may be chemically-modified. Suitable lipids whose head groups have been chemically-modified include, but are not limited to, PEG-modified lipids, such as 1,2-Diacyl-sn-Glycero-3-Phosphoethanolamine-N-[Methoxy(Polyethylene glycol)-2000]; functionalised PEG Lipids, such as 1,2-Distearoyl-sn-Glycero-3 Phosphoethanolamine-N-[Biotinyl(Polyethylene Glycol)2000]; and lipids modified for conjugation, such as 1,2-Dioleoyl-sn-Glycero-3-Phosphoethanolamine-N-(succinyl) and 1,2-Dipalmitoyl-sn-Glycero-3-Phosphoethanolamine-N-(Biotinyl). Suitable lipids whose tail groups have been chemically-modified include, but are not limited to, polymerisable lipids, such as 1,2-bis(10,12-tricosadiynoyl)-sn-Glycero-3-Phosphocholine; fluorinated lipids, such as 1-Palmitoyl-2-(16-Fluoropalmitoyl)-sn-Glycero-3-Phosphocholine; deuterated lipids, such as 1,2-Dipalmitoyl-D62-sn-Glycero-3-Phosphocholine; and ether linked lipids, such as 1,2-Di-O-phytanyl-sn-Glycero-3-Phosphocholine. The lipids may be chemically-modified or functionalised to facilitate coupling of the analyte.

The amphiphilic layer, for example the lipid composition, typically comprises one or more additives that will affect the properties of the layer. Suitable additives include, but are not limited to, fatty acids, such as palmitic acid, myristic acid and oleic acid; fatty alcohols, such as palmitic alcohol, myristic alcohol and oleic alcohol; sterols, such as cholesterol, ergosterol, lanosterol, sitosterol and stigmasterol; lyso-phospholipids, such as 1-Acyl-2-Hydroxy-sn-Glycero-3-Phosphocholine; and ceramides.

In another preferred embodiment, the membrane is a solid state layer. Solid state layers can be formed from both organic and inorganic materials including, but not limited to, microelectronic materials, insulating materials such as $Si_3N_4$, $Al_2O_3$, and SiO, organic and inorganic polymers such as polyamide, plastics such as Teflon® or elastomers such as two-component addition-cure silicone rubber, and glasses. The solid state layer may be formed from graphene. Suitable graphene layers are disclosed in International Application No. PCT/US2008/010637 (published as WO 2009/035647). Yusko et al., Nature Nanotechnology, 2011; 6: 253-260 and US Patent Application No. 2013/0048499 describe the delivery of proteins to transmembrane pores in solid state layers without the use of microparticles. The method of the invention may be used to improve the delivery in the methods disclosed in these documents.

The method is typically carried out using (i) an artificial amphiphilic layer comprising a pore, (ii) an isolated, naturally-occurring lipid bilayer comprising a pore, or (iii) a cell having a pore inserted therein. The method is typically carried out using an artificial amphiphilic layer, such as an artificial triblock copolymer layer. The layer may comprise other transmembrane and/or intramembrane proteins as well as other molecules in addition to the pore. Suitable apparatus and conditions are discussed below. The method of the invention is typically carried out in vitro.

Transmembrane Pore

A transmembrane pore is a structure that crosses the membrane to some degree. It permits hydrated ions driven by an applied potential to flow across or within the membrane. The transmembrane pore typically crosses the entire membrane so that hydrated ions may flow from one side of the membrane to the other side of the membrane. However, the transmembrane pore does not have to cross the membrane. It may be closed at one end. For instance, the pore may be a well, gap, channel, trench or slit in the membrane along which or into which hydrated ions may flow.

Any transmembrane pore may be used in the invention. The pore may be biological or artificial. Suitable pores include, but are not limited to, protein pores, polynucleotide pores and solid state pores. The pore may be a DNA origami pore (Langecker et al., Science, 2012; 338: 932-936).

The transmembrane pore is preferably a transmembrane protein pore. A transmembrane protein pore is a polypeptide or a collection of polypeptides that permits hydrated ions, such as analyte, to flow from one side of a membrane to the other side of the membrane. In the present invention, the transmembrane protein pore is capable of forming a pore that permits hydrated ions driven by an applied potential to flow from one side of the membrane to the other. The transmembrane protein pore preferably permits analyte such as nucleotides to flow from one side of the membrane, such as a triblock copolymer membrane, to the other. The transmembrane protein pore allows a polynucleotide, such as DNA or RNA, to be moved through the pore.

The transmembrane protein pore may be a monomer or an oligomer. The pore is preferably made up of several repeating subunits, such as at least 6, at least 7, at least 8, at least 9, at least 10, at least 11, at least 12, at least 13, at least 14, at least 15, or at least 16 subunits. The pore is preferably a hexameric, heptameric, octameric or nonameric pore. The pore may be a homo-oligomer or a hetero-oligomer.

The transmembrane protein pore typically comprises a barrel or channel through which the ions may flow. The subunits of the pore typically surround a central axis and contribute strands to a transmembrane β barrel or channel or a transmembrane α-helix bundle or channel.

The barrel or channel of the transmembrane protein pore typically comprises amino acids that facilitate interaction with analyte, such as nucleotides, polynucleotides or nucleic acids. These amino acids are preferably located near a constriction of the barrel or channel. The transmembrane protein pore typically comprises one or more positively charged amino acids, such as arginine, lysine or histidine, or aromatic amino acids, such as tyrosine or tryptophan. These amino acids typically facilitate the interaction between the pore and nucleotides, polynucleotides or nucleic acids.

Transmembrane protein pores for use in accordance with the invention can be derived from β-barrel pores or α-helix bundle pores. β-barrel pores comprise a barrel or channel that is formed from β-strands. Suitable β-barrel pores include, but are not limited to, β-toxins, such as α-hemolysin, anthrax toxin and leukocidins, and outer membrane proteins/porins of bacteria, such as *Mycobacterium smegmatis* porin (Msp), for example MspA, MspB, MspC or MspD, CsgG, outer membrane porin F (OmpF), outer membrane porin G (OmpG), outer membrane phospholipase A and *Neisseria* autotransporter lipoprotein (NalP) and other pores, such as lysenin. α-helix bundle pores comprise a barrel or channel that is formed from α-helices. Suitable α-helix bundle pores include, but are not limited to, inner membrane proteins and a outer membrane proteins, such as WZA and ClyA toxin. The transmembrane pore may be derived from lysenin. Suitable pores derived from CsgG are disclosed in International Application No. PCT/EP2015/069965. Suitable pores derived from lysenin are disclosed in International Application No. PCT/GB2013/050667 (published as WO 2013/153359). The transmembrane pore may be derived from Msp or from α-hemolysin (α-HL). The wild type α-hemolysin pore is formed of 7 identical monomers or sub-units (i.e., it is heptameric). The sequence of one monomer or sub-unit of α-hemolysin-NN is shown in SEQ ID NO:4.

The transmembrane protein pore is preferably derived from Msp, preferably from MspA. Such a pore will be oligomeric and typically comprises 7, 8, 9 or 10 monomers derived from Msp. The pore may be a homo-oligomeric pore derived from Msp comprising identical monomers. Alternatively, the pore may be a hetero-oligomeric pore derived from Msp comprising at least one monomer that differs from the others. Preferably the pore is derived from MspA or a homolog or paralog thereof.

A monomer derived from Msp typically comprises the sequence shown in SEQ ID NO: 2 or a variant thereof. SEQ ID NO: 2 is the MS-(B1)8 mutant of the MspA monomer. It includes the following mutations: D90N, D91N, D93N, D118R, D134R and E139K. A variant of SEQ ID NO: 2 is a polypeptide that has an amino acid sequence which varies from that of SEQ ID NO: 2 and which retains its ability to form a pore. The ability of a variant to form a pore can be assayed using any method known in the art. For instance, the variant may be inserted into an amphiphilic layer along with other appropriate subunits and its ability to oligomerise to form a pore may be determined. Methods are known in the art for inserting subunits into membranes, such as amphiphilic layers. For example, subunits may be suspended in a purified form in a solution containing a triblock copolymer membrane such that it diffuses to the membrane and is inserted by binding to the membrane and assembling into a functional state. Alternatively, subunits may be directly inserted into the membrane using the "pick and place" method described in M. A. Holden, H. Bayley. J. Am. Chem. Soc. 2005, 127, 6502-6503 and International Application No. PCT/GB2006/001057 (published as WO 2006/100484).

Over the entire length of the amino acid sequence of SEQ ID NO: 2, a variant will preferably be at least 50% homologous to that sequence based on amino acid identity. More preferably, the variant may be at least 55%, at least 60%, at least 65%, at least 70%, at least 75%, at least 80%, at least 85%, at least 90% and more preferably at least 95%, 97% or 99% homologous based on amino acid identity to the amino acid sequence of SEQ ID NO: 2 over the entire sequence. There may be at least 80%, for example at least 85%, 90% or 95%, amino acid identity over a stretch of 100 or more, for example 125, 150, 175 or 200 or more, contiguous amino acids ("hard homology").

Standard methods in the art may be used to determine homology. For example the UWGCG Package provides the BESTFIT program which can be used to calculate homology, for example used on its default settings (Devereux et al (1984) *Nucleic Acids Research* 12, p 387-395). The PILEUP and BLAST algorithms can be used to calculate homology or line up sequences (such as identifying equivalent residues or corresponding sequences (typically on their default settings)), for example as described in Altschul S. F. (1993) J Mol Evol 36:290-300; Altschul, S. F et al (1990) J Mol Biol 215:403-10. Software for performing BLAST analyses is publicly available through the National Center for Biotechnology Information (http://www.ncbi.nlm.nih.gov/).

SEQ ID NO: 2 is the MS-(B1)8 mutant of the MspA monomer. The variant may comprise any of the mutations in the MspB, C or D monomers compared with MspA. The mature forms of MspB, C and D are shown in SEQ ID NOs: 5 to 7. In particular, the variant may comprise the following substitution present in MspB: A138P. The variant may comprise one or more of the following substitutions present in MspC: A96G, N102E and A138P. The variant may comprise one or more of the following mutations present in MspD: Deletion of G1, L2V, E5Q, L8V, D13G, W21A, D22E, K47T, I49H, I68V, D91G, A96Q, N102D, S103T, V104I, S136K and G141A. The variant may comprise combinations of one or more of the mutations and substitutions from Msp B, C and D. The variant preferably comprises the mutation L88N. A variant of SEQ ID NO: 2 has the mutation L88N in addition to all the mutations of MS-B1 and is called MS-(B2)8. The pore used in the invention is preferably MS-(B2)8. The variant of SEQ ID NO: 2 preferably comprises one or more of D56N, D56F, E59R, G75S, G77S, A96D and Q126R. A variant of SEQ ID NO: 2 has the mutations G75S/G77S/L88N/Q126R in addition to all the mutations of MS-B1 and is called MS-B2C. The pore used in the invention is preferably MS-(B2)8 or MS-(B2C)8. The variant of SEQ ID NO: 2 preferably comprises N93D. The variant more preferably comprises the mutations G75S/G77S/L88N/N93D/Q126R.

Amino acid substitutions may be made to the amino acid sequence of SEQ ID NO: 2 in addition to those discussed above, for example up to 1, 2, 3, 4, 5, 10, 20 or 30 substitutions. Conservative substitutions replace amino acids with other amino acids of similar chemical structure, similar chemical properties or similar side-chain volume. The amino acids introduced may have similar polarity, hydrophilicity, hydrophobicity, basicity, acidity, neutrality or charge to the amino acids they replace. Alternatively, the conservative substitution may introduce another amino acid that is aromatic or aliphatic in the place of a pre-existing aromatic or aliphatic amino acid.

Any of the proteins described herein, such as the transmembrane protein pores, may be modified to assist their identification or purification, for example by the addition of histidine residues (a his tag), aspartic acid residues (an asp tag), a streptavidin tag, a flag tag, a SUMO tag, a GST tag or a MBP tag, or by the addition of a signal sequence to promote their secretion from a cell where the polypeptide does not naturally contain such a sequence. An alternative to introducing a genetic tag is to chemically react a tag onto a native or engineered position on the pore or construct. An example of this would be to react a gel-shift reagent to a cysteine engineered on the outside of the pore. This has been demonstrated as a method for separating hemolysin hetero-oligomers (Chem Biol. 1997 July; 4(7):497-505).

The pore may be labelled with a revealing label. The revealing label may be any suitable label which allows the pore to be detected. Suitable labels include, but are not limited to, fluorescent molecules, radioisotopes, e.g. $^{125}$I, $^{35}$S, enzymes, antibodies, antigens, polynucleotides and ligands such as biotin.

Any of the proteins described herein, such as the transmembrane protein pores, may be made synthetically or by recombinant means. For example, the pore may be synthesised by in vitro translation and transcription (IVTT). The amino acid sequence of the pore may be modified to include non-naturally occurring amino acids or to increase the stability of the protein. When a protein is produced by synthetic means, such amino acids may be introduced during production. The pore may also be altered following either synthetic or recombinant production.

Any of the proteins described herein, such as the transmembrane protein pores, can be produced using standard methods known in the art. Polynucleotide sequences encoding a pore or construct may be derived and replicated using standard methods in the art. Polynucleotide sequences encoding a pore or construct may be expressed in a bacterial host cell using standard techniques in the art. The pore may be produced in a cell by in situ expression of the polypeptide from a recombinant expression vector. The expression vector optionally carries an inducible promoter to control the expression of the polypeptide. These methods are described in Sambrook, J. and Russell, D. (2001). Molecular Cloning: A Laboratory Manual, 3rd Edition. Cold Spring Harbor Laboratory Press, Cold Spring Harbor, N.Y.

The pore may be produced in large scale following purification by any protein liquid chromatography system from protein producing organisms or after recombinant expression. Typical protein liquid chromatography systems include FPLC, AKTA systems, the Bio-Cad system, the Bio-Rad BioLogic system and the Gilson HPLC system.

Microparticle

A microparticle is used to deliver the analyte. Any number of microparticles can be used in the method of the invention. For instance, the method of the invention may use a single microparticle or 2, 3, 4, 5, 6, 7, 8, 9, 10, 20, 30, 50, 100, 1,000, 5,000, 10,000, 100,000, 500,000 or 1,000,000 or more microparticles. If two or more microparticles are used, the microparticles may be the same. Alternatively, a mixture of different microparticles may be used.

Each microparticle may have one analyte attached. Alternatively, each microparticle may have two or more analytes, such as 3 or more, 4 or more, 5 or more, 6 or more, 7 or more, 8 or more, 9 or more, 10 or more, 20 or more, 30 or more, 50 or more, 100 or more, 500 or more, 1,000 or more, 5,000 or more, 10,000 or more, 100,000 or more, 1000,000 or more or 5000,000 or more analytes, attached. A microparticle may be substantially or completed coated or covered with analyte. A microparticle may have an analyte attached over substantially all of or all of its surface. A microparticle may be attached to an analyte such as a polynucleotide via an adaptor. The adaptor may be a Y-adaptor or a hairpin adaptor (see below)

An analyte, i.e. a single instance of an analyte, may be attached to two or more microparticles. An analyte, i.e. a single instance of an analyte, may be attached to any number of the microparticles discussed above.

A microparticle is a microscopic particle whose size is typically measured in micrometers (μm). Microparticles may also known as microspheres or microbeads. The microparticle may be a nanoparticle. A nanoparticle is a microscopic particle whose size is typically measured in nanometers (nm).

A microparticle typically has a particle size of from about 0.001 μm to about 500 μm. For instance, a nanoparticle may have a particle size of from about 0.01 μm to about 200 μm or about 0.1 μm to about 100 μm. More often, a microparticle has a particle size of from about 0.5 μm to about 100 μm, or for instance from about 1 μm to about 50 μm. The microparticle may have a particle size of from about 1 nm to about 1000 nm, such as from about 10 nm to about 500 nm, about 20 nm to about 200 nm or from about 30 nm to about 100 nm.

A microparticle may be spherical or non-spherical. Spherical microparticles may be called microspheres. Non-spherical particles may for instance be plate-shaped, needle-shaped, irregular or tubular. The term "particle size" as used herein means the diameter of the particle if the particle is spherical or, if the particle is non-spherical, the volume-based particle size. The volume-based particle size is the diameter of the sphere that has the same volume as the non-spherical particle in question.

If two or more microparticles are used in the method, the average particle size of the microparticles may be any of the sizes discussed above, such as from about 0.5 μm to about 500 μm. A population of two or more microparticles preferably has a coefficient of variation (ratio of the standard deviation to the mean) of 10% or less, such as 5% or less or 2% or less.

Any method may be used to determine the size of the microparticle. Suitable methods include, but are not limited to, flow cytometry (see, for example, Chandler et al., J Thromb Haemost. 2011 June; 9(6):1216-24).

The microparticle may be formed from any material. The microparticle is preferably formed from a ceramic, glass, silica, a polymer or a metal. The polymer may be a natural polymer, such as polyhydroxyalkanoate, dextran, polylactide, agarose, cellulose, starch or chitosan, or a synthetic polymer, such as polyurethane, polystyrene, poly(vinyl chloride), silane or methacrylate. Suitable microparticles are known in the art and are commercially available. Ceramic and glass microspheres are commercially available from 3M®. Silica and polymer microparticles are commercially available from EPRUI Nanoparticles & Microspheres Co. Ltd. Microparticles are also commercially available from Polysciences Inc., Bangs Laboratories Inc. and Life Technologies.

The microparticle may be solid. The microparticle may be hollow. The microparticle may be formed from polymer fibers.

If the analyte is a polynucleotide, the microparticle may be derived from the kit used to extract and isolate the polynucleotide.

The surface of the microparticle may interact with and attach the analyte. The surface may naturally interact with the analyte without functionalisation. The surface of the microparticle is typically functionalised to facilitate attachment of the analyte. Suitable functionalisations are known in the art. For instance, the surface of the microparticle may be functionalised with a polyhistidine-tag (hexa histidine-tag, 6×His-tag, His6 tag or His-tag®), Ni-NTA, streptavidin, biotin, an oligonucleotide, a polynucleotide (such as DNA, RNA, PNA, GNA, TNA or LNA), carboxyl groups, quaternary amine groups, thiol groups, azide groups, alkyne groups, DIBO, lipid, FLAG-tag (FLAG octapeptide, polynucleotide binding proteins (including any of those discussed below), peptides, proteins, antibodies or antibody fragments. Antibody fragments are discussed in more detail below. The microparticle may also be functionalised with any of the linkers or groups discussed below with reference to attachment.

The microparticle may be functionalised with a molecule or group which specifically binds to the analyte. In this instance, the analyte which will be attached to the microparticle and delivered to the transmembrane pore may be called the target analyte. This allows the microparticle to select or capture the target analyte from a sample containing other analytes. A molecule or group specifically binds to the target analyte if it binds to the target analyte with preferential or high affinity, but does not bind or binds with only low affinity to other or different analytes. A molecule or group binds with preferential or high affinity if it binds with a Kd of $1 \times 10^{-6}$ M or less, more preferably $1 \times 10^{-7}$ M or less, $5 \times 10^{-8}$ M or less, more preferably $1 \times 10^{-8}$ M or less or more preferably $5 \times 10^{-9}$ M or less. A molecule or group binds with low affinity if it binds with a Kd of $1 \times 10^{-6}$ M or more, more preferably $1 \times 10^{-5}$ M or more, more preferably $1 \times 10^{-4}$ M or more, more preferably $1 \times 10^{-3}$ M or more, even more preferably $1 \times 10^{-2}$ M or more.

Preferably, the molecule or group binds to the target analyte with an affinity that is at least 10 times, such as at least 50, at least 100, at least 200, at least 300, at least 400, at least 500, at least 1000 or at least 10,000 times, greater than its affinity for other analytes. Affinity can be measured using known binding assays, such as those that make use of fluorescence and radioisotopes. Competitive binding assays are also known in the art. The strength of binding between peptides or proteins and polynucleotides can be measured using nanopore force spectroscopy as described in Hornblower et al., Nature Methods. 4: 315-317. (2007).

If the target analyte is a polynucleotide, the microparticle may be functionalised with an oligonucleotide or a polynucleotide (such as any of those discussed above) which specifically hybridises to the target polynucleotide analyte or comprises a portion or region which is complementary to a portion or region of the target polynucleotide analyte. This allows the microparticle to select or capture the target polynucleotide analyte from a sample containing other analytes, such as other polynucleotides. An oligonucleotide or polynucleotide specifically hybridises to a target polynucleotide when it hybridises with preferential or high affinity to the target polynucleotide but does not substantially hybridise, does not hybridise or hybridises with only low affinity to other polynucleotide. An oligonucleotide or polynucleotide specifically hybridises if it hybridises to the target polynucleotide with a melting temperature ($T_m$) that is at least 2° C., such as at least 3° C., at least 4° C., at least 5° C., at least 6° C., at least 7° C., at least 8° C., at least 9° C. or at least 10° C., greater than its $T_m$ for other sequences. More preferably, the oligonucleotide or polynucleotide hybridises to the target polynucleotide with a $T_m$ that is at least 2° C., such as at least 3° C., at least 4° C., at least 5° C., at least 6° C., at least 7° C., at least 8° C., at least 9° C., at least 10° C., at least 20° C., at least 30° C. or at least 40°

C., greater than its $T_m$ for other nucleic acids. Preferably, the oligonucleotide or polynucleotide hybridises to the target polynucleotide with a $T_m$ that is at least 2° C., such as at least 3° C., at least 4° C., at least 5° C., at least 6° C., at least 7° C., at least 8° C., at least 9° C., at least 10° C., at least 20° C., at least 30° C. or at least 40° C., greater than its $T_m$ for a sequence which differs from the target polynucleotide by one or more nucleotides, such as by 1, 2, 3, 4 or 5 or more nucleotides. The oligonucleotide or polynucleotide typically hybridises to the target polynucleotide with a $T_m$ of at least 90° C., such as at least 92° C. or at least 95° C. $T_m$ can be measured experimentally using known techniques, including the use of DNA microarrays, or can be calculated using publicly available $T_m$ calculators, such as those available over the internet.

Conditions that permit the hybridisation are well-known in the art (for example, Sambrook et al., 2001, Molecular Cloning: a laboratory manual, 3rd edition, Cold Spring Harbour Laboratory Press; and Current Protocols in Molecular Biology, Chapter 2, Ausubel et al., Eds., Greene Publishing and Wiley-Interscience, New York (1995)). Hybridisation can be carried out under low stringency conditions, for example in the presence of a buffered solution of 30 to 35% formamide, 1 M NaCl and 1 SDS (sodium dodecyl sulfate) at 37° C. followed by a 20 wash in from 1× (0.1650 M Na⁺) to 2× (0.33 M Na⁺) SSC (standard sodium citrate) at 50° C. Hybridisation can be carried out under moderate stringency conditions, for example in the presence of a buffer solution of 40 to 45% formamide, 1 M NaCl, and 1% SDS at 37° C., followed by a wash in from 0.5× (0.0825 M Na⁺) to 1× (0.1650 M Na⁺) SSC at 55° C. Hybridisation can be carried out under high stringency conditions, for example in the presence of a buffered solution of 50% formamide, 1 M NaCl, 1% SDS at 37° C., followed by a wash in 0.1× (0.0165 M Na⁺) SSC at 60° C.

The oligonucleotide or polynucleotide may comprise a portion or region which is substantially complementary to a portion or region of the target polynucleotide. The region or portion of the oligonucleotide or polynucleotide may therefore have 1, 2, 3, 4, 5, 6, 7, 8, 9, 10 or more mismatches across a region of 5, 10, 15, 20, 21, 22, 30, 40 or 50 nucleotides compared with the portion or region in the target polynucleotide.

A portion of region is typically 50 nucleotides or fewer, such as 40 nucleotides or fewer, 30 nucleotides or fewer, 20 nucleotides or fewer, 10 nucleotides or fewer or 5 nucleotides or fewer.

The microparticle is preferably paramagnetic or magnetic. The microparticle preferably comprises a paramagnetic or a superparamagnetic material or a paramagnetic or a superparamagnetic metal, such as iron. Any suitable magnetic microparticle may be used. For instance, magnetic beads commercially available from, for instance, Clontech, Promega, Invitrogen ThermoFisher Scientific and NEB, may be used. In some embodiments, the microparticle comprises a magnetic particle with an organic group such as a metal-chelating group, such as nitrilotriacetic acid (NTA), attached. The organic component may, for instance, comprise a group selected from —C(=O)O—, —C—O—C—, —C(=O)—, —NH—, —C(=O)—NH, —C(=O)—CH₂—I, —S(=O)₂— and —S—. The organic component may comprise a metal chelating group, such as NTA (nitrilotriacetic acid). Usually, a metal such as gold, iron, nickel or cobalt is also attached to the metal-chelating group. Magnetic beads of this sort are commonly used for capturing His-tagged proteins, but are also suitable for use in the invention.

The microparticle is most preferably a His-Tag Dynabead® which is commercially available from Life Technologies, Mag Strep beads from IBA, Streptavidin magnetic beads from NEB, Solid Phase Reversible Immobilization (SPRI) beads or Agencourt AMPure XP beads from Beckman Coulter or Dynabeads® MyOne™ Streptavidin C1 (ThermoFisher Scientific).

Other Methods

The invention also provides a method for delivering an analyte to a transmembrane pore in a membrane, comprising:
(a) providing the analyte attached to a solid support; and
(b) delivering the solid support towards the membrane and thereby delivering the analyte to the transmembrane pore.

The method preferably comprises positioning the solid support near to or adjacent to the membrane and allowing the solid support to move towards the membrane. The method preferably comprises positioning the solid support near to or adjacent to the membrane and moving the solid support towards the membrane. The solid support may contact the membrane. The solid support does not have to contact the membrane.

The solid support may be any solid support. Suitable examples include, but are not limited to, a probe, a plate, a column, a pin and a dipstick. The probe may be any of those discussed in M. A. Holden, H. Bayley. J. Am. Chem. Soc. 2005, 127, 6502-6503 and International Application No. PCT/GB2006/001057 (published as WO 2006/100484).

Any of the embodiments discussed above and below, such as analytes, samples, pores, membranes, apparatuses, functionalisation, attachment, delivery, coupling, uncoupling, removal, washing and characterisation, equally apply to this method.

The invention also provides a kit for delivering an analyte to a transmembrane pore in a membrane, comprising (a) a solid support and (b) one or more anchors which are capable of coupling the analyte to the membrane. Any of the kit embodiments discussed below equally apply to this kit.

Attachment

The analyte and microparticle can be attached in any manner. For instance, the analyte may be attached to the microparticle using any of the coupling methods discussed below. The analyte may be specifically attached to the microparticle using any method discussed below.

The analyte may be non-specifically attached to the microparticle. The analyte may be adsorbed onto the microparticle. The analyte is adsorbed onto the microparticle if it is attached as a thin film on the outside surface of the microparticle and/or on internal surfaces within the microparticle.

The analyte may be attached to the microparticle at one point. The analyte may be attached to the microparticle at two or more points, such as 3, 4, 5, 6, 7, 8, 9, 10 or more points, for instance if two or more linkers are used.

Protein analytes may be attached via their naturally occurring amino acids, such as cysteines, threonines, serines, aspartates, asparagines, glutamates and glutamines. Naturally occurring amino acids may be modified to facilitate attachment. For instance, the naturally occurring amino acids may be modified by acylation, phosphorylation, glycosylation or farnesylation. Other suitable modifications are known in the art. Modifications to naturally occurring amino acids may be post-translational modifications. Protein analytes may be attached via amino acids that have been introduced into their sequences. Such amino acids are preferably introduced by substitution. The introduced amino acid may be cysteine or a non-natural amino acid that facilitates attachment. Suitable non-natural amino acids include, but are not limited to, 4-azido-L-phenylalanine (Faz), and any one of the amino acids numbered 1-71 included in FIG. 1 of Liu C. C. and Schultz P. G., Annu. Rev. Biochem., 2010, 79, 413-444.

The analyte may be attached to the microparticle via a linker molecule. The analyte may be attached to the microparticle using one or more, such as two or three, linkers. Linkers can comprise any molecule that stretches across the distance required. Linkers can vary in length from one carbon (phosgene-type linkers) to many Angstroms. Examples of linear molecules that are suitable for use as linkers, include but are not limited to, are polyethyleneglycols (PEGs), polypeptides, polysaccharides, deoxyribonucleic acid (DNA), peptide nucleic acid (PNA), threose nucleic acid (TNA), glycerol nucleic acid (GNA), saturated and unsaturated hydrocarbons, polyamides. These linkers may be inert or reactive, in particular they may be chemically cleavable at a defined position, or may be themselves modified with a fluorophore or ligand. The linker is preferably resistant to dithiothreitol (DTT). Preferred flexible peptide linkers are stretches of 2 to 20, such as 4, 6, 8, 10 or 16, serine and/or glycine amino acids. More preferred flexible linkers include $(SG)_1$, $(SG)_2$, $(SG)_3$, $(SG)_4$, $(SG)_5$, $(SG)_8$, $(SG)_{10}$, $(SG)_{15}$ or $(SG)_{20}$ wherein S is serine and G is glycine. Preferred rigid linkers are stretches of 2 to 30, such as 4, 6, 8, 16 or 24, proline amino acids. More preferred rigid linkers include $(P)_{12}$ wherein P is proline.

The analyte may be attached to the microparticle using one or more chemical crosslinkers or one or more peptide linkers. Suitable chemical crosslinkers are well-known in the art. Suitable chemical crosslinkers include, but are not limited to, those including the following functional groups: maleimide, active esters, succinimide, azide, alkyne (such as dibenzocyclooctynol (DIBO or DBCO), difluoro cycloalkynes and linear alkynes), phosphine (such as those used in traceless and non-traceless Staudinger ligations), haloacetyl (such as iodoacetamide), phosgene type reagents, sulphonyl chloride reagents, isothiocyanates, acyl halides, hydrazines, disulphides, vinyl sulfones, aziridines and photoreactive reagents (such as aryl azides, diaziridines).

Reactions between amino acids and functional groups may be spontaneous, such as cysteine/maleimide, or may require external reagents, such as Cu(I) for linking azide and linear alkynes.

Preferred crosslinkers include 2,5-dioxopyrrolidin-1-yl 3-(pyridin-2-yldisulfanyl)propanoate, 2,5-dioxopyrrolidin-1-yl 4-(pyridin-2-yldisulfanyl)butanoate, 2,5-dioxopyrrolidin-1-yl 8-(pyridin-2-yldisulfanyl)octananoate, di-maleimide PEG 1k, di-maleimide PEG 3.4k, di-maleimide PEG 5k, di-maleimide PEG 10k, bis(maleimido)ethane (BMOE), bis-maleimidohexane (BMH), 1,4-bis-maleimidobutane (BMB), 1,4 bis-maleimidyl-2,3-dihydroxybutane (BMDB), BM[PEO]2 (1,8-bis-maleimidodiethyleneglycol), BM[PEO]3 (1,11-bis-maleimidotriethylene glycol), tris[2-maleimidoethyl]amine (TMEA), DTME dithiobismaleimidoethane, bis-maleimide PEG3, bis-maleimide PEG11, DBCO-maleimide, DBCO-PEG4-maleimide, DBCO-PEG4-NH2, DBCO-PEG4-NHS, DBCO-NHS, DBCO-PEG-DBCO 2.8 kDa, DBCO-PEG-DBCO 4.0 kDa, DBCO-15 atoms-DBCO, DBCO-26 atoms-DBCO, DBCO-35 atoms-DBCO, DBCO-PEG4-S-S-PEG3-biotin, DBCO-S-S-PEG3-biotin and DBCO-S-S-PEG11-biotin. The most preferred crosslinkers are succinimidyl 3-(2-pyridyldithio)propionate (SPDP) and maleimide-PEG(2 kDa)-maleimide (alpha,omega-bis-maleimido poly(ethylene glycol)).

The linkers may be labeled. Suitable labels include, but are not limited to, fluorescent molecules (such as Cy3, FAM/FITC or AlexaFluor®555), radioisotopes, e.g. $^{125}$I, $^{35}$S, enzymes, antibodies, antigens, polynucleotides and ligands such as biotin. Such labels allow the amount of linker to be quantified. The label could also be a cleavable purification tag, such as biotin, or a specific sequence to show up in an identification method, such as a peptide that is not present in the protein itself, but that is released by trypsin digestion.

Cross-linkage of analytes or microparticles to themselves may be prevented by keeping the concentration of linker in a vast excess of the analyte and/or microparticle. Alternatively, a "lock and key" arrangement may be used in which two linkers are used. Only one end of each linker may react together to form a longer linker and the other ends of the linker each react with a different part of the construct (i.e. analyte or microparticle).

The attachment of the analyte to the microparticle may be permanent or stable (i.e. the analyte does not become detached from the microparticle in the method of the invention). A preferred permanent or stable attachment is covalent attachment.

The attachment is preferably transient, i.e. the analyte may detach from the microparticle during the method of the invention, for instance once delivered to the pore or when interacting with the pore. A preferred transient attachment is via hybridisation. Two complementary polynucleotides may be used to attach the analyte to the microparticle. Alternatively, two polynucleotides each comprising a portion or region which specifically hybridises to or is complementary to a portion or region of the other polynucleotide may be used. One polynucleotide may be attached to the analyte and the other may be attached to the microparticle. The analyte and microparticle may then be attached by hybridisation of the two polynucleotides. The polynucleotides may be any of those discussed above. Alternatively, if the analyte is a polynucleotide, a polynucleotide which comprises a portion or region which specifically hybridises to or is complementary to a portion or region of the polynucleotide analyte may be attached to the microparticle.

This is discussed in more detail below with reference to coupling. Other preferred transient attachments include, but are not limited to, attachment using a polyhistidine-tag (hexa histidine-tag, 6×His-tag, His6 tag or His-tag®), Ni-NTA or streptavidin-biotin.

As discussed below, polynucleotide binding proteins, such as helicases, may be used to control the movement of polynucleotide analyte through the pore. In a preferred embodiment, the polynucleotide analyte is provided with a polynucleotide binding protein bound to it (i.e. the polynucleotide analyte comprises a polynucleotide binding protein) and the polynucleotide is attached to the microparticle via the polynucleotide binding protein. The polynucleotide binding protein may be attached to the microparticle using any of the methods discussed above. The polynucleotide binding protein may be any of the proteins discussed below. The polynucleotide binding protein is preferably derived from a helicase.

Delivery

The method comprises delivering the microparticle towards the membrane. The microparticle delivers the analyte to the transmembrane pore in the membrane. The microparticle may be delivered towards the membrane in any manner. The method preferably comprises positioning the microparticle near to or adjacent to the membrane and allowing the microparticle to move towards the membrane.

The microparticle may be positioned any distance from the membrane, for instance about 500 µm from the membrane or closer, about 200 µm from the membrane or closer, about 100 µm from the membrane or closer, about 50 µm from the membrane or closer or about 30 µm from the membrane or closer.

The microparticle moves towards the membrane. The microparticle typically moves to the membrane. The microparticle may contact the membrane. The microparticle does not have to contact the membrane. For instance, the microparticle may not contact the membrane if it is substantially or completely coated with analyte or if substantially all of or all of its surface is attached to the analyte. In some embodiments, the analyte, such as polynucleotide, may be larger or longer than the particle size of the microparticle. The analyte may act as a cushion between the microparticle and the membrane. The microparticle moves close enough to the membrane to deliver the analyte to the pore. The skilled person can design the system such that the analyte is delivered to the pore.

The microparticle may move towards the membrane in any manner. The method preferably comprises allowing the microparticle to move along an electrochemical gradient, diffusion gradient, hydrophilic gradient or hydrophobic gradient. A gradient is an increase or decrease in the magnitude of a property observed when passing from one point or moment to another. The skilled person will understand how to generate any of the gradients mentioned above and how to get a microparticle to move along them. For instance, a charged microparticle will typically move along an electrochemical gradient. A microparticle will typically diffuse towards the membrane. A microparticle will typically flow in solution along a pressure gradient. A hydrophilic or hydrophobic microparticle will typically move along a hydrophilic or hydrophobic gradient. The analyte and any associated molecule, such as the one or more anchors, may affect the charge and/or hydrophilicity/hydrophobicity of the microparticle.

The method preferably comprises allowing the microparticle to move within a magnetic field. The method preferably comprises using a magnetic field to deliver the microparticle to the membrane. Magnetic microparticles are discussed above. Suitable methods are known for creating magnetic fields and include, but are not limited to, magnetic materials or electromagnets.

The method preferably comprises allowing the microparticle to move within an electrical field. The method preferably comprises using an electrical field to deliver the microparticle to the membrane. Charged microparticles are known in the art and discussed above. Suitable methods are known for creating electrical fields also known.

The method preferably comprises allowing the microparticle to move under pressure. The method preferably comprises using pressure or flow to deliver the microparticle to the membrane. The pressure may be physical pressure or osmotic pressure. Suitable methods are known for creating such pressures.

The method preferably comprises allowing the microparticle to move within a gravitational field or with gravity. The method preferably comprises using gravity to deliver the microparticle to the membrane. A dense microparticle placed above a membrane in solution will move towards the membrane under the influence of gravity. The method may comprise allowing the microparticle to travel, move, slide or roll along a surface towards the membrane. The surface typically slopes away from the vertical walls of a chamber comprising the membrane (where the walls are approximately perpendicular to the plane of the membrane) at an angle of about 45° to about 69°. The surface typically slopes towards the membrane at an angle of about 21°, 22°, 23°, 24°, 25°, 26°, 27°, 28°, 29°, 30°, 31°, 32°, 33°, 34°, 35°, 36°, 37°, 38°, 39°, 40°, 41°, 42°, 43°, 44° to about 45° compared with the plane of the membrane. In a preferred embodiment, the sloping surface is formed by pre-treatment of one or more surfaces of a chamber comprising the membrane with a suitable pre-treatment, such as silicon oil, AR20 or hexadecane. Suitable apparatuses comprising chambers for use in the method of the invention are discussed below.

If the microparticle contacts the membrane, the method may comprise allowing the microparticle to travel, move, slide or roll along the membrane. If the microparticle does not contact the membrane, the method may comprise allowing the microparticle to travel, move, slide or roll in parallel with the membrane.

Coupling

The analyte preferably comprises one or more anchors which are capable of coupling to the membrane. The method preferably further comprises coupling the analyte to the membrane using the one or more anchors.

The anchor comprises a group which couples (or binds) to the analyte and a group which couples (or binds) to the membrane. Each anchor may covalently couple (or bind) to the analyte and/or the membrane.

The analyte may be coupled to the membrane using any number of anchors, such as 2, 3, 4 or more anchors. For instance, the analyte may be coupled to the membrane using two anchors each of which separately couples (or binds) to both the analyte and membrane.

The one or more anchors may comprise one or more polynucleotide binding proteins. Each anchor may comprise one or more polynucleotide binding proteins. The polynucleotide binding protein(s) may be any of those discussed below.

If the membrane is an amphiphilic layer, such as a triblock copolymer membrane, the one or more anchors preferably comprise a polypeptide anchor present in the membrane and/or a hydrophobic anchor present in the membrane. The hydrophobic anchor is preferably a lipid, fatty acid, sterol, carbon nanotube, polypeptide, protein or amino acid, for example cholesterol, palmitate or tocopherol. In preferred embodiments, the one or more anchors are not the pore.

The components of the membrane, such as the amphiphilic molecules, copolymer or lipids, may be chemically-modified or functionalised to form the one or more anchors. Examples of suitable chemical modifications and suitable ways of functionalising the components of the membrane are discussed in more detail below. Any proportion of the membrane components may be functionalised, for example at least 0.01%, at least 0.1%, at least 1%, at least 10%, at least 25%, at least 50% or 100%.

The analyte may be coupled directly to the membrane. The one or more anchors used to couple the analyte to the membrane preferably comprise a linker. The one or more anchors may comprise one or more, such as 2, 3, 4 or more, linkers. One linker may be used to couple more than one, such as 2, 3, 4 or more, analytes to the membrane.

Preferred linkers include, but are not limited to, polymers, such as polynucleotides, polyethylene glycols (PEGs), polysaccharides and polypeptides. These linkers may be linear, branched or circular. For instance, the linker may be a circular polynucleotide. If the analyte is itself a polynucleotide, it may hybridise to a complementary sequence on the circular polynucleotide linker.

The one or more anchors or one or more linkers may comprise a component that can be cut or broken down, such as a restriction site or a photolabile group.

Functionalised linkers and the ways in which they can couple molecules are known in the art. For instance, linkers functionalised with maleimide groups will react with and attach to cysteine residues in proteins. In the context of this invention, the protein may be present in the membrane, may be the analyte itself or may be used to couple (or bind) to the analyte. This is discussed in more detail below.

Crosslinkage of analytes can be avoided using a "lock and key" arrangement. Only one end of each linker may react together to form a longer linker and the other ends of the linker each react with the analyte or membrane respectively. Such linkers are described in International Application No. PCT/GB10/000132 (published as WO 2010/086602).

The use of a linker is preferred in the sequencing embodiments discussed below. If a polynucleotide analyte is permanently coupled directly to the membrane in the sense that it does not uncouple when interacting with the pore, then some sequence data will be lost as the sequencing run cannot continue to the end of the polynucleotide due to the distance between the membrane and the pore. If a linker is used, then the polynucleotide analyte can be processed to completion.

The coupling may be permanent or stable. In other words, the coupling may be such that the analyte remains coupled to the membrane when interacting with the pore.

The coupling may be transient. In other words, the coupling may be such that the analyte may decouple from the membrane when interacting with the pore. For certain applications, such as aptamer detection and polynucleotide sequencing, the transient nature of the coupling is preferred. If a permanent or stable linker is attached directly to either the 5' or 3' end of a polynucleotide and the linker is shorter than the distance between the membrane and the transmembrane pore's channel, then some sequence data will be lost as the sequencing run cannot continue to the end of the polynucleotide. If the coupling is transient, then when the coupled end randomly becomes free of the membrane, then the polynucleotide can be processed to completion. Chemical groups that form permanent/stable or transient links are discussed in more detail below. The analyte may be transiently coupled to an amphiphilic layer or triblock copolymer membrane using cholesterol or a fatty acyl chain. Any fatty acyl chain having a length of from 6 to 30 carbon atom, such as hexadecanoic acid, may be used.

In preferred embodiments, a polynucleotide analyte, such as a nucleic acid, is coupled to an amphiphilic layer such as a triblock copolymer membrane or lipid bilayer. Coupling of nucleic acids to synthetic lipid bilayers has been carried out previously with various different tethering strategies. These are summarised in Table 3 below.

TABLE 3

| Anchor comprising | Type of coupling | Reference |
|---|---|---|
| Thiol | Stable | Yoshina-Ishii, C. and S. G. Boxer (2003). "Arrays of mobile tethered vesicles on supported lipid bilayers." *J Am Chem Soc* 125(13): 3696-7. |
| Biotin | Stable | Nikolov, V., R. Lipowsky, et al. (2007). "Behavior of giant vesicles with anchored DNA molecules." *Biophys J* 92(12): 4356-68 |
| Cholesterol | Transient | Pfeiffer, I. and F. Hook (2004). "Bivalent cholesterol-based coupling of oligoncletides to lipid membrane assemblies." *J Am Chem Soc* 126(33): 10224-5 |

TABLE 3-continued

| Anchor comprising | Type of coupling | Reference |
|---|---|---|
| Surfactant (e.g. Lipid, Palmitate, etc) | Stable | van Lengerich, B., R. J. Rawle, et al. "Covalent attachment of lipid vesicles to a fluid-supported bilayer allows observation of DNA-mediated vesicle interactions." *Langmuir* 26(11): 8666-72 |

Synthetic polynucleotide analytes and/or linkers may be functionalised using a modified phosphoramidite in the synthesis reaction, which is easily compatible for the direct addition of suitable anchoring groups, such as cholesterol, tocopherol, palmitate, thiol, lipid and biotin groups. These different attachment chemistries give a suite of options for attachment to polynucleotides. Each different modification group couples the polynucleotide in a slightly different way and coupling is not always permanent so giving different dwell times for the analyte to the membrane. The advantages of transient coupling are discussed above.

Coupling of polynucleotides to a linker or to a functionalised membrane can also be achieved by a number of other means provided that a complementary reactive group or an anchoring group can be added to the polynucleotide. The addition of reactive groups to either end of a polynucleotide has been reported previously. A thiol group can be added to the 5' of ssDNA or dsDNA using T4 polynucleotide kinase and ATPγS (Grant, G. P. and P. Z. Qin (2007). "A facile method for attaching nitroxide spin labels at the 5' terminus of nucleic acids." *Nucleic Acids Res* 35(10): e77). An azide group can be added to the 5'-phosphate of ssDNA or dsDNA using T4 polynucleotide kinase and γ-[2-Azidoethyl]-ATP or γ-[6-Azidohexyl]-ATP. Using thiol or Click chemistry a tether, containing either a thiol, iodoacetamide OPSS or maleimide group (reactive to thiols) or a DIBO (dibenzocyclooxtyne) or alkyne group (reactive to azides), can be covalently attached to the analyte. A more diverse selection of chemical groups, such as biotin, thiols and fluorophores, can be added using terminal transferase to incorporate modified oligonucleotides to the 3' of ssDNA (Kumar, A., P. Tchen, et al. (1988). "Nonradioactive labeling of synthetic oligonucleotide probes with terminal deoxynucleotidyl transferase." *Anal Biochem* 169(2): 376-82). Streptavidin/biotin and/or streptavidin/desthiobiotin coupling may be used for any other analyte. The Examples below describes how a polynucleotide can be coupled to a membrane using streptavidin/biotin and streptavidin/desthiobiotin. It may also be possible that anchors may be directly added to polynucleotides using terminal transferase with suitably modified nucleotides (e.g. cholesterol or palmitate).

The one or more anchors preferably couple the analyte to the membrane via hybridisation. The hybridisation may be present in any part of the one or more anchors, such as between the one or more anchors and the analyte, within the one or more anchors or between the one or more anchors and the membrane. Hybridisation in the one or more anchors allows coupling in a transient manner as discussed above. For instance, a linker may comprise two or more polynucleotides, such as 3, 4 or 5 polynucleotides, hybridised together. If the analyte is a polynucleotide, the one or more anchors may hybridise to the polynucleotide analyte. The one or more anchors may hybridise directly to the polynucleotide analyte, directly to a Y adaptor and/or leader sequence attached to the polynucleotide analyte or directly to a hairpin loop adaptor attached to the polynucleotide analyte (as discussed in more detail below). Alternatively, the one or more anchors may be hybridised to one or more, such as 2 or 3, intermediate polynucleotides (or "splints") which are hybridised to the polynucleotide analyte, to a Y adaptor and/or leader sequence attached to the polynucleotide analyte or to a hairpin loop adaptor attached to the polynucleotide analyte (as discussed in more detail below).

The one or more anchors may comprise a single stranded or double stranded polynucleotide. One part of the anchor may be ligated to a single stranded or double stranded polynucleotide analyte. Ligation of short pieces of ssDNA have been reported using T4 RNA ligase I (Troutt, A. B., M. G. McHeyzer-Williams, et al. (1992). "Ligation-anchored PCR: a simple amplification technique with single-sided specificity." Proc Natl Acad Sci USA 89(20): 9823-5). Alternatively, either a single stranded or double stranded polynucleotide can be ligated to a double stranded polynucleotide analyte and then the two strands separated by thermal or chemical denaturation. To a double stranded polynucleotide, it is possible to add either a piece of single stranded polynucleotide to one or both of the ends of the duplex, or a double stranded polynucleotide to one or both ends. For addition of single stranded polynucleotides to the double stranded polynucleotide, this can be achieved using T4 RNA ligase I as for ligation to other regions of single stranded polynucleotides. For addition of double stranded polynucleotides to a double stranded polynucleotide analyte then ligation can be "blunt-ended", with complementary 3' dA/dT tails on the analyte and added polynucleotide respectively (as is routinely done for many sample prep applications to prevent concatemer or dimer formation) or using "sticky-ends" generated by restriction digestion of the analyte and ligation of compatible adapters. Then, when the duplex is melted, each single strand will have either a 5' or 3' modification if a single stranded polynucleotide was used for ligation or a modification at the 5' end, the 3' end or both if a double stranded polynucleotide was used for ligation.

If the polynucleotide analyte is a synthetic strand, the one or more anchors can be incorporated during the chemical synthesis of the polynucleotide. For instance, the polynucleotide can be synthesised using a primer having a reactive group attached to it.

Adenylated polynucleotides are intermediates in ligation reactions, where an adenosine-monophosphate is attached to the 5'-phosphate of the polynucleotide. Various kits are available for generation of this intermediate, such as the 5' DNA Adenylation Kit from NEB. By substituting ATP in the reaction for a modified nucleotide triphosphate, then addition of reactive groups (such as thiols, amines, biotin, azides, etc) to the 5' of a polynucleotide can be possible. It may also be possible that anchors could be directly added to polynucleotides using a 5' DNA adenylation kit with suitably modified nucleotides (e.g. cholesterol or palmitate).

A common technique for the amplification of sections of genomic DNA is using polymerase chain reaction (PCR). Here, using two synthetic oligonucleotide primers, a number of copies of the same section of DNA can be generated, where for each copy the 5' of each strand in the duplex will be a synthetic polynucleotide. Single or multiple nucleotides can be added to 3' end of single or double stranded DNA by employing a polymerase. Examples of polymerases which could be used include, but are not limited to, Terminal Transferase, Klenow and E. coli Poly(A) polymerase). By substituting ATP in the reaction for a modified nucleotide triphosphate then anchors, such as a cholesterol, thiol, amine, azide, biotin or lipid, can be incorporated into double stranded polynucleotides. Therefore, each copy of the amplified polynucleotide will contain an anchor.

Ideally, the analyte is coupled to the membrane without having to functionalise the analyte. This can be achieved by coupling the one or more anchors, such as a polynucleotide binding protein or a chemical group, to the membrane and allowing the one or more anchors to interact with the analyte or by functionalizing the membrane. The one or more anchors may be coupled to the membrane by any of the methods described herein. In particular, the one or more anchors may comprise one or more linkers, such as maleimide functionalised linkers.

In this embodiment, the analyte is typically RNA, DNA, PNA, TNA or LNA and may be double or single stranded. This embodiment is particularly suited to genomic DNA analytes.

The one or more anchors can comprise any group that couples to, binds to or interacts with single or double stranded polynucleotides, specific nucleotide sequences within the analyte or patterns of modified nucleotides within the analyte, or any other ligand that is present on the polynucleotide.

Suitable binding proteins for use in anchors include, but are not limited to, E. coli single stranded binding protein, P5 single stranded binding protein, T4 gp32 single stranded binding protein, the TOPO V dsDNA binding region, human histone proteins, E. coli HU DNA binding protein and other archaeal, prokaryotic or eukaryotic single stranded or double stranded polynucleotide (or nucleic acid) binding proteins, including those listed below.

The specific nucleotide sequences could be sequences recognised by transcription factors, ribosomes, endonucleases, topoisomerases or replication initiation factors. The patterns of modified nucleotides could be patterns of methylation or damage.

The one or more anchors can comprise any group which couples to, binds to, intercalates with or interacts with a polynucleotide analyte. The group may intercalate or interact with the polynucleotide analyte via electrostatic, hydrogen bonding or Van der Waals interactions. Such groups include a lysine monomer, poly-lysine (which will interact with ssDNA or dsDNA), ethidium bromide (which will intercalate with dsDNA), universal bases or universal nucleotides (which can hybridise with any polynucleotide analyte) and osmium complexes (which can react to methylated bases). A polynucleotide analyte may therefore be coupled to the membrane using one or more universal nucleotides attached to the membrane. Each universal nucleotide may be coupled to the membrane using one or more linkers. The universal nucleotide preferably comprises one of the following nucleobases: hypoxanthine, 4-nitroindole, 5-nitroindole, 6-nitroindole, formylindole, 3-nitropyrrole, nitroimidazole, 4-nitropyrazole, 4-nitrobenzimidazole, 5-nitroindazole, 4-aminobenzimidazole or phenyl (C6-aromatic ring). The universal nucleotide more preferably comprises one of the following nucleosides: 2'-deoxyinosine, inosine, 7-deaza-2'-deoxyinosine, 7-deaza-inosine, 2-aza-deoxyinosine, 2-aza-inosine, 2-O'-methylinosine, 4-nitroindole 2'-deoxyribonucleoside, 4-nitroindole ribonucleoside, 5-nitroindole 2'-deoxyribonucleoside, 5-nitroindole ribonucleoside, 6-nitroindole 2'-deoxyribonucleoside, 6-nitroindole ribonucleoside, 3-nitropyrrole 2'-deoxyribonucleoside, 3-nitropyrrole ribonucleoside, an acyclic sugar analogue of hypoxanthine, nitroimidazole 2'-deoxyribonucleoside, nitroimidazole ribonucleoside, 4-nitropyrazole 2'-deoxyribonucleoside, 4-nitropyrazole ribonucleoside, 4-nitrobenzimidazole 2'-deoxyribonucleoside, 4-nitrobenzimidazole ribonucleoside, 5-nitroindazole 2'-deoxyribonucleoside, 5-nitroindazole ribonucleoside, 4-aminobenzimidazole 2'-deoxyribonucleoside, 4-aminobenzimidazole ribonucleoside, phenyl C-ribonucleoside, phenyl C-2'-deoxyribosyl nucleoside, 2'-deoxynebularine, 2'-deoxyisoguanosine, K-2'-deoxyribose, P-2'-deoxyribose and pyrrolidine. The universal nucleotide more preferably comprises 2'-deoxyinosine. The universal nucleotide is more preferably IMP or dIMP. The universal nucleotide is most preferably dPMP (2'-Deoxy-P-nucleoside monophosphate) or dKMP (N6-methoxy-2,6-diaminopurine monophosphate).

The one or more anchors may couple to (or bind to) the polynucleotide analyte via Hoogsteen hydrogen bonds (where two nucleobases are held together by hydrogen bonds) or reversed Hoogsteen hydrogen bonds (where one nucleobase is rotated through 180° with respect to the other nucleobase). For instance, the one or more anchors may comprise one or more nucleotides, one or more oligonucleotides or one or more polynucleotides which form Hoogsteen hydrogen bonds or reversed Hoogsteen hydrogen bonds with the polynucleotide analyte. These types of hydrogen bonds allow a third polynucleotide strand to wind around a double stranded helix and form a triplex. The one or more anchors may couple to (or bind to) a double stranded polynucleotide analyte by forming a triplex with the double stranded duplex.

In this embodiment at least 1%, at least 10%, at least 25%, at least 50% or 100% of the membrane components may be functionalised.

Where the one or more anchors comprise a protein, they may be able to anchor directly into the membrane without further functonalisation, for example if it already has an external hydrophobic region which is compatible with the membrane. Examples of such proteins include, but are not limited to, transmembrane proteins, intramembrane proteins and membrane proteins. Alternatively the protein may be expressed with a genetically fused hydrophobic region which is compatible with the membrane. Such hydrophobic protein regions are known in the art.

The one or more anchors are preferably mixed with the analyte before delivery to the membrane, but the one or more anchors may be contacted with the membrane and subsequently contacted with the analyte.

In another aspect the analyte may be functionalised, using methods described above, so that it can be recognised by a specific binding group. Specifically the analyte may be functionalised with a ligand such as biotin (for binding to streptavidin), amylose (for binding to maltose binding protein or a fusion protein), Ni-NTA (for binding to polyhistidine or poly-histidine tagged proteins) or a peptides (such as an antigen).

According to a preferred embodiment, the one or more anchors may be used to couple a polynucleotide analyte to the membrane when the analyte is attached to a leader sequence which preferentially threads into the pore. Leader sequences are discussed in more detail below. Preferably, the polynucleotide analyte is attached (such as ligated) to a leader sequence which preferentially threads into the pore. Such a leader sequence may comprise a homopolymeric polynucleotide or an abasic region. The leader sequence is typically designed to hybridise to the one or more anchors either directly or via one or more intermediate polynucleotides (or splints). In such instances, the one or more anchors typically comprise a polynucleotide sequence which is complementary to a sequence in the leader sequence or a sequence in the one or more intermediate polynucleotides (or splints). In such instances, the one or more splints typically comprise a polynucleotide sequence which is complementary to a sequence in the leader sequence.

Any of the methods discussed above for coupling polynucleotides to membranes, such as amphiphilic layers, can of course be applied to other analyte and membrane combinations. In some embodiments, an amino acid, peptide, polypeptide or protein is coupled to an amphiphilic layer, such as a triblock copolymer layer or lipid bilayer. Various methodologies for the chemical attachment of such analytes are available. An example of a molecule used in chemical attachment is EDC (1-ethyl-3-[3-dimethylaminopropyl]carbodiimide hydrochloride). Reactive groups can also be added to the 5' of polynucleotides using commercially available kits (Thermo Pierce, Part No. 22980). Suitable methods include, but are not limited to, transient affinity attachment using histidine residues and Ni-NTA, as well as more robust covalent attachment by reactive cysteines, lysines or non natural amino acids.

Analyte Characterisation

The invention may further concern determining the presence, absence or one or more characteristics of the analyte using the transmembrane pore. This typically involves (i) allowing the analyte to interact with the transmembrane pore and (ii) taking one or more measurements during the interaction, wherein the measurements are indicative of the presence, absence or one or more characteristics of the analyte.

A variety of different types of measurements may be made. This includes without limitation: electrical measurements and optical measurements. Possible electrical measurements include: current measurements, impedance measurements, tunnelling measurements (Ivanov A P et al., Nano Lett. 2011 Jan. 12; 11(1):279-85), and FET measurements (International Application WO 2005/124888). Optical measurements may be combined with electrical measurements (Soni G V et al., Rev Sci Instrum. 2010 January; 81(1):014301). The measurement may be a transmembrane current measurement such as measurement of ionic current flowing through the pore.

Electrical measurements may be made using standard single channel recording equipment as describe in Stoddart D et al., Proc Natl Acad Sci, 12; 106(19):7702-7, Lieberman K R et al, J Am Chem Soc. 2010; 132(50):17961-72, and International Application WO 2000/28312. Alternatively, electrical measurements may be made using a multi-channel system, for example as described in International Application WO 2009/077734 and International Application WO 2011/067559.

The method is preferably carried out with a potential applied across the membrane. The applied potential may be a voltage potential. Alternatively, the applied potential may be a chemical potential. An example of this is using a salt gradient across a membrane, such as an amphiphilic layer. A salt gradient is disclosed in Holden et al., J Am Chem Soc. 2007 Jul. 11; 129(27):8650-5. In some instances, the current passing through the pore as a polynucleotide analyte moves with respect to the pore is used to estimate or determine the sequence of the polynucleotide. This is strand sequencing.

The method preferably comprises (i) allowing the analyte to interact with the pore and (ii) measuring the current passing through the pore during the interaction and thereby determining the presence, absence or one or more characteristics of the analyte.

The analyte is present if the current flows through the pore in a manner specific for the analyte (i.e. if a distinctive current associated with the analyte is detected flowing through the pore). The analyte is absent if the current does not flow through the pore in a manner specific for the analyte. Similarly, the characteristics of the analyte can be determined using the current flowing through the pore during the interaction.

The invention therefore involves nanopore sensing of an analyte. The invention can be used to differentiate analytes of similar structure on the basis of the different effects they have on the current passing through the pore. The invention can also be used to measure the concentration of a particular analyte in a sample.

The invention may also be used in a sensor that uses many or thousands of pores in bulk sensing applications.

During the interaction between the analyte and the pore, the analyte affects the current flowing through the pore in a manner specific for that analyte. For example, a particular analyte will reduce the current flowing through the pore for a particular mean time period and to a particular extent. In other words, the current flowing through the pore is distinctive for a particular analyte. Control experiments may be carried out to determine the effect a particular analyte has on the current flowing through the pore. Results from carrying out the method of the invention on a test sample can then be compared with those derived from such a control experiment in order to identify a particular analyte in the sample, determine whether a particular analyte is present in the sample or determine the characteristics of each analyte. The frequency at which the current flowing through the pore is affected in a manner indicative of a particular analyte can be used to determine the concentration of that analyte in the sample.

Uncoupling

The method of the invention may involve uncoupling the analyte from the membrane. If multiple analytes are being delivered using the method of the invention, at least 10% of the analyte is preferably uncoupled from the membrane. For instance, at least 20%, at least 30%, at least 40%, at least 50%, at least 60%, at least 70%, at least 80% at least 90% or at least 95% of the analyte may be uncoupled from the membrane. Preferably, all of the analyte is uncoupled from the membrane. The amount of the analyte uncoupled from the membrane can be determined using the pore.

The analyte can be uncoupled from the membrane using any known method. The analyte is preferably not uncoupled from the membrane using the pore. The analyte is preferably not uncoupled from the membrane using a voltage or an applied potential.

The method preferably further comprises uncoupling the analyte from the membrane by removing the one or more anchors from the membrane. The method more preferably comprises contacting the one or more anchors with an agent which has a higher affinity for the one or more anchors than the one or more anchors have for the membrane. A variety of protocols for competitive binding or immunoradiometric assays to determine the specific binding capability of molecules are well known in the art (see for example Maddox et al, *J. Exp. Med.* 158, 1211-1226, 1993). The agent removes the one or more anchors from the membrane and thereby uncouples the analyte. The agent is preferably a sugar. Any sugar which binds to the one or more anchors with a higher affinity than the one or more anchors have for the membrane may be used. The sugar may be a cyclodextrin or derivative thereof as discussed below.

The one or more anchors preferably comprise a hydrophobic anchor, such as cholesterol, and the agent is preferably a cyclodextrin or a derivative thereof or a lipid. The cyclodextrin or derivative thereof may be any of those disclosed in Eliseev, A. V., and Schneider, H-J. (1994) *J. Am. Chem. Soc.* 116, 6081-6088. The agent is more preferably heptakis-6-amino-β-cyclodextrin ($am_7$-βCD), 6-monodeoxy-6-monoamino-β-cyclodextrin ($am_1$-βCD) or heptakis-(6-deoxy-6-guanidino)-cyclodextrin ($gu_7$-βCD). Any of the lipids disclosed herein may be used.

The one or more anchors preferably comprise streptavidin, biotin or desthiobiotin and the agent is preferably biotin, desthiobiotin or streptavidin. Both biotin and desthiobiotin bind to streptavidin with a higher affinity than streptavidin binds to the membrane and vice versa. Biotin has a stronger affinity for streptavidin than desthiobiotin. An anchor comprising streptavidin may therefore be removed from the membrane using biotin or desthiobiotin and vice versa.

The one or more anchors preferably comprise a protein and the agent is preferably an antibody or fragment thereof which specifically binds to the protein. An antibody specifically binds to a protein if it binds to the protein with preferential or high affinity, but does not bind or binds with only low affinity to other or different proteins. An antibody binds with preferential or high affinity if it binds with a Kd of $1 \times 10^{-6}$ M or less, more preferably $1 \times 10^{-7}$ M or less, $5 \times 10^{-8}$ M or less, more preferably $1 \times 10^{-8}$ M or less or more preferably $5 \times 10^{-9}$ M or less. An antibody binds with low affinity if it binds with a Kd of $1 \times 10^{-6}$ M or more, more preferably $1 \times 10^{-5}$ M or more, more preferably $1 \times 10^{-4}$ M or more, more preferably $1 \times 10^{-3}$ M or more, even more preferably $1 \times 10^{-2}$ M or more. Any method may be used to detect binding or specific binding. Methods of quantitatively measuring the binding of an antibody to a protein are well known in the art. The antibody may be a monoclonal antibody or a polyclonal antibody. Suitable fragments of antibodies include, but are not limited to, Fv, F(ab') and F(ab')$_2$ fragments, as well as single chain antibodies. Furthermore, the antibody or fragment thereof may be a chimeric antibody or fragment thereof, a CDR-grafted antibody or fragment thereof or a humanised antibody or fragment thereof.

The method may comprise contacting the one or more anchors with an agent which reduces their ability to couple to the membrane. For instance, the agent could interfere with the structure and/or hydrophobicity of the one or more anchors and thereby reduce their ability to couple to the membrane. The one or more anchors preferably comprise cholesterol and the agent is preferably cholesterol dehydrogenase. The one or more anchors preferably comprise a lipid and the agent is preferably a phospholipase. The one or more anchors preferably comprise a protein and the agent is preferably a proteinase or urea. Other combination of suitable anchors and agents will be clear to a person skilled in the art.

The method may comprise uncoupling the analyte from the membrane by separating the analyte from the one or more anchors. This can be done in any manner. For instance, the linker could be cut in one or more anchors comprising a linker. This embodiment is particularly applicable to one or more anchors which involve linkage via hybridisation. Such anchors are discussed above.

The method may comprise uncoupling the analyte from the membrane by contacting the analyte and the one or more anchors with an agent which competes with the analyte for binding to the one or more anchors. Methods for determining and measuring competitive binding are known in the art. The agent is preferably a polynucleotide which competes with the analyte for hybridisation to the one or more anchors. For instance, if the analyte is coupled to the membrane using one or more anchors which involve hybridisation, the analyte can be uncoupled by contacting the one or more anchors with a polynucleotide which also hybridises to the site of hybridisation. The polynucleotide agent is typically added at a concentration that is higher than the concentration of the analyte and one or more anchors. Alternatively, the polynucleotide agent may hybridise more strongly to the one or more anchors than the analyte.

The method may comprise (i) contacting the analyte and the one or more anchors with urea, tris(2-carboxyethyl) phosphine (TCEP), dithiothreitol (DTT), streptavidin or biotin, UV light, an enzyme or a binding agent; (ii) heating the analyte and one or more anchors; or (iii) altering the pH. Urea, tris(2-carboxyethyl)phosphine (TCEP) or dithiothreitol (DTT) are capable of disrupting anchors and separating the analyte from the membrane. If an anchor comprises a streptavidin-biotin link, then a streptavidin agent will compete for binding to the biotin. If an anchor comprises a streptavidin-desthiobiotin link, then a biotin agent will compete for binding to the streptavidin. UV light can be used to breakdown photolabile groups. Enzymes and binding agents can be used to cut, breakdown or unravel the anchor. Preferred enzymes include, but are not limited to, an exonuclease, an endonuclease or a helicase. Preferred binding agents include, but are not limited to, an enzyme, an antibody or a fragment thereof or a single-stranded binding protein (SSB). Any of the enzymes discussed below or antibodies discussed above may be used. Heat and pH can be used to disrupt hybridisation and other linkages.

If the analyte is uncoupled from the membrane by separating the analyte from the one or more anchors, the one or more anchors will remain in the membrane. The remaining one or more anchors may be used to couple another analyte delivered to the membrane. For instance, a second analyte may also be delivered with a polynucleotide which hybridises to the one or more anchors that remain in the membrane. Alternatively, a second analyte may be coupled to the membrane using separate one or more anchors from the ones separated from the first analyte (i.e. other one or more anchors). The separate one or more anchors may be the same type of anchor used to couple the first analyte to the membrane or may be a different type of anchor.

The method preferably further comprises uncoupling the analyte from the membrane by removing the microparticle from the membrane. Methods for removing the microparticle from the membrane are discussed below. If the strength of attachment of the analyte to the microparticle is greater than the strength of coupling of the analyte to the membrane, the removal of the microparticle will uncouple the analyte from the membrane. Strength of attachment and coupling can be measured as discussed below. Uncoupling of the analyte using the microparticle may help to remove all instances of the analyte from the system so that another microparticle may be used to deliver a second analyte (which may be the same as or different from the first analyte) to the transmembrane pore.

Removal or Washing

The method preferably further comprises removing the microparticle from the membrane. If multiple microparticles are used, at least 10% of the microparticles may be removed, such as at least 20%, at least 30%, at least 40%, at least 50%, at least 60%, at least 70%, at least 80% or at least 90% of the microparticles may be removed. The method more preferably further comprises removing all of the microparticles from the membrane. This can be done in any way. The microparticle may be removed from the membrane using a magnetic field. Alternatively or additionally, the microparticle may be removed from the membrane using a flow-based method. For instance, the membrane can be washed with a buffer. Suitable buffers are discussed below.

The method preferably comprises:
(a) providing a first analyte in a first sample attached to a first microparticle;
(b) delivering the first microparticle towards the membrane and thereby delivering the first analyte to the transmembrane pore;
(c) removing the first microparticle from the membrane;
(d) providing a second analyte in a second sample attached to a second microparticle;
(e) delivering the second microparticle towards the membrane and thereby delivering the second analyte to the transmembrane pore.

The first analyte may be the same as the second analyte. If the two analytes are polynucleotides, this will allow proof reading. The first analyte may be different from the second analyte, such as in type (e.g. protein and polynucleotide) and/or identity (e.g. two different polynucleotides). The two samples may be the same or different.

In one embodiment, the method preferably further comprises (i) between steps (b) and (c) allowing the first analyte to interact with the transmembrane pore and taking one or more measurements during the interaction, wherein the measurements are indicative of the presence, absence or one or more characteristics of the first analyte and/or (ii) after step (e) allowing the second analyte to interact with the transmembrane pore and taking one or more measurements during the interaction, wherein the measurements are indicative of the presence, absence or one or more characteristics of the second analyte.

In another embodiment, the first and second analytes are polynucleotides and the method further comprises (i) between steps (b) and (c) allowing the first polynucleotide to interact with the transmembrane pore such that the first polynucleotide moves through the pore and taking one or more measurements as the first polynucleotide moves with respect to the pore, wherein the measurements are indicative of one or more characteristics of the first polynucleotide, and thereby characterising the first polynucleotide and/or (ii) after step (e) allowing the second polynucleotide to interact with the transmembrane pore such that the second polynucleotide moves through the pore and taking one or more measurements as the second polynucleotide moves with respect to the pore, wherein the measurements are indicative of one or more characteristics of the second polynucleotide, and thereby characterising the second polynucleotide Step (c) in the removal method preferably comprises removing the microparticle and the first analyte.

Polynucleotide Characterisation

The method of the invention preferably involves characterising a polynucleotide. The polynucleotide is delivered to the transmembrane pore using the invention and the pore is used to characterise the polynucleotide.

After delivery, the method comprises (i) allowing the polynucleotide to interact with the transmembrane pore such that the polynucleotide moves through the pore and (ii) taking one or more measurements as the polynucleotide moves with respect to the pore, wherein the measurements are indicative of one or more characteristics of the polynucleotide, and thereby characterising the polynucleotide.

Any number of polynucleotides can be investigated. For instance, the method of the invention may concern characterising two or more polynucleotides, such as 3 or more, 4 or more, 5 or more, 6 or more, 7 or more, 8 or more, 9 or more, 10 or more, 20 or more, 30 or more, 50 or more, 100 or more, 500 or more, 1,000 or more, 5,000 or more, 10,000 or more, 100,000 or more, 1000,000 or more or 5000,000 or more, polynucleotides. The two or more polynucleotides may be delivered using the same microparticle or different microparticles.

If two or more polynucleotides are characterised, they may be different from one another. The two or more polynucleotides may be two or more instances of the same polynucleotide. This allows proof reading.

The polynucleotides can be naturally occurring or artificial. For instance, the method may be used to verify the sequence of two or more manufactured oligonucleotides. The methods are typically carried out in vitro.

The method may involve measuring two, three, four or five or more characteristics of each polynucleotide. The one or more characteristics are preferably selected from (i) the length of the polynucleotide, (ii) the identity of the polynucleotide, (iii) the sequence of the polynucleotide, (iv) the secondary structure of the polynucleotide and (v) whether or not the polynucleotide is modified. Any combination of (i) to (v) may be measured in accordance with the invention, such as {i}, {ii}, {iii}, {iv}, {v}, {i,ii}, {i,iii}, {i,iv}, {i,v}, {ii,iii}, {ii,iv}, {ii,v}, {iii,iv}, {iii,v}, {iv,v}, {i,ii,iv}, {i,ii,v}, {i,iii,iv}, {i,iii,v}, {i,iv,v}, {ii,iii,iv}, {ii,iii,v}, {ii,iv,v}, {iii,iv,v}, {i,ii,iii,iv}, {i,ii,iii,v}, {i,ii,iv,v}, {i,iii,iv,v}, {ii,iii,iv,v} or {i,ii,iii,iv,v}.

For (i), the length of the polynucleotide may be measured for example by determining the number of interactions between the polynucleotide and the pore or the duration of interaction between the polynucleotide and the pore.

For (ii), the identity of the polynucleotide may be measured in a number of ways. The identity of the polynucleotide may be measured in conjunction with measurement of the sequence of the polynucleotide or without measurement of the sequence of the polynucleotide. The former is straightforward; the polynucleotide is sequenced and thereby identified. The latter may be done in several ways. For instance, the presence of a particular motif in the polynucleotide may be measured (without measuring the remaining sequence of the polynucleotide). Alternatively, the measurement of a particular electrical and/or optical signal in the method may identify the polynucleotide as coming from a particular source.

For (iii), the sequence of the polynucleotide can be determined as described previously. Suitable sequencing methods, particularly those using electrical measurements, are described in Stoddart D et al., Proc Natl Acad Sci, 12; 106(19):7702-7, Lieberman K R et al, J Am Chem Soc. 2010; 132(50):17961-72, and International Application WO 2000/28312.

For (iv), the secondary structure may be measured in a variety of ways. For instance, if the method involves an electrical measurement, the secondary structure may be measured using a change in dwell time or a change in current flowing through the pore. This allows regions of single-stranded and double-stranded polynucleotide to be distinguished.

For (v), the presence or absence of any modification may be measured. The method preferably comprises determining whether or not the polynucleotide is modified by methylation, by oxidation, by damage, with one or more proteins or with one or more labels, tags or spacers. Specific modifications will result in specific interactions with the pore which can be measured using the methods described below. For instance, methylcyotsine may be distinguished from cytosine on the basis of the current flowing through the pore during its interaction with each nucleotide.

The methods may be carried out using any apparatus that is suitable for investigating a membrane/pore system in which a pore is present in a membrane. The method may be carried out using any apparatus that is suitable for trans-membrane pore sensing. For example, the apparatus comprises a chamber comprising an aqueous solution and a barrier that separates the chamber into two sections. The barrier typically has an aperture in which the membrane containing the pore is formed. Alternatively the barrier forms the membrane in which the pore is present.

The methods may be carried out using the apparatus described in International Application No. PCT/GB08/000562 (WO 2008/102120).

The methods may involve measuring the current passing through the pore as the polynucleotide moves with respect to the pore. Therefore the apparatus may also comprise an electrical circuit capable of applying a potential and measuring an electrical signal across the membrane and pore. The methods may be carried out using a patch clamp or a voltage clamp. The methods preferably involve the use of a voltage clamp.

The methods of the invention may involve the measuring of a current passing through the pore as the polynucleotide moves with respect to the pore. Suitable conditions for measuring ionic currents through transmembrane protein pores are known in the art and disclosed in the Example. The method is typically carried out with a voltage applied across the membrane and pore. The voltage used is typically from +5 V to −5 V, such as from +4 V to −4 V, +3 V to −3 V or +2 V to −2 V. The voltage used is typically from −600 mV to +600 mV or −400 mV to +400 mV. The voltage used is preferably in a range having a lower limit selected from −400 mV, −300 mV, −200 mV, −150 mV, −100 mV, −50 mV, −20 mV and 0 mV and an upper limit independently selected from +10 mV, +20 mV, +50 mV, +100 mV, +150 mV, +200 mV, +300 mV and +400 mV. The voltage used is more preferably in the range 100 mV to 240 mV and most preferably in the range of 120 mV to 220 mV. It is possible to increase discrimination between different nucleotides by a pore by using an increased applied potential.

The methods are typically carried out in the presence of any charge carriers, such as metal salts, for example alkali metal salt, halide salts, for example chloride salts, such as alkali metal chloride salt. Charge carriers may include ionic liquids or organic salts, for example tetramethyl ammonium chloride, trimethylphenyl ammonium chloride, phenyltrim-ethyl ammonium chloride, or 1-ethyl-3-methyl imidazolium chloride. In the exemplary apparatus discussed above, the salt is present in the aqueous solution in the chamber. Potassium chloride (KCl), sodium chloride (NaCl), caesium chloride (CsCl) or a mixture of potassium ferrocyanide and potassium ferricyanide is typically used. KCl, NaCl and a mixture of potassium ferrocyanide and potassium ferricyanide are preferred. The charge carriers may be asymmetric across the membrane. For instance, the type and/or concentration of the charge carriers may be different on each side of the membrane.

The salt concentration may be at saturation. The salt concentration may be 3 M or lower and is typically from 0.1 to 2.5 M, from 0.3 to 1.9 M, from 0.5 to 1.8 M, from 0.7 to 1.7 M, from 0.9 to 1.6 M or from 1 M to 1.4 M. The salt concentration is preferably from 150 mM to 1 M. The method is preferably carried out using a salt concentration of at least 0.3 M, such as at least 0.4 M, at least 0.5 M, at least 0.6 M, at least 0.8 M, at least 1.0 M, at least 1.5 M, at least 2.0 M, at least 2.5 M or at least 3.0 M. High salt concentrations provide a high signal to noise ratio and allow for currents indicative of the presence of a nucleotide to be identified against the background of normal current fluctuations.

The methods are typically carried out in the presence of a buffer. In the exemplary apparatus discussed above, the buffer is present in the aqueous solution in the chamber. Any buffer may be used in the method of the invention. Typically, the buffer is phosphate buffer. Other suitable buffers are HEPES and Tris-HCl buffer. The methods are typically carried out at a pH of from 4.0 to 12.0, from 4.5 to 10.0, from 5.0 to 9.0, from 5.5 to 8.8, from 6.0 to 8.7 or from 7.0 to 8.8 or 7.5 to 8.5. The pH used is preferably about 7.5.

The methods may be carried out at from 0° C. to 100° C., from 15° C. to 95° C., from 16° C. to 90° C., from 17° C. to 85° C., from 18° C. to 80° C., 19° C. to 70° C., or from 20° C. to 60° C. The methods are typically carried out at room temperature. The methods are optionally carried out at a temperature that supports enzyme function, such as about 37° C.

After delivery, the method preferably comprises a) allowing the polynucleotide to interact with the pore and the polynucleotide binding protein such that the polynucleotide moves through the pore and the polynucleotide binding protein controls the movement of the polynucleotide through the pore; and b) measuring the current passing through the pore as the polynucleotide moves with respect to the pore wherein the current is indicative of one or more characteristics of the polynucleotide and thereby characterising the polynucleotide.

The polynucleotide binding protein may be any protein that is capable of binding to the polynucleotide and controlling its movement through the pore. It is straightforward in the art to determine whether or not a protein binds to a polynucleotide. The protein typically interacts with and modifies at least one property of the polynucleotide. The protein may modify the polynucleotide by cleaving it to form individual nucleotides or shorter chains of nucleotides, such as di- or trinucleotides. The moiety may modify the polynucleotide by orienting it or moving it to a specific position, i.e. controlling its movement.

The polynucleotide binding protein is preferably derived from a polynucleotide handling enzyme. A polynucleotide handling enzyme is a polypeptide that is capable of interacting with and modifying at least one property of a polynucleotide. The enzyme may modify the polynucleotide by cleaving it to form individual nucleotides or shorter chains of nucleotides, such as di- or trinucleotides. The enzyme may modify the polynucleotide by orienting it or moving it to a specific position. The polynucleotide handling enzyme does not need to display enzymatic activity as long as it is capable of binding the polynucleotide and controlling its movement through the pore. For instance, the enzyme may be modified to remove its enzymatic activity or may be used under conditions which prevent it from acting as an enzyme. Such conditions are discussed in more detail below.

The polynucleotide handling enzyme is preferably derived from a nucleolytic enzyme. The polynucleotide handling enzyme used in the construct of the enzyme is more preferably derived from a member of any of the Enzyme Classification (EC) groups 3.1.11, 3.1.13, 3.1.14, 3.1.15, 3.1.16, 3.1.21, 3.1.22, 3.1.25, 3.1.26, 3.1.27, 3.1.30 and 3.1.31. The enzyme may be any of those disclosed in International Application No. PCT/GB10/000133 (published as WO 2010/086603).

Preferred enzymes are polymerases, exonucleases, helicases, translocases and topoisomerases, such as gyrases. Suitable enzymes include, but are not limited to, exonuclease I from *E. coli* (SEQ ID NO: 11), exonuclease III enzyme from *E. coli* (SEQ ID NO: 13), RecJ from *T. thermophilus* (SEQ ID NO: 15) and bacteriophage lambda exonuclease (SEQ ID NO: 17), TatD exonuclease and variants thereof. Three subunits comprising the sequence shown in SEQ ID NO: 15 or a variant thereof interact to form a trimer exonuclease. The polymerase may be PyroPhage® 3173 DNA Polymerase (which is commercially available from Lucigen® Corporation), SD Polymerase (commercially available from Bioron®) or variants thereof. The enzyme is preferably Phi29 DNA polymerase (SEQ ID NO: 9) or a variant thereof. The topoisomerase is preferably a member of any of the Moiety Classification (EC) groups 5.99.1.2 and 5.99.1.3.

The enzyme is most preferably derived from a helicase. The helicase may be or be derived from a Hel308 helicase, a RecD helicase, such as TraI helicase or a TrwC helicase, a XPD helicase or a Dda helicase. The helicase may be or be derived from Hel308 Mbu (SEQ ID NO: 18), Hel308 Csy (SEQ ID NO: 19), Hel308 Tga (SEQ ID NO: 20), Hel308 Mhu (SEQ ID NO: 21), TraI Eco (SEQ ID NO: 22), XPD Mbu (SEQ ID NO: 23) or a variant thereof.

The helicase may be any of the helicases, modified helicases or helicase constructs disclosed in International Application Nos. PCT/GB2012/052579 (published as WO 2013/057495); PCT/GB2012/053274 (published as WO 2013/098562); PCT/GB2012/053273 (published as WO2013098561); PCT/GB2013/051925 (published as WO 2014/013260); PCT/GB2013/051924 (published as WO 2014/013259); PCT/GB2013/051928 (published as WO 2014/013262) and PCT/GB2014/052736 (published as WO/2015/055981).

The helicase preferably comprises the sequence shown in SEQ ID NO: 25 (Trwc Cba) or as variant thereof, the sequence shown in SEQ ID NO: 18 (Hel308 Mbu) or a variant thereof or the sequence shown in SEQ ID NO: 24 (Dda) or a variant thereof. Variants may differ from the native sequences in any of the ways discussed below for transmembrane pores. A preferred variant of SEQ ID NO: 24 comprises (a) E94C and A360C or (b) E94C, A360C, C109A and C136A and then optionally (ΔM1)G1 (i.e. deletion of M1 and then addition G1). It may also be termed M1G. Any of the variants discussed above may further comprise M1G.

Any number of helicases may be used in accordance with the invention. For instance, 1, 2, 3, 4, 5, 6, 7, 8, 9, 10 or more helicases may be used. In some embodiments, different numbers of helicases may be used.

The method of the invention preferably comprises contacting the polynucleotide with two or more helicases. The two or more helicases are typically the same helicase. The two or more helicases may be different helicases.

The two or more helicases may be any combination of the helicases mentioned above. The two or more helicases may be two or more Dda helicases. The two or more helicases may be one or more Dda helicases and one or more TrwC helicases. The two or more helicases may be different variants of the same helicase.

The two or more helicases are preferably attached to one another. The two or more helicases are more preferably covalently attached to one another. The helicases may be attached in any order and using any method. Preferred helicase constructs for use in the invention are described in International Application Nos. PCT/GB2013/051925 (published as WO 2014/013260); PCT/GB2013/051924 (published as WO 2014/013259); PCT/GB2013/051928 (published as WO 2014/013262) and PCT/GB2014/052736.

A variant of SEQ ID NO: 9, 11, 13, 15, 17, 18, 19, 20, 21, 22, 23, 24 or 25 is an enzyme that has an amino acid sequence which varies from that of SEQ ID NO: 9, 11, 13, 15, 17, 18, 19, 20, 21, 22, 23, 24 or 25 and which retains polynucleotide binding ability. This can be measured using any method known in the art. For instance, the variant can be contacted with a polynucleotide and its ability to bind to and move along the polynucleotide can be measured. The variant may include modifications that facilitate binding of the polynucleotide and/or facilitate its activity at high salt concentrations and/or room temperature. Variants may be modified such that they bind polynucleotides (i.e. retain polynucleotide binding ability) but do not function as a helicase (i.e. do not move along polynucleotides when provided with all the necessary components to facilitate movement, e.g. ATP and $Mg^{2+}$). Such modifications are known in the art. For instance, modification of the $Mg^{2+}$ binding domain in helicases typically results in variants which do not function as helicases. These types of variants may act as molecular brakes (see below).

Over the entire length of the amino acid sequence of SEQ ID NO: 9, 11, 13, 15, 17, 18, 19, 20, 21, 22, 23, 24 or 25, a variant will preferably be at least 50% homologous to that sequence based on amino acid identity. More preferably, the variant polypeptide may be at least 55%, at least 60%, at least 65%, at least 70%, at least 75%, at least 80%, at least 85%, at least 90% and more preferably at least 95%, 97% or 99% homologous based on amino acid identity to the amino acid sequence of SEQ ID NO: 9, 11, 13, 15, 17, 18, 19, 20, 21, 22, 23, 24 or 25 over the entire sequence. There may be at least 80%, for example at least 85%, 90% or 95%, amino acid identity over a stretch of 200 or more, for example 230, 250, 270, 280, 300, 400, 500, 600, 700, 800, 900 or 1000 or more, contiguous amino acids ("hard homology"). Homology is determined as described above. The variant may differ from the wild-type sequence in any of the ways discussed above with reference to SEQ ID NO: 2 and 4 above. The enzyme may be covalently attached to the pore. Any method may be used to covalently attach the enzyme to the pore.

A preferred molecular brake is TrwC Cba-Q594A (SEQ ID NO: 25 with the mutation Q594A). This variant does not function as a helicase (i.e. binds polynucleotides but does not move along them when provided with all the necessary components to facilitate movement, e.g. ATP and $Mg^{2+}$).

In strand sequencing, the polynucleotide is translocated through the pore either with or against an applied potential. Exonucleases that act progressively or processively on double stranded polynucleotides can be used on the cis side of the pore to feed the remaining single strand through under an applied potential or the trans side under a reverse potential. Likewise, a helicase that unwinds the double stranded DNA can also be used in a similar manner. A polymerase may also be used. There are also possibilities for sequencing applications that require strand translocation against an applied potential, but the DNA must be first "caught" by the enzyme under a reverse or no potential. With the potential then switched back following binding the strand will pass cis to trans through the pore and be held in an extended conformation by the current flow. The single strand DNA exonucleases or single strand DNA dependent polymerases can act as molecular motors to pull the recently translocated single strand back through the pore in a controlled stepwise manner, trans to cis, against the applied potential.

Any helicase may be used in the method. Helicases may work in two modes with respect to the pore. First, the method is preferably carried out using a helicase such that it moves the polynucleotide through the pore with the field resulting from the applied voltage. In this mode the 5' end of the polynucleotide is first captured in the pore, and the helicase moves the polynucleotide into the pore such that it is passed through the pore with the field until it finally translocates through to the trans side of the membrane. Alternatively, the method is preferably carried out such that a helicase moves the polynucleotide through the pore against the field resulting from the applied voltage. In this mode the 3' end of the polynucleotide is first captured in the pore, and the helicase moves the polynucleotide through the pore such that it is pulled out of the pore against the applied field until finally ejected back to the cis side of the membrane.

The method may also be carried out in the opposite direction. The 3' end of the polynucleotide may be first captured in the pore and the helicase may move the polynucleotide into the pore such that it is passed through the pore with the field until it finally translocates through to the trans side of the membrane.

When the helicase is not provided with the necessary components to facilitate movement or is modified to hinder or prevent its movement, it can bind to the polynucleotide and act as a brake slowing the movement of the polynucleotide when it is pulled into the pore by the applied field. In the inactive mode, it does not matter whether the polynucleotide is captured either 3' or 5' down, it is the applied field which pulls the polynucleotide into the pore towards the trans side with the enzyme acting as a brake. When in the inactive mode, the movement control of the polynucleotide by the helicase can be described in a number of ways including ratcheting, sliding and braking. Helicase variants which lack helicase activity can also be used in this way.

The polynucleotide may be contacted with the polynucleotide binding protein and the pore in any order. It is preferred that, when the polynucleotide is contacted with the polynucleotide binding protein, such as a helicase, and the pore, the polynucleotide firstly forms a complex with the protein. When the voltage is applied across the pore, the polynucleotide/protein complex then forms a complex with the pore and controls the movement of the polynucleotide through the pore.

Any steps in the method using a polynucleotide binding protein are typically carried out in the presence of free nucleotides or free nucleotide analogues and an enzyme cofactor that facilitates the action of the polynucleotide binding protein. The free nucleotides may be one or more of any of the individual nucleotides discussed above. The free nucleotides include, but are not limited to, adenosine monophosphate (AMP), adenosine diphosphate (ADP), adenosine triphosphate (ATP), guanosine monophosphate (GMP), guanosine diphosphate (GDP), guanosine triphosphate (GTP), thymidine monophosphate (TMP), thymidine diphosphate (TDP), thymidine triphosphate (TTP), uridine monophosphate (UMP), uridine diphosphate (UDP), uridine triphosphate (UTP), cytidine monophosphate (CMP), cytidine diphosphate (CDP), cytidine triphosphate (CTP), cyclic adenosine monophosphate (cAMP), cyclic guanosine monophosphate (cGMP), deoxyadenosine monophosphate (dAMP), deoxyadenosine diphosphate (dADP), deoxyadenosine triphosphate (dATP), deoxyguanosine monophosphate (dGMP), deoxyguanosine diphosphate (dGDP), deoxyguanosine triphosphate (dGTP), deoxythymidine monophosphate (dTMP), deoxythymidine diphosphate (dTDP), deoxythymidine triphosphate (dTTP), deoxyuridine monophosphate (dUMP), deoxyuridine diphosphate (dUDP), deoxyuridine triphosphate (dUTP), deoxycytidine monophosphate (dCMP), deoxycytidine diphosphate (dCDP) and deoxycytidine triphosphate (dCTP). The free nucleotides are preferably selected from AMP, TMP, GMP, CMP, UMP, dAMP, dTMP, dGMP or dCMP. The free nucleotides are preferably adenosine triphosphate (ATP). The enzyme cofactor is a factor that allows the construct to function. The enzyme cofactor is preferably a divalent metal cation. The divalent metal cation is preferably $Mg^{2+}$, $Mn^{2+}$, $Ca^{2+}$ or $Co^{2+}$. The enzyme cofactor is most preferably $Mg^{2+}$.

Helicase(s) and Molecular Brake(s)

In a preferred embodiment, the method comprises:

(a) providing a polynucleotide analyte attached to a microparticle, wherein the polynucleotide analyte has one or more helicases and one or more molecular brakes attached to it;

(b) delivering the microparticle towards the membrane and thereby delivering the polynucleotide to the transmembrane pore;

(c) applying a potential across the pore such that the one or more helicases and the one or more molecular brakes are brought together and both control the movement of the polynucleotide through the pore; and (d) taking one or more measurements as the polynucleotide moves with respect to the pore wherein the measurements are indicative of one or more characteristics of the polynucleotide and thereby characterising the polynucleotide.

This type of method is discussed in detail in International Application No. PCT/GB2014/052737.

The one or more helicases may be any of those discussed above. The one or more molecular brakes may be any compound or molecule which binds to the polynucleotide and slow the movement of the polynucleotide through the pore. The one or more molecular brakes preferably comprise one or more compounds which bind to the polynucleotide. The one or more compounds are preferably one or more macrocycles. Suitable macrocycles include, but are not limited to, cyclodextrins, calixarenes, cyclic peptides, crown ethers, cucurbiturils, pillararenes, derivatives thereof or a combination thereof. The cyclodextrin or derivative thereof may be any of those disclosed in Eliseev, A. V., and Schneider, H-J. (1994) *J. Am. Chem. Soc.* 116, 6081-6088. The agent is more preferably heptakis-6-amino-β-cyclodextrin ($am_7$-βCD), 6-monodeoxy-6-monoamino-β-cyclodextrin ($am_1$-βCD) or heptakis-(6-deoxy-6-guanidino)-cyclodextrin ($gu_7$-βCD).

Spacers in Polynucleotide Analytes

The one or more helicases may be stalled at one or more spacers as discussed in International Application No. PCT/GB2014/050175. Any configuration of one or more helicases and one or more spacers disclosed in the International Application may be used in this invention.

Double Stranded Polynucleotide

If the polynucleotide analyte is double stranded, the method preferably further comprises providing the polynucleotide with a hairpin adaptor at one end of the polynucleotide and separating the two strands of the polynucleotide to form a single stranded polynucleotide construct. The single stranded polynucleotide construct may then be allowed to interact with the pore in accordance with the invention. Linking and interrogating both strands on a double stranded construct in this way increases the efficiency and accuracy of characterisation.

Suitable hairpin adaptors can be designed using methods known in the art. The hairpin loop may be any length. The hairpin loop is typically 110 or fewer nucleotides, such as 100 or fewer nucleotides, 90 or fewer nucleotides, 80 or fewer nucleotides, 70 or fewer nucleotides, 60 or fewer nucleotides, 50 or fewer nucleotides, 40 or fewer nucleotides, 30 or fewer nucleotides, 20 or fewer nucleotides or 10 or fewer nucleotides, in length. The hairpin loop is preferably from about 1 to 110, from 2 to 100, from 5 to 80 or from 6 to 50 nucleotides in length. Longer lengths of the hairpin loop, such as from 50 to 110 nucleotides, are preferred if the loop is involved in the differential selectability of the adaptor. Similarly, shorter lengths of the hairpin loop, such as from 1 to 5 nucleotides, are preferred if the loop is not involved in the selectable binding as discussed below.

The hairpin adaptor may be provided at either end of the polynucleotide, i.e. the 5' or the 3' end. The hairpin adaptor may be ligated to the polynucleotide using any method known in the art. The hairpin adaptor may be ligated using a ligase, such as T4 DNA ligase, *E. coli* DNA ligase, Taq DNA ligase, Tma DNA ligase and 9°N DNA ligase.

The two strands of the polynucleotide may be separated using any method known in the art. For instance, they may be separated by a polynucleotide binding protein or using conditions which favour dehybridsation (examples of conditions which favour dehybridisation include, but are not limited to, high temperature, high pH and the addition of agents that can disrupt hydrogen bonding or base pairing, such as formamide and urea).

The hairpin adaptor preferably comprises a selectable binding moiety. This allows the polynucleotide to be purified or isolated. A selectable binding moiety is a moiety that can be selected on the basis of its binding properties. Hence, a selectable binding moiety is preferably a moiety that specifically binds to a surface. A selectable binding moiety specifically binds to a surface if it binds to the surface to a much greater degree than any other moiety used in the invention. In preferred embodiments, the moiety binds to a surface to which no other moiety used in the invention binds.

Suitable selective binding moieties are known in the art. Preferred selective binding moieties include, but are not limited to, biotin, a polynucleotide sequence, antibodies, antibody fragments, such as Fab and ScSv, antigens, polynucleotide binding proteins, poly histidine tails and GST tags. The most preferred selective binding moieties are biotin and a selectable polynucleotide sequence. Biotin specifically binds to a surface coated with avidins. Selectable polynucleotide sequences specifically bind (i.e. hybridise) to a surface coated with homologus sequences. Alternatively, selectable polynucleotide sequences specifically bind to a surface coated with polynucleotide binding proteins.

The hairpin adaptor and/or the selectable binding moiety may comprise a region that can be cut, nicked, cleaved or hydrolysed. Such a region can be designed to allow the polynucleotide to be removed from the surface to which it is bound following purification or isolation. Suitable regions are known in the art. Suitable regions include, but are not limited to, an RNA region, a region comprising desthiobiotin and streptavidin, a disulphide bond and a photocleavable region.

Leader Sequence

The polynucleotide analyte may be provided with a leader sequence which preferentially threads into the pore. The leader sequence facilitates the method of the invention. The leader sequence is designed to preferentially thread into the transmembrane pore and thereby facilitate the movement of polynucleotide analyte through the pore. The leader sequence can also be used to link the polynucleotide to the one or more anchors as discussed above.

The leader sequence typically comprises a polymer. The polymer is preferably negatively charged. The polymer is preferably a polynucleotide, such as DNA or RNA, a modified polynucleotide (such as abasic DNA), PNA, LNA, polyethylene glycol (PEG) or a polypeptide. The leader preferably comprises a polynucleotide and more preferably comprises a single stranded polynucleotide. The leader sequence can comprise any of the polynucleotides discussed above. The single stranded leader sequence most preferably comprises a single strand of DNA, such as a poly dT section. The leader sequence preferably comprises the one or more spacers.

The leader sequence can be any length, but is typically 10 to 150 nucleotides in length, such as from 20 to 150 nucleotides in length. The length of the leader typically depends on the transmembrane pore used in the method.

Double Coupling

The method of the invention may involve double coupling of a double stranded polynucleotide. The method preferably comprises:

(a) providing a double stranded polynucleotide attached to a microparticle, wherein the polynucleotide has a Y adaptor at one end and a hairpin loop adaptor at the other end, wherein the Y adaptor comprises one or more first anchors for coupling the polynucleotide to the membrane, wherein the hairpin loop adaptor comprises one or more second anchors for coupling the polynucleotide to the membrane and wherein the strength of coupling of the hairpin loop adaptor to the membrane is greater than the strength of coupling of the Y adaptor to the membrane;

(b) delivering the microparticle towards the membrane and thereby delivering the polynucleotide to the transmembrane pore (c) allowing the polynucleotide to interact with the pore such that at least one strand of the polynucleotide moves through the pore;

(d) taking one or more measurements as the at least one strand of the polynucleotide moves with respect to the pore wherein the measurements are indicative of one or more characteristics of the at least one strand of the polynucleotide and thereby characterising the polynucleotide. In a preferred embodiment, both strands of the polynucleotide move through the pore.

This type of method is discussed in detail in the PCT Application No. PCT/GB2015/050991.

The double stranded polynucleotide is provided with a Y adaptor at one end and a hairpin loop adaptor at the other end. The Y adaptor and/or the hairpin adaptor are typically polynucleotide adaptors. They may be formed from any of the polynucleotides discussed above.

The Y adaptor typically comprises (a) a double stranded region and (b) a single stranded region or a region that is not complementary at the other end. The Y adaptor may be described as having an overhang if it comprises a single stranded region. The presence of a non-complementary region in the Y adaptor gives the adaptor its Y shape since the two strands typically do not hybridise to each other unlike the double stranded portion. The Y adaptor comprises the one or more first anchors. Anchors are discussed in more detail above.

The Y adaptor preferably comprises a leader sequence which preferentially threads into the pore. Leader sequences are discussed above.

The hairpin adaptor preferably comprises a selectable binding moiety as discussed above. The hairpin adaptor and/or the selectable binding moiety may comprise a region that can be cut, nicked, cleaved or hydrolysed as discussed above.

The Y adaptor and/or the hairpin adaptor may be ligated to the polynucleotide using any method known in the art.

One or both of the adaptors may be ligated using a ligase, such as T4 DNA ligase, E. coli DNA ligase, Taq DNA ligase, Tma DNA ligase and 9°N DNA ligase. Alternatively, the adaptors may be added to the polynucleotide using the methods of the invention discussed below.

In a preferred embodiment, the method comprises modifying the double stranded polynucleotide so that it comprises the Y adaptor at one end and the hairpin loop adaptor at the other end. Any manner of modification can be used. The method preferably comprises modifying the double stranded polynucleotide in accordance with the invention. This is discussed in more detail below. The methods of modification and characterisation may be combined in any way.

The strength of coupling (or binding) of the hairpin adaptor to the membrane is greater than the strength of coupling (or binding) of the Y adaptor to the membrane. This can be measured in any way. A suitable method for measuring the strength of coupling (or binding) is disclosed in the Examples of the UK Application Nos. 1406147.7 and 140781.8.

The strength of coupling (or binding) of the hairpin loop adaptor is preferably at least 1.5 times the strength of coupling (or binding) of the hairpin loop adaptor, such as at least twice, at least three times, at least four times, at least five or at least ten times the strength of coupling (or binding) of the anchor adaptor. The affinity constant (Kd) of the hairpin loop adaptor for the membrane is preferably at least 1.5 times the affinity constant of the Y adaptor, such as at least twice, at least three times, at least four times, at least five or at least ten times the strength of coupling of the Y adaptor.

There are several ways in which the hairpin loop adaptor couples (or binds) more strongly to the membrane than the Y adaptor. For instance, the hairpin loop adaptor may comprise more anchors that than the Y adaptor. For instance, the hairpin loop adaptor may comprise 2, 3 or more second anchors whereas the Y adaptor may comprise one first anchor.

The strength of coupling (or binding) of the one or more second anchors to the membrane may be greater than the strength of coupling (or binding) of the one or more first anchors to the membrane. The strength of coupling (or binding) of the one or more second anchors to the hairpin loop adaptor may be greater than the strength of coupling (or binding) of the one or more first anchors to the Y adaptor. The one or more first anchors and the one or more second anchors may be attached to their respective adaptors via hybridisation and the strength of hybridisation is greater in the one or more second anchors than in the one or more first anchors. Any combination of these embodiments may also be used in the invention. Strength of coupling (or binding) may be measure using known techniques in the art.

The one or more second anchors preferably comprise one or more groups which couples(s) (or bind(s)) to the membrane with a greater strength than the one or more groups in the one or more first anchors which couple(s) (or bind(s)) to the membrane. In preferred embodiments, the hairpin loop adaptor/one or more second anchors couple (or bind) to the membrane using cholesterol and the Y adaptor/one or more first anchors couple (or bind) to the membrane using palmitate. Cholesterol binds to triblock copolymer membranes and lipid membranes more strongly than palmitate. In an alternative embodiment, the hairpin loop adaptor/one or more second anchors couple (or bind) to the membrane using a mono-acyl species, such as palmitate, and the Y adaptor/one or more first anchors couple (or bind) to the membrane using a diacyl species, such as dipalmitoylphosphatidylcholine.

Adding Hairpin Loops and Leader Sequences

The double stranded polynucleotide may be provided with Y and hairpin adaptors by contacting the polynucleotide with a MuA transposase and a population of double stranded MuA substrates, wherein a proportion of the substrates in the population are Y adaptors comprising the leader sequence and wherein a proportion of the substrates in the population are hairpin loop adaptors. The transposase fragments the double stranded polynucleotide analyte and ligates MuA substrates to one or both ends of the fragments. This produces a plurality of modified double stranded polynucleotides comprising the leader sequence at one end and the hairpin loop at the other. The modified double stranded polynucleotides may then be investigated using the method of the invention.

These MuA based methods are disclosed in PCT Application No. PCT/GB2014/052505 published as (WO 2015/022544). They are also discussed in detail in PCT Application No PCT/GB2015/050991.

Modified Polynucleotide Analytes

Before delivery and characterisation in accordance with the invention, the polynucleotide analyte may be modified by contacting the polynucleotide analyte with a polymerase and a population of free nucleotides under conditions in which the polymerase forms a modified polynucleotide analyte using the polynucleotide analyte as a template, wherein the polymerase replaces one or more of the nucleotide species in the polynucleotide analyte with a different nucleotide species when forming the modified polynucleotide analyte. The modified polynucleotide analyte may then be attached to the microparticle and delivered towards the membrane. This type of modification is described in PCT Application No. PCT/GB2015/050483. Any of the polymerases discussed above may be used. The polymerase is preferably Klenow or 9o North.

Other Characterisation Method

In another embodiment, after delivery to the transmembrane pore, the polynucleotide analyte is characterised by detecting labelled species that are released as a polymerase incorporates nucleotides into the polynucleotide. The polymerase uses the polynucleotide analyte as a template. Each labelled species is specific for each nucleotide. The polynucleotide analyte is delivered to the transmembrane pore and then contacted with a polymerase and labelled nucleotides such that phosphate labelled species are sequentially released when nucleotides are added to the polynucleotide(s) by the polymerase, wherein the phosphate species contain a label specific for each nucleotide. The polymerase may be any of those discussed above. The phosphate labelled species are detected using the pore and thereby characterising the polynucleotide analyte. This type of method is disclosed in European Application No. 13187149.3 (published as EP 2682460). Any of the embodiments discussed above equally apply to this method.

Kits

The present invention also provides a kit for delivering an analyte to a transmembrane pore in a membrane, comprising (a) a microparticle and (b) one or more anchors which are capable of coupling the analyte to the membrane. The microparticle and one or more anchors may be any of those discussed above with reference to the method of the invention. If the kit is for delivering a polynucleotide to the pore, the microparticle is preferably part of the kit for extracting and/or purifying the polynucleotide.

The kit preferably further comprises a hairpin loop and/or a leader sequence which is capable of preferentially threading into a transmembrane pore. The kit may comprise a Y adaptor. The kit preferably further comprises a polynucleotide binding protein. Preferred hairpin loops, leader sequences, Y adaptors and polynucleotide binding proteins are discussed above.

Any of the embodiments discussed above with reference to the method of the invention equally apply to the kits. The kit may further comprise the components of a membrane, such as the components of an amphiphilic layer or a triblock copolymer membrane. The kit may further comprise a transmembrane protein pore.

The kit of the invention may additionally comprise one or more other reagents or instruments which enable any of the embodiments mentioned above to be carried out. The kit may comprise a magnet or an electromagnet. Such reagents or instruments include one or more of the following: suitable buffer(s) (aqueous solutions), means to obtain a sample from a subject (such as a vessel or an instrument comprising a needle), means to amplify and/or express polynucleotides, a membrane as defined above or voltage or patch clamp apparatus. Reagents may be present in the kit in a dry state such that a fluid sample resuspends the reagents. The kit may also, optionally, comprise instructions to enable the kit to be used in the method of the invention or details regarding for which organism the method may be used.

The following Examples illustrate the invention.

EXAMPLES

Example 1

This example describes the sample preparation procedure for attaching a helicase, which was bound to DNA, to his-tag isolation and pulldown Dynabeads® (Life Technologies) and then adding the beads to a nanopore system in order to detect helicase-controlled DNA movement. FIG. 1 shows a cartoon representation of how the DNA was attached to the bead. The DNA was also hybridised to DNA strands which had anchors attached (one DNA with anchor was hybridised to the Y-adapter and the second DNA with anchor was hybridised to the hairpin adapter (See FIG. 1)), which assisted in delivering the DNA onto the nanopore in the membrane. It was observed that the experiment which used beads to deliver the DNA to the nanopore resulted in a concentration enhancement in comparison to the control where the same concentration of DNA was added to the nanopore system.

Materials and Methods 1.1 Wash Treatment of His-Tag Isolation and Pulldown Dynabeads®

The stock sample which contained the his-tag Isolation and pulldown Dynabeads® was vortexed in order to thoroughly re-suspend the Dynabeads® throughout the solution. A sample of the bead solution (10 µL) was removed from the stock solution and added to an Eppendorf Protein Low-Bind tube (1.5 mL). The tube was placed on a magnetic rack and the supernatant removed once all of the beads had stuck to the magnet. Buffer was added to the magnetic bead sample (500 µL of 500 mM KCl, pH 8.0, 25 mM potassium phosphate buffer) and the beads were re-suspended by vortexing. The tube was then placed on the magnetic rack and the supernatant removed once the beads had stuck to the magnet. The buffer wash and supernatant removal steps were repeated a further two times so that the beads had been washed a total of three times using the buffer (500 mM KCl, pH 8.0, 25 mM potassium phosphate buffer). The beads were then re-suspended in (10 µL of 500 mM KCl, pH 8.0, and 25 mM potassium phosphate buffer) and this was known as the washed bead stock solution. Before use the bead stock solution was vortexed in order to thoroughly re-suspend the Dynabeads® throughout the solution.

1.2 Attachment of DNA (with Pre-Bound Helicase) to the Dynabeads®

A DNA library (which contained double-stranded lambda DNA which had been fragmented and then attached to a Y-adapter (which had a helicase attached to the leader) and a hairpin adapter (which had a different his-tagged helicase attached to the hairpin) and finally hybridised to two strands of DNA which had anchors attached (see FIG. 1)) was added to the washed Dynabeads® (see Table 5 below) and the sample incubated at room temperature for at least one hour. This sample was known as DNA/bead sample 2.

TABLE 5

| Reagent | Volume | Final Concentration |
| --- | --- | --- |
| DNA Library | 0.12 µl | 1 nM |
| Washed His-binding Dynabeads ® produced in step 1.1 | 0.4 µl | |
| Total | 0.52 µl | |

1.3 Electrophysiology

Prior to setting up the experiment, DNA/bead sample 2 (0.52 µL) was added to buffer (145.5 µL, 25 mM Potassium Phosphate buffer, pH 8.0, 500 mM KCl) and fuel mix (4 µL of MgCl2 (75 mM) and ATP (75 mM)).

Electrical measurements were acquired from single MspA nanopores inserted in block co-polymer in buffer (25 mM potassium phosphate buffer, 150 mM potassium ferrocyanide (II), and 150 mM potassium ferricyanide (III), pH 8.0). After achieving a single pore inserted in the block co-polymer, then buffer (2 mL, 25 mM K Phosphate buffer, 150 mM Potassium Ferrocyanide (II), 150 mM Potassium Ferricyanide (III), pH 8.0) was flowed through the system to remove any excess MspA nanopores.

An excess of buffer (500 mM KCl, 25 mM potassium phosphate, pH 8.0) was flowed through the nanopore system prior to adding the sample. The DNA/bead sample 2 and fuel pre-mix (155 µL total) was then flowed into the single nanopore experimental system. The experiment was run at −120 mV and helicase-controlled DNA movement monitored.

An analogous control experiment was also carried out where the same concentration of DNA library (which had not been bound to the Dynabeads®) was added to the nanopore system and helicase controlled DNA movement was monitored as described above.

Results

Figure 2:
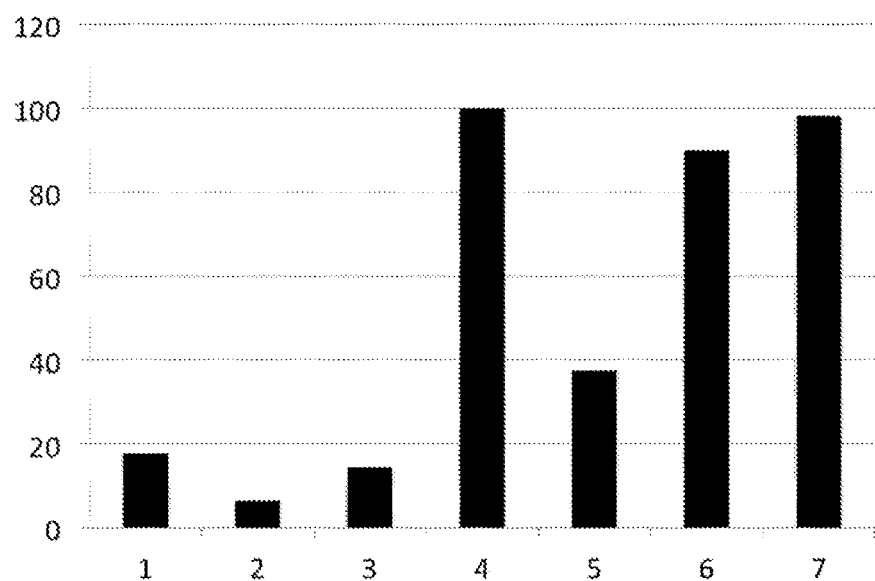
FIG. 2 shows a bar chart of the throughput (megabases of sequenced DNA per hour) normalised to the maximum throughput observed when a DNA library sample was pre-incubated with (lanes 4-7) or without (lanes 1-3) Dynabeads®. The y-axis label=throughput normalised to the maximum and the x-axis label=run number.

Helicase controlled DNA movement was observed for both the control reaction (where the DNA was not bound to the beads) and the DNA/bead sample 2. FIG. 2 shows seven different nanopore experiments (1-3 were control reactions with no beads and 4-7 were DNA/bead sample 2). The control experiments used DNA with two anchors, whereas the bead experiments used both the beads and the two anchors to aid in delivery of the DNA to the nanopore. The throughput values shown in FIG. 2 were normalised relative to the maximum throughput observed over the runs tested (run 4). The DNA library which was not bound to beads observed normalised throughput values of approximately 15 in all three experiments. Whereas, the DNA/bead sample 2 resulted in normalised throughput values of approximately 90. Therefore, when the DNA library was pre-incubated with Dynabeads® a large increase in the normalised throughput was observed. This meant that the Dynabeads® assisted in delivering DNA directly to the nanopore system and resulted in a concentration enhancement in comparison to the control.

Example 2

This example describes how images were taken of the nanopore chip array which showed how the Dynabeads® were observed to deliver the DNA directly to the membrane in which the MspA nanopores were present. Images taken of the system over time showed that the beads were observed to concentrate at the membrane surface which had nanopores inserted therein.

Materials and Methods 2.1 Preparation of Dynabeads® with DNA Attached

The Dynabeads® were washed as described in example 1.1 and DNA was attached to the beads as described in example 1.2.

2.2 Imaging of the Chip

A series of Brightfield images of the nanopore chip system were captured using a microscope with a 20× objective.

Results

Figure 3:
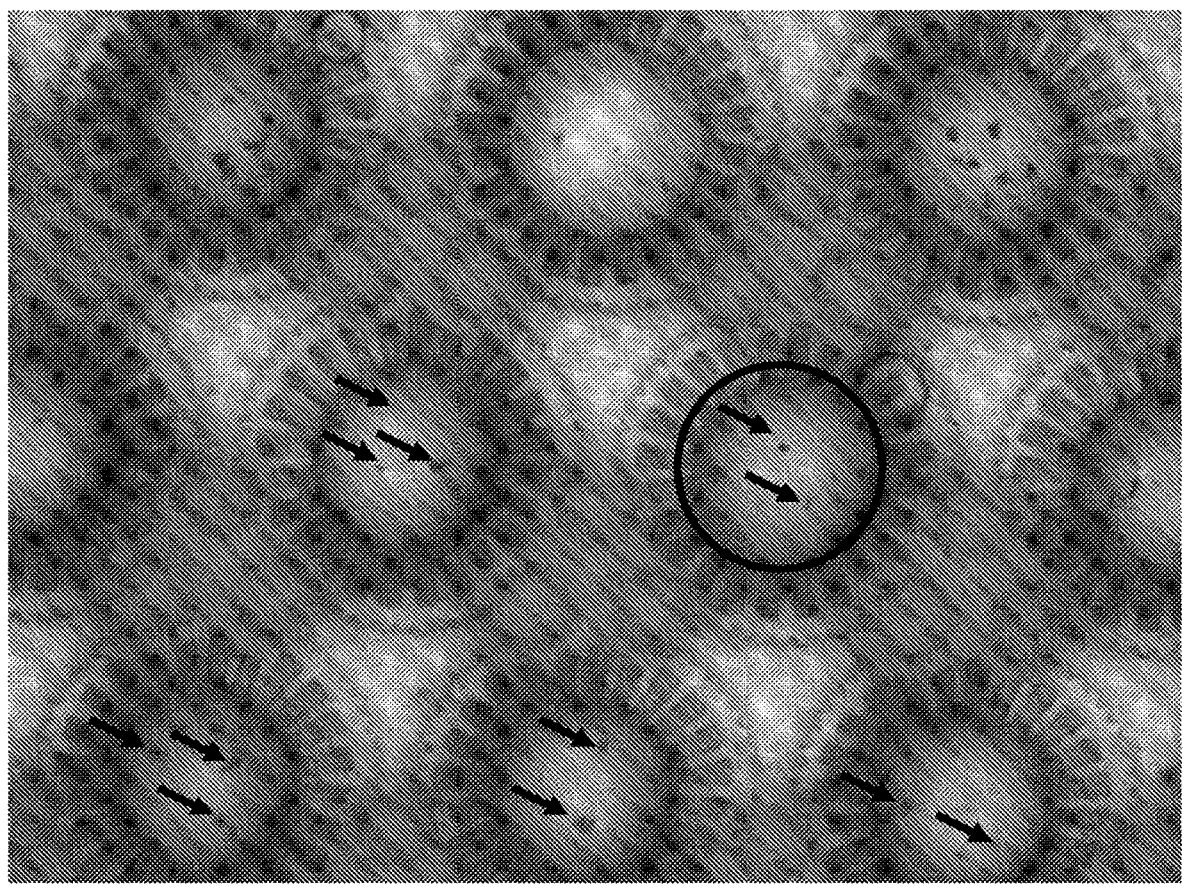
FIG. 3 shows a Brightfield image of the nanopore chip system immediately after the addition of DNA/bead sample. A small number of Dynabeads® (seen as small dark dots) were observed on the region of the chip where the membrane formed (this region is highlighted on one of the wells by a black circle).
Figure 4:
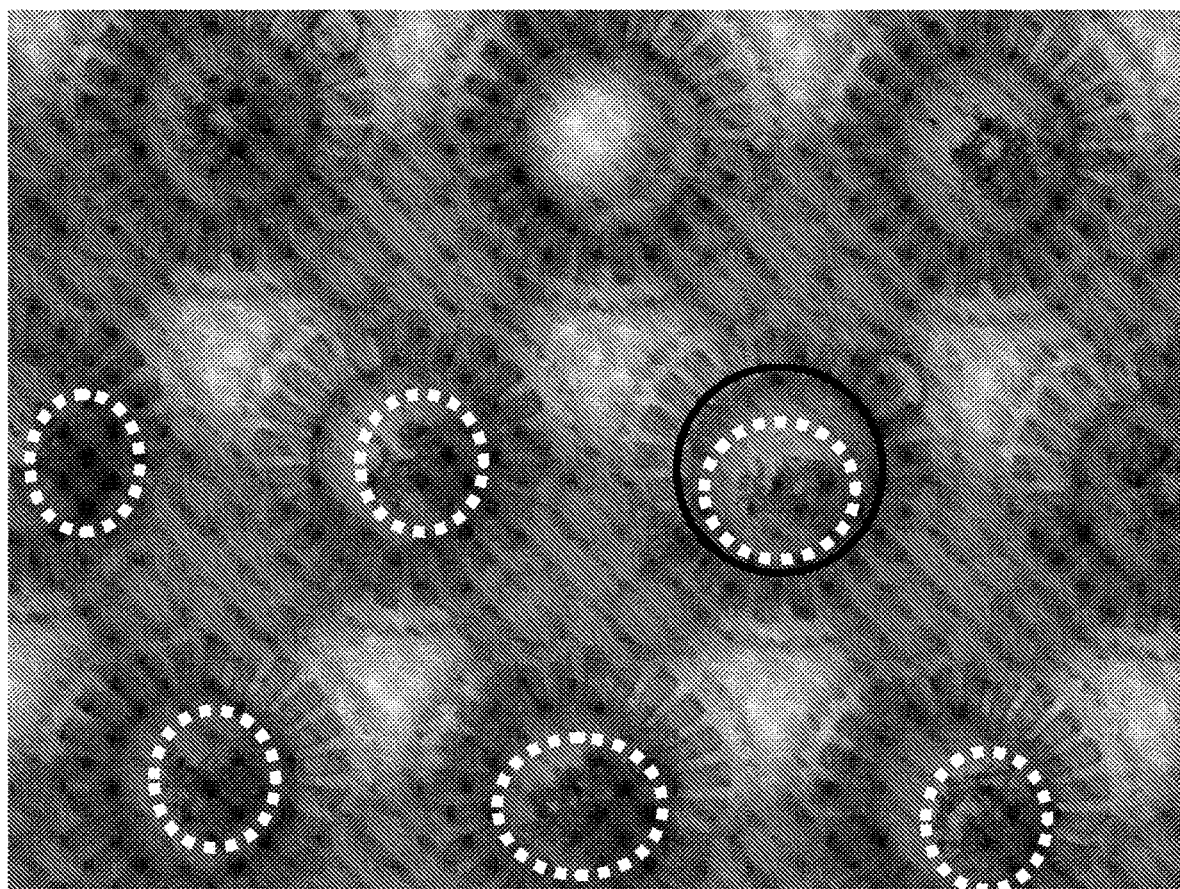
FIG. 4 shows a Brightfield image of the nanopore chip system 20 minutes after the addition of DNA/bead sample. Large clusters of Dynabeads® (highlighted in the figure by white dashed line circles) were observed on the region of the chip where the membrane formed (this region is highlighted on one of the wells by a black circle).

FIGS. 3 and 4 show two of the Brightfield images taken of the nanopore chip system. FIG. 3 shows the chip immediately after the DNA/bead sample was added. A small number of small dark beads were visible above the chip well where the membrane for nanopore insertion was located (some of the beads are highlighted in the figure with black arrows). FIG. 4 shows the same region of the nanopore chip system 20 minutes after the DNA/bead sample was added. Large clusters of the beads were observed above the chip well where the membrane for nanopore insertion was located (some of these bead clusters are highlighted in the figure by a dashed white line circle around the cluster). FIG. 8A shows a cartoon representation of how the beads may have concentrated on the membrane. Therefore, it was clear from the images taken of the chip that the beads localised to the centre of each membrane, delivering the DNA sample near to the nanopore.

Example 3

This example describes how different types of beads were tested to see how they affected the stability of the membranes which were formed in the nanopore chip array experiments. None of the beads tested resulted in significant damage to the membrane and, therefore, these beads could be used for enhanced delivery of DNA to a nanopore system.

Materials and Methods 2.1 Preparation of Dynabeads® with a Variety of Surface Coatings Dynabeads® with the following functionalisations (1—silane, 2—streptavidin, 3—streptavidin bound with short biotinylated DNA strands, 4—cobalt-based His-Tag isolation and pulldown)) were tested to determine what effect they had on the membrane. The Dynabeads® were provided in different storage solutions. The stock vials were vortexed for 10 seconds and then a sample (30 µL) of the beads in storage solution was added to an Eppendorf. The beads were separated from the storage solution by placing the Eppendorf next to a magnet and then removing the supernatant. Buffer (500 μL, 25 mM Potassium Phosphate buffer, pH 8.0, 500 mM KCl) was then added to the tube and the sample vortexed for 10 seconds. The buffer and beads were then separated and the washing buffer discarded. The beads were then re-suspended in buffer (30 μL, 25 mM Potassium Phosphate buffer, pH 8.0, 500 mM KCl) and then the beads were diluted (4 μL stock beads into 150 μL of buffer (25 mM Potassium Phosphate buffer, pH 8.0, 500 mM KCl) which also contained a short strand of random sequence DNA).

2.2 Electrical Tests to Determine Stability of the Membrane

Electrical measurements were acquired on an array chip with a number of wells over which block co-polymer formed a membrane and individual MspA nanopores inserted into the membrane in buffer (25 mM potassium phosphate buffer, 150 mM potassium ferrocyanide (II), and 150 mM potassium ferricyanide (III), pH 8.0). After achieving single pores in the block co-polymer, then buffer (3 mL, 25 mM K Phosphate buffer, 150 mM Potassium Ferrocyanide (II), 150 mM Potassium Ferricyanide (III), pH 8.0) was flowed through the system to remove any excess MspA nanopores. Prior to the addition of the bead solution, buffer (3 mL, 25 mM Potassium Phosphate buffer, pH 8.0, 500 mM KCl) was flowed through the system and then a potential of 180 mV was applied and the system (prior to the addition of the beads) was monitored. The different Dynabead® samples in buffer (mixed with the short strand of random sequence DNA) were then flowed into the single nanopore experimental chip system and a potential of 180 mV was applied. The short strand of random DNA sequence was added in order to assist in identification of single MspA nanopores as the strands produced a characteristic current signal as they translocated through the nanopore.

Results

Figure 5:
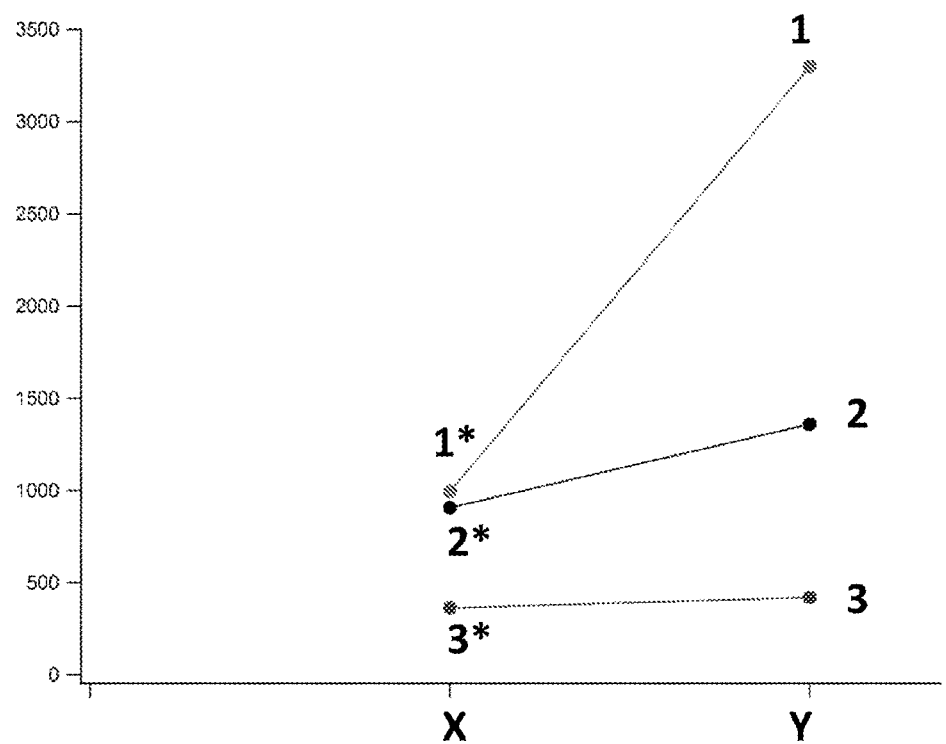
FIG. 5 shows a plot of the number of saturated channels (Y-axis) before (point X) and after (point Y) various Dynabeads® were added. The different Dynabead® functionalisations that were investigated were 1—silane, 2—streptavidin and 3—streptavidin bound with short biotinylated DNA strands.

The number of individual channels that were saturated and could not be used were counted before and after the beads were added. Point X in FIG. 5 shows the number of saturated channels before the Dynabeads® were added for the different Dynabead functionalisations (1*=silane, 2*=streptavidin and 3*=streptavidin bound with short biotinylated DNA strands). Point Y in FIG. 5 shows the number of saturated channels after the different Dynabeads® (1=silane, 2=streptavidin and 3=streptavidin bound with short biotinylated DNA strands) were added. A relatively small increase in the number of saturated channels was observed for streptavidin functionalised beads and streptavidin functionalised beads that were bound to a short strand of biotinylated DNA. However, when the beads were covered with silane a slightly larger increase in the number of saturated channels was observed.

Figure 6:
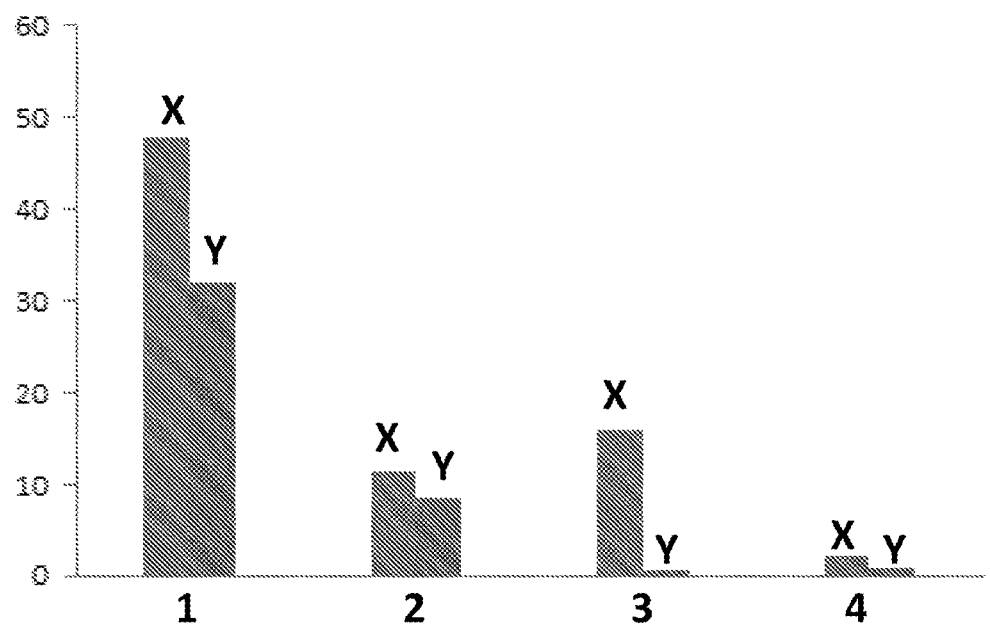
FIG. 6 shows the percentage (y-axis) of single channel MspA nanopores that were no longer active (columns labelled X) and the percentage of channels that were saturated (columns labelled Y) when different beads (1—silane, 2—streptavidin, 3—streptavidin bound with short biotinylated DNA strands, 4—cobalt-based His-Tag Isolation and pulldown) were added to the nanopore system.

FIG. 6 shows the percentage of single channel MspA nanopores that were no longer active and the percentage of channels that were saturated when the beads (1—silane, 2—streptavidin, 3—streptavidin with short, biotinylated DNA strands, 4—cobalt-based his-Tag isolation and pulldown)) were added to the nanopore system. All of the different coated beads resulted in less than 20% loss of MspA nanopores (no longer active nanopores) and less than 10% channel saturation except from silane which resulted in less than 50% loss of MspA nanopores and around 30% channel saturation. As the percentage of channels which saturated after the beads were added was lower than the percentage of MspA nanopores that were no longer active, it was unlikely that the reduction in MspA nanopores was only due to membrane rupture.

Figure 7:
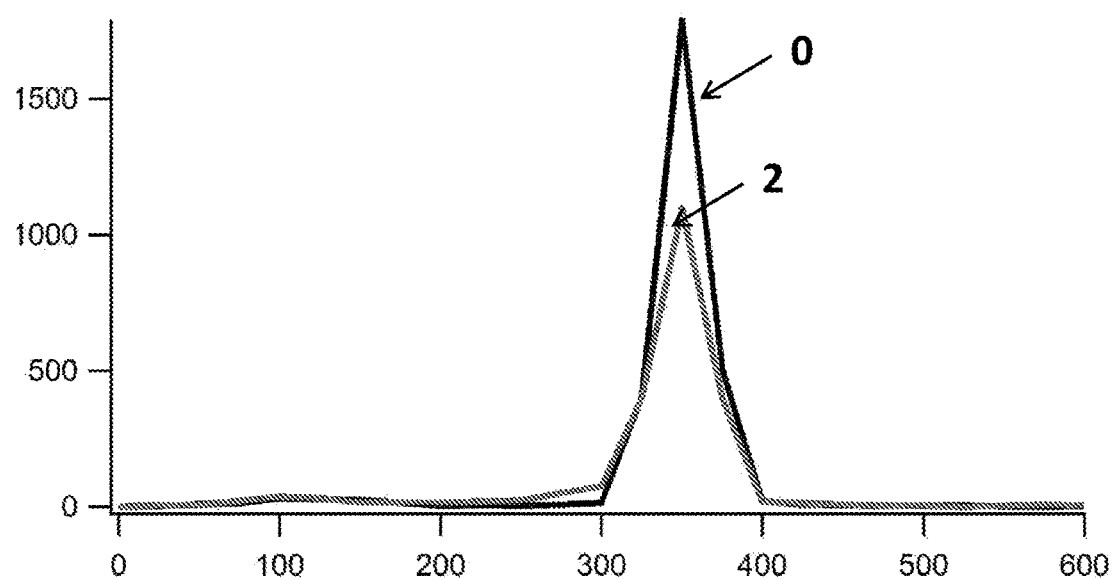
FIG. 7 shows a graph of the number of pores (y-axis) versus the open pore current (x-axis, pA) in the presence of streptavidin coated beads (labelled 2) or in the absence of streptavidin coated beads (labelled 0).

FIG. 7 shows that the open pore current was not affected by the addition of streptavidin coated beads. Line 0 corresponded to the presence of no beads and line 2 corresponded to the presence of streptavidin coated beads both of which result in an open pore current of around 350 pA at an applied potential of 180 mV.

From the data presented in FIGS. 5-7 any of the magnetic bead functionalisations tested (1—silane, 2—streptavidin, 3—streptavidin bound with short biotinylated DNA strands, 4—cobalt-based his-tag Isolation and Pulldown)) could be used to deliver DNA to a nanopore.

Example 4

This example describes how a number of different samples were delivered to the transmembrane protein pore using magnetic microparticles. Sample A was delivered to the transmembrane protein pore (MspA) using magnetic microparticles. This sample was then detected using the nanopore system. Sample A was then removed from the membrane surface using a magnet. The strength of attachment of sample A to the microparticle was greater than the strength of coupling of Sample A to the membrane, therefore, the removal of the microparticle uncoupled sample A from the membrane. Once sample A was removed then Sample B was delivered to the nanopore using magnetic microparticles. This sample was also detected by the nanopore system and was subsequently removed using a magnet. Multiple samples were tested in the nanopore system by using this process.

Materials and Methods 4.1 Preparation of Beads and Attachment of Sample

The magnetic beads were washed in an analogous process to that described in Example 1, step 1.1 above. Samples A and B were attached to the magnetic microparticles in an analogous process to that described in Example 1, step 1.2.

4.2 Electrophysiology

The microparticles with either sample A or B attached were diluted in buffer and fuel mix as described in example 1, step 1.3. The single MspA nanopore was prepared as described in Example 1, step 1.3.

Sample A was added to the nanopore system and helicase controlled DNA movement was monitored. After sufficient data was collected for Sample A then a magnet was placed above the nanopore system for 10 minutes. This attracted the magnetic microparticles towards the magnet and away from the transmembrane protein pores in the membrane. After sample A was removed from the system then magnetic microparticles with Sample B attached were flowed through the nanopore system and helicase controlled DNA movement was monitored. After sufficient data was collected for Sample B then a magnet was placed above the nanopore system for 10 minutes. This attracted the magnetic microparticles, which had sample B attached, towards the magnet and away from the transmembrane protein pores in the membrane. This removed Sample B from the nanopore system which left it available for detection of future samples.

Results

Figure 9:
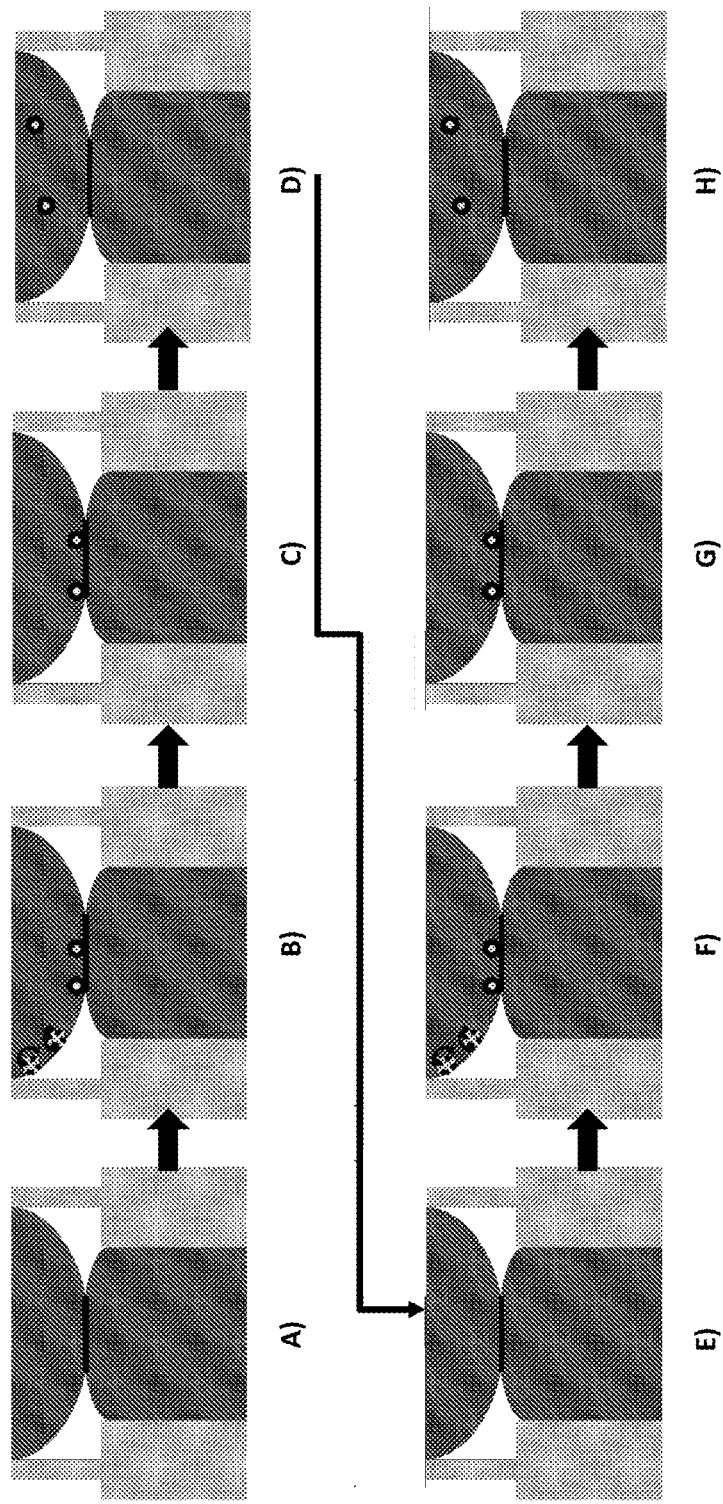
FIG. 9 shows a cartoon schematic of how a DNA sample (A) was delivered on magnetic microparticles, detected and subsequently removed from the nanopore system before a second DNA sample (B) was delivered on magnetic microparticles, detected and subsequently removed from the nanopore system. (A) shows the system with no magnetic microparticles added. (B) shows delivery of sample A using magnetic microparticles. (C) shows sufficient data collection of information from sample A. (D) shows the removal of the microparticle (which was coated in Sample A) from the system, this was done by exposing the magnetic beads to a magnet which uncoupled Sample A from the membrane by removing the magnetic microparticle from the membrane. (E) shows that the system now free of sample A. (F) shows delivery of a second sample B using magnetic microparticles. (G) shows sufficient data collection of information from sample B. (H) shows the removal of the microparticle (which was coated in sample B) from the system, this was done by exposing the magnetic beads to a magnet which uncoupled Sample B from the membrane by removing the magnetic microparticle from the membrane. The above process can be repeated in order to deliver, detect and then remove a large number of samples.

This example showed that using magnetic microparticles it was possible to deliver to, detect and then subsequently remove a number of different samples from the nanopore system. This was possible because the strength of the attachment of samples A and B to the microparticle was greater than the strength of the coupling of Samples A and B to the membrane, therefore, the removal of the microparticle uncoupled samples A and B from the membrane and removed them from the nanopore system. FIG. 9 shows a cartoon representation of the steps described in 4.2 above.

Example 5

This example describes the sample preparation procedure for attaching a DNA molecule, to Dynabeads® MyOne™ Streptavidin C1 (ThermoFisher Scientific Product No: 65001) and then adding the beads to a nanopore system in order to detect helicase-controlled DNA movement. The DNA was hybridised to "anchoring" oligonucleotides: one oligo was hybridised to the Y-adapter and assisted in delivering the DNA onto the nanopore in the membrane; and the second oligo, which was hybridised to the hairpin adapter, contained a biotin moiety that facilitated the binding of the DNA molecule to the magnetic bead (See FIG. 10).

Materials and Methods

Wash Treatment of the MyOne C1 Dynabeads®

The stock sample which contained the MyOne C1 Dynabeads® was vortexed in order to thoroughly re-suspend the Dynabeads® throughout the solution. A sample of the bead solution (1 µL) was removed from the stock solution and added to an Eppendorf DNA LoBind tube (1.5 mL). The tube was placed on a magnetic rack and the supernatant removed once all of the beads had stuck to the magnet. Binding buffer (provided as part of Thermofisher Kit, Catalog No. 60101) was added (40 µL) to the magnetic bead sample (Dynabeads® kilobaseBINDER™ kit) and the beads were re-suspended by vortexing. The tube was then placed on the magnetic rack and the supernatant removed once the beads had stuck to the magnet. The buffer wash and supernatant removal steps were repeated a further two times so that the beads had been washed a total of three times using the buffer and this was known as the washed bead stock solution. Before use the bead stock solution was vortexed in order to thoroughly re-suspend the Dynabeads® throughout the solution.

Attachment of DNA (with Pre-Bound Helicase) to the Dynabeads®

Figure 10:
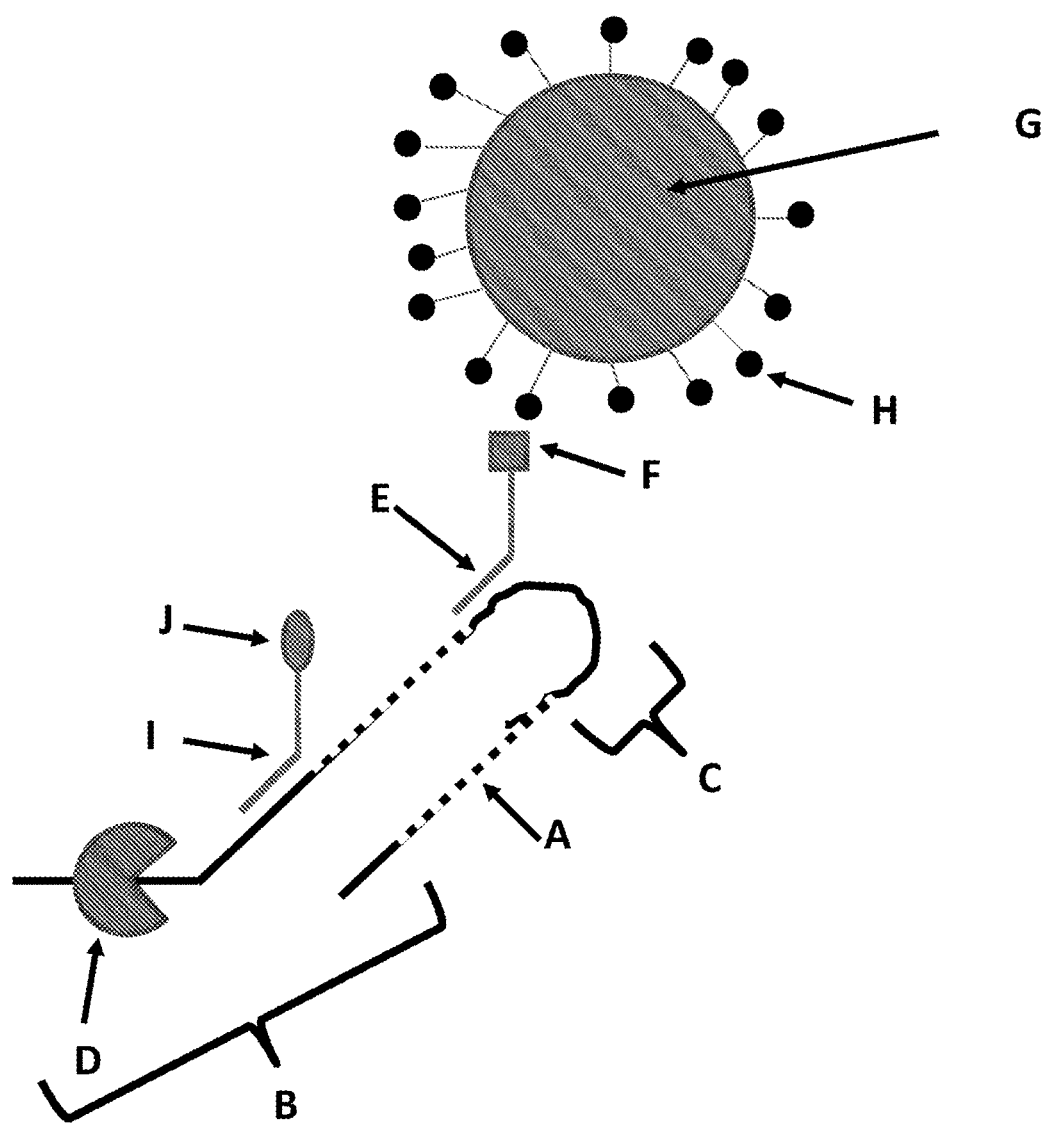
FIG. 10 shows a cartoon representation (not to scale) of how the DNA was attached to the Dynabead® in Example 5. The double-stranded DNA (dsDNA) sample was obtained by the fragmentation of lambda DNA, (shown as a dotted line and labelled A) and has a Y-adapter (labelled B) and a hairpin adapter (labelled C) attached to either end of the lambda DNA. The helicase that binds to the Y-adapter is labelled D. The oligonucleotide which hybridized to the hairpin adapter is shown (labelled E) and contained a biotin moiety (labelled F). When the MyOne C1 Dynabeads® (labelled G) were pre-incubated with the dsDNA sample, the streptavidin on the surface of the bead (shown as a black circles and labelled H) would bind to the biotin. The dsDNA sample also had an additional anchor (labelled J) which was attached to DNA strand (labelled I) that was hybridised to the Y adapter: this was used to associate the DNA with the membrane. This figure shows the attachment of a single dsDNA sample however the bead is covered in streptavidin so it is likely to bind multiple dsDNA samples on a single bead.

A DNA library (which contained double-stranded lambda DNA which had been fragmented and then attached to a Y-adapter (which had a helicase attached to the leader) and a hairpin adapter and was then hybridised to two anchoring oligonucleotides (as shown in FIG. 10)) was added to the washed Dynabeads® (see Table 6 below) and the sample incubated at room temperature for 15 minutes (with mixing). After 15 minutes, the sample was placed on a magnetic rack to pellet the beads. The supernatant was removed and the beads were washed with 80 µL Wash buffer (2M NaCl, 10 mM Tris.HCl (pH 7.5), 1 mM EDTA) (Dynabeads® kilobaseBINDER™ kit). The wash buffer was removed and the wash step was repeated. Finally, the washed and pelleted beads were re-suspended in 12 µL 500 mM KCl, pH 8.0, 25 mM potassium phosphate buffer. This sample was DNA/bead sample 3.

TABLE 6

| Reagent | Volume (µL) |
|---|---|
| DNA Library | 30 |
| Washed Dynabeads ® produced in step 1.1 | 30 |
| Total | 60 |

Electrophysiology

Prior to setting up the experiment, DNA/bead sample 3 (3 µL) was added to buffer (143 µL, 25 mM Potassium Phosphate buffer, pH 8.0, 500 mM KCl) and fuel mix (4 µL of MgCl2 (75 mM) and ATP (75 mM)).

Electrical measurements were acquired from single MspA nanopores inserted in block co-polymer in buffer (25 mM potassium phosphate buffer, 150 mM potassium ferrocyanide (II), and 150 mM potassium ferricyanide (III), pH 8.0). After achieving a single pore inserted in the block co-polymer, then buffer (2 mL, 25 mM K Phosphate buffer, 150 mM Potassium Ferrocyanide (II), 150 mM Potassium Ferricyanide (III), pH 8.0) was flowed through the system to remove any excess MspA nanopores.

An excess of buffer (500 mM KCl, 25 mM potassium phosphate, pH 8.0) was flowed through the nanopore system prior to adding the sample. The DNA/bead sample 3 and fuel pre-mix (155 µL total) was then flowed into the single nanopore experimental system. The experiment was run at −120 mV and helicase-controlled DNA movement monitored.

Results

Helicase controlled DNA movement was observed for the DNA/bead sample 3. The DNA library which was pre-incubated with Dynabeads® MyOne™ Streptavidin C1 (ThermoFisher Scientific Product No: 65001) exhibited a similar concentration enhancement as that observed in example 1 using the His-tagged beads. This meant that the Dynabeads® assisted in delivering DNA directly to the nanopore system.

Example 6

This example shows how samples attached to beads can be removed from the nanopore chip array by physically removing the beads from the flowcell using a buffer flush.

Materials and Methods

Figure 11:
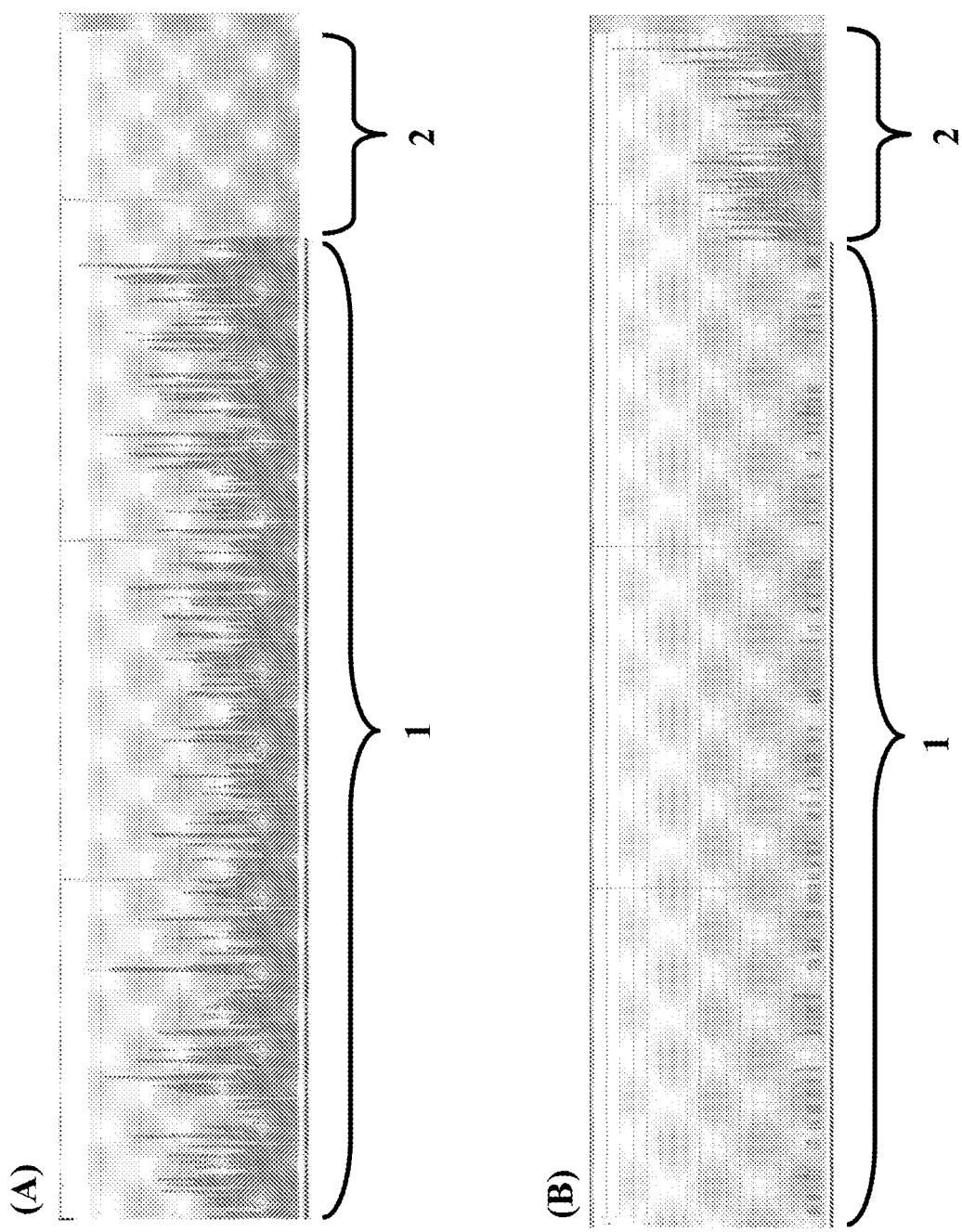
FIG. 11 shows two plots (y-axis=depth of coverage and x-axis=number of DNA bases in the polynucleotide sequence of samples 1 (see region labelled 1) and 2 (see region labelled 2)) which show the depth of coverage of samples A and B during the experiment described in Example 6. The depth of coverage relates to the number of instances when that position in the DNA sequence has been mapped and identified in a helicase controlled DNA movement. Section (A) shows the depth of coverage when only sample 1 was added to the nanopore system and Section (B) shows the depth of coverage when sample A had been washed from the system and sample B had been added to the system. The DNA sequence of sample 1 was much longer than the DNA sequence of sample 2. The depth of coverage for Sample 1 was very low after the beads (to which sample 1 are attached) had been flushed from the system and beads with sample 2 have been added.
Figure 12:
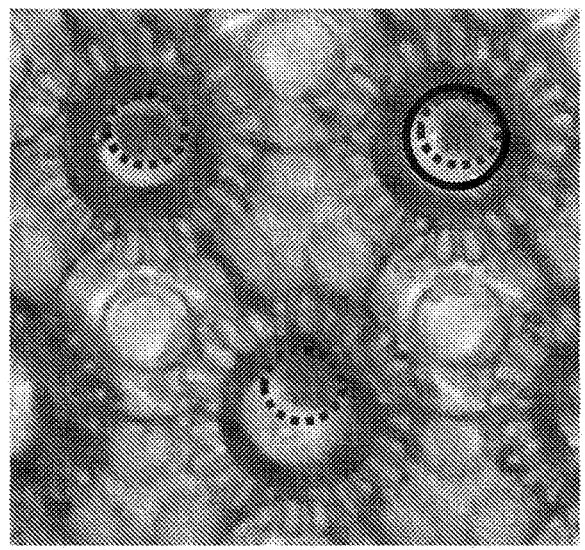
FIG. 12 shows two microscope images of the same region of the nanopore chip system. (A) shows a microscope image of the nanopore chip system after the addition of sample A attached to beads. Large clusters of Dynabeads® (highlighted in the figure by white dashed line circles) were observed on the region of the chip where the membrane formed (this region is highlighted on one of the wells by a black circle). (B) shows a microscope image of the nanopore chip system after the nanopore system had been flushed using 3×1 ml volumes of buffer. No beads were visible on the region of the chip where the membrane formed.
Figure 12:
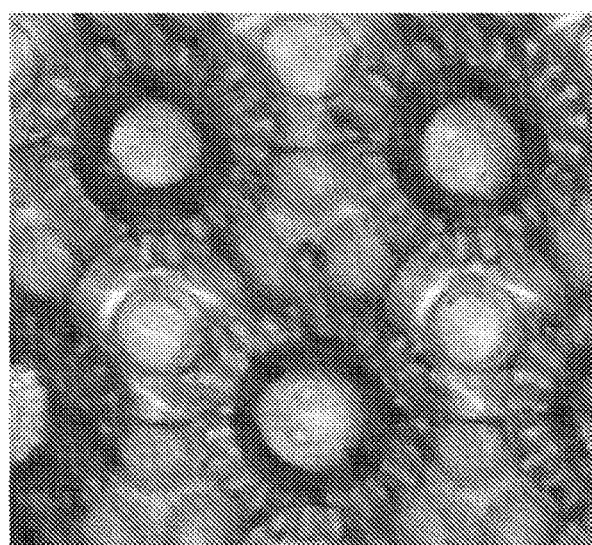

DNA samples from two separate organisms were prepared individually and attached to His-tag isolation and pulldown magnetic beads as described in Example 1 (see 1.1 and 1.2). The sample prepared from the first organism (sample A) was added to the nanopore system as described in Example 1.3 and helicase controlled DNA movement of the DNA from the first organism was monitored for 1 hr. The nanopore array system was then flushed using 3×1 ml volumes of buffer in order to flush the beads out of the system. The sample prepared from the second organism (sample B) was then added to the nanopore system as described in Example 1.3 and helicase controlled DNA movement of the DNA from the second organism was monitored for 1 hr. The helicase controlled DNA movements were mapped to a reference consisting of the two genomes (see FIG. 11). FIG. 11(A) shows the depth coverage for the experiment when only sample A was present in the system and FIG. 11(B) shows the depth coverage for the second hour of the experiment after buffer had been flushed through the system and sample B had been added. The mapping indicated that a simple buffer flush removed most of sample A from the nanopore system. Further flushes could be performed on the system in order to increase the number of beads with sample A attached that were removed from the system. FIG. 12 shows magnified images of the same region of the nanopore system after addition of sample A (FIG. 12A) and after the 3×1 ml buffer flush. FIG. 12A shows the beads concentrated on the region of the nanopore system where the membrane forms and FIG. 12B shows that the beads have been removed from the system after the buffer flush.

Example 7

This example shows how workflows can be improved to maximise throughput for low-input samples (<100 ng starting material), without the need for PCR.

Figure 13A:
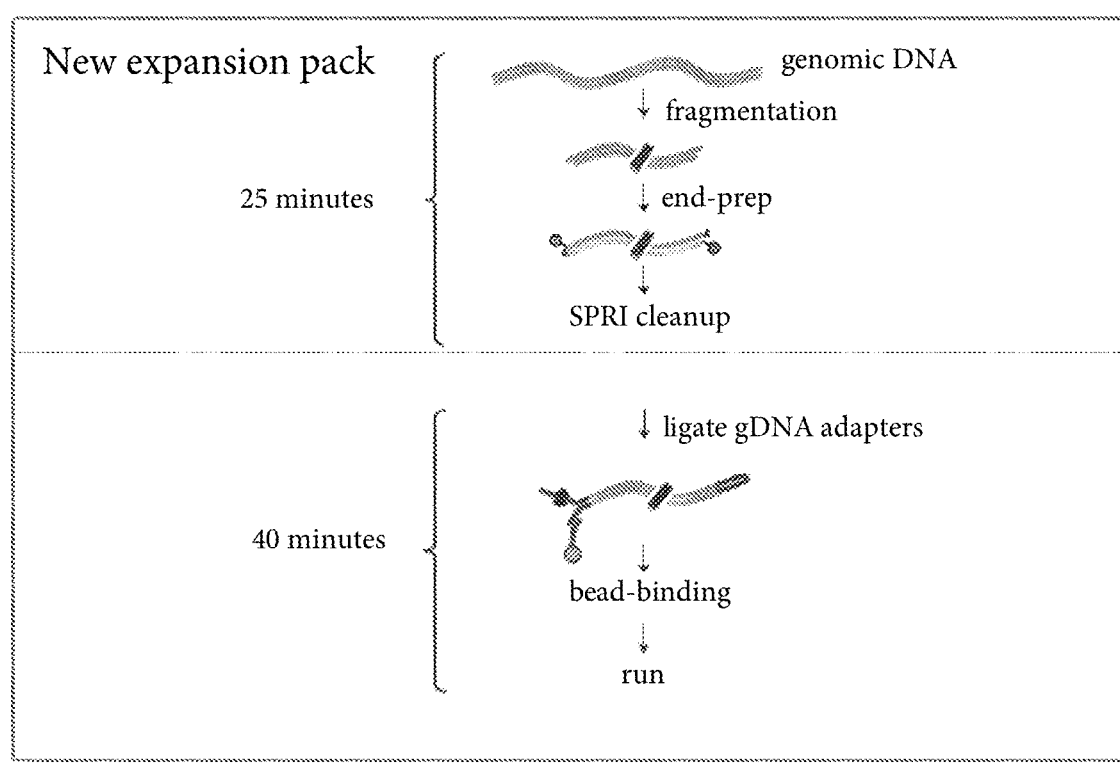
FIG. 13A shows a schematic representation of the low-input protocol described in Example 7.

Materials and Methods:

FIG. 13A shows as schematic representation of the new low-input protocol. In this protocol the library was loaded onto the nanopore system for analysis while strands were still bound to the beads.

Figure 13B:
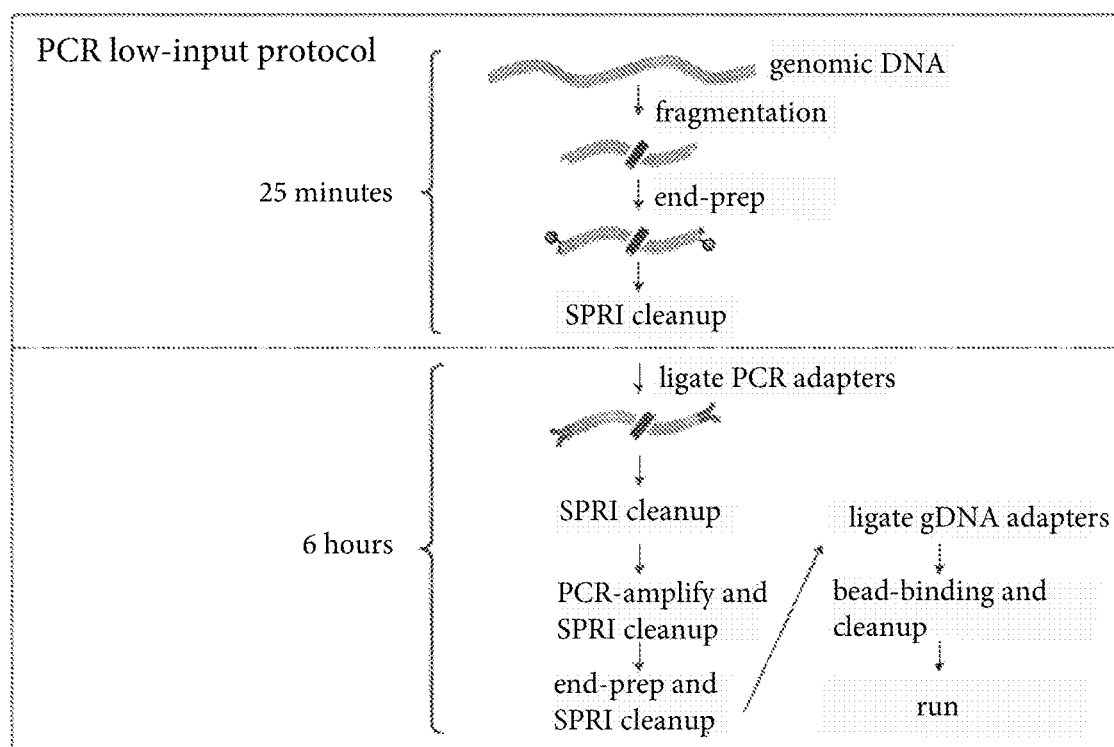
FIG. 13B shows a schematic representation of a PCR-based low-input protocol (referred to in Example 7).

In contrast, FIG. 13B shows a schematic representation of a PCR-based low-input protocol. The final steps of the PCR-based protocol are protracted: The user needs to clean the prepared sequencing library using streptavidin beads and to elute the library from the beads before loading onto the nanopore system for analysis.

Results:

In the new low-input protocol, gravity was used to draw the beads onto the membrane surface, increasing the local concentration of DNA molecules on the membrane. This improved the sensitivity of the system by over an order of magnitude, allowing us to lower the input requirement from 1 µg to 0.025 µg (25 ng). Omitting the PCR step meant that amplification bias was eliminated and several hours of laboratory time were saved. A PCR-free protocol is compatible with longer fragments, giving longer reads. Additionally epigenetic modifications are preserved. When used on genomic DNA which has been sheared to approximately 8 kb, the 2D read-length distribution form the new low-input protocol was similar to the fragment-length distribution of the input DNA. This indicates that bead-loading does not introduce any noticeable fragment-length bias.

Example 8

This example shows how sequence capture allows for enrichment of loci of interest prior to sequencing and thus more efficient use of the sequencing run.

Figure 14:
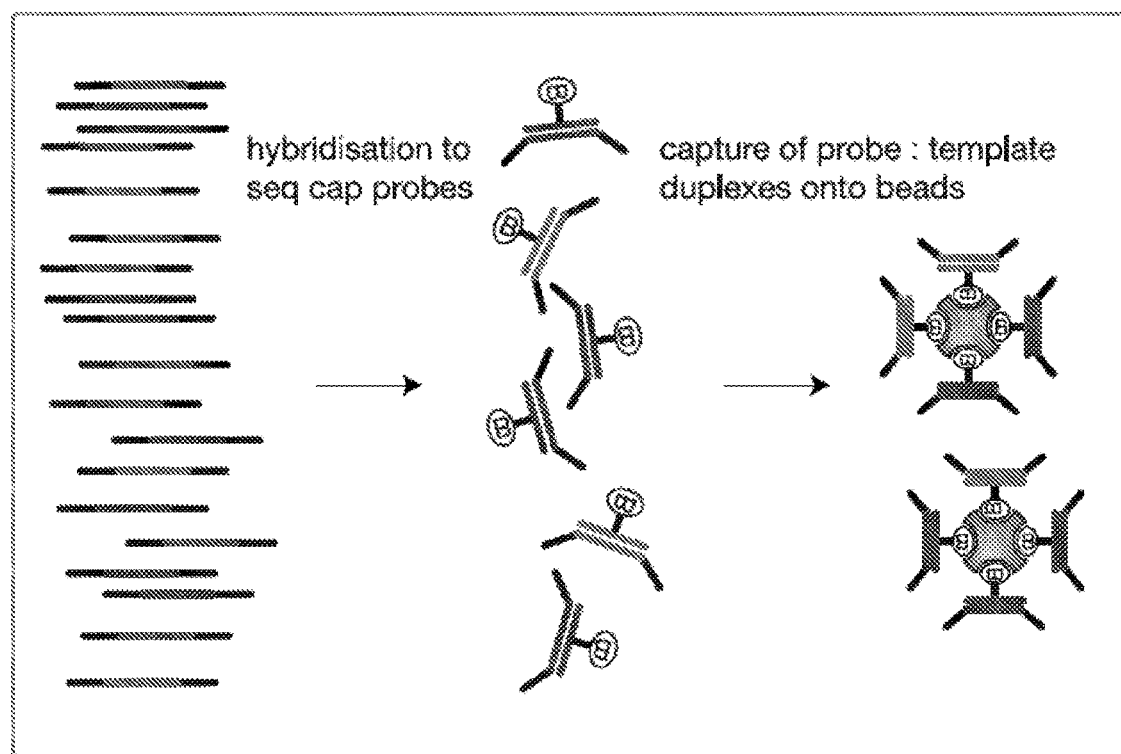
FIG. 14 illustrates a sequence capture workflow as described in Example 8.

Materials and Methods:

Sequence capture was performed during library preparation by hybridising the library fragments to probes which are specific to the regions of interest (See FIG. 14). A custom probeset was designed which was specific to the lambda phage genome, consisting of 120 nt oligos tiled at 1-base intervals and which was synthesised by Agilent. Lambda genomic DNA was mixed with *E. coli* DNA with the genomes mixed in equimolar ratios. The genomic DNA was fragmented to approx 2 kb using Fragmentase. Sequence capture was performed following Agilent's standard Sure-Select protocol, with PCR extension times adjusted to accounts for the longer fragments. The resulting library was then analysed using the nanopore system.

Results:

Lambda DNA constituted approximately 1% of the starting DNA but after capture we obtained 70% of reads on target.

Sequence capture is useful when analysis of the entire genome is not desired or where the genome is too large for the throughput of the sequencer. The regions of interest may be longer in total than would be realistic to enrich by PCR, or too many PCRs may be required. Sequence capture saves money and time on sequencing and data analysis.

The invention claimed is:

1. A method for delivering an increased concentration of a polynucleotide analyte to a transmembrane pore in a membrane, comprising:
   (a) providing the polynucleotide analyte attached to a microparticle;
   (b) delivering the microparticle towards the membrane, thereby delivering the polynucleotide analyte to the transmembrane pore;
   (c) allowing the polynucleotide analyte to interact with the transmembrane pore under conditions in which a polynucleotide binding protein, bound to the polynucleotide analyte, controls movement of the polynucleotide analyte, wherein the polynucleotide analyte is eluted from the microparticle and moves with respect to the transmembrane pore, wherein the concentration of the polynucleotide analyte delivered to the transmembrane pore is increased by at least about 10-fold; and
   (d) taking measurements as the polynucleotide moves with respect to the pore, wherein the measurements are indicative of characteristics of the polynucleotide, and thereby characterising the polynucleotide.

2. The method of claim 1, wherein step (b) comprises positioning the microparticle near to or adjacent to the membrane and allowing the microparticle to move towards the membrane.

3. The method of claim 1, wherein the method comprises (a) allowing the microparticle to move along an electrochemical gradient, diffusion gradient, hydrophilic gradient or hydrophobic gradient (b) allowing the microparticle to move within a magnetic field; (c) allowing the microparticle to move within an electrical field; (d) allowing the microparticle to move under pressure; or (e) allowing the microparticle to move with gravity.

4. The method of claim 1, wherein 2, 3, 4, 5, 6, 7, 8, 9, 10, 20, 30, 50, 100, 500, 1,000, 5,000, 10,000, 100,000, 1,000,000, or 5,000,000 polynucleotide analytes are attached to the microparticle.

5. The method of claim 1, wherein the polynucleotide analyte comprises an anchor which are capable of coupling to the membrane.

6. The method of claim 5, wherein the method further comprises coupling the polynucleotide analyte to the membrane using the the anchor.

7. The method of claim 5, wherein the anchor comprises a polypeptide anchor and/or a hydrophobic anchor.

8. The method of claim 7, wherein the hydrophobic anchor comprises a lipid, fatty acid, sterol, carbon nanotube or amino acid.

9. The method of claim 5, wherein the anchor comprises a linker.

10. The method of claim 5, wherein the polynucleotide analyte is coupled transiently to the membrane.

11. The method of claim 1, wherein the polynucleotide analyte is attached to the microparticle via hybridisation.

12. The method according to claim 1, wherein the membrane is an amphiphilic layer or a solid state layer.

13. The method of claim 1, wherein the microparticle is formed from a ceramic, glass, silica, a polymer or a metal.

14. The method of claim 1, wherein the microparticle is 500 μm in diameter or less.

15. The method of claim 1, wherein the microparticle is magnetic.

16. The method of claim 1, wherein the transmembrane pore is a transmembrane protein pore.

17. The method of claim 16, wherein the transmembrane protein pore is derived from *Mycobacterium smegmatis* porin (Msp), α-hemolysin (α-HL) or lysenin.

18. The method of claim 1, wherein the characteristics are selected from (i) the length of the polynucleotide, (ii) the identity of the polynucleotide, (iii) the sequence of the polynucleotide, (iv) the secondary structure of the polynucleotide and (v) whether or not the polynucleotide is modified.

19. The method of claim 1, wherein the characteristics of the polynucleotide are measured by electrical measurement and/or optical measurement.

20. The method of claim 19, wherein the electrical measurement is a current measurement, an impedance measurement, a tunnelling measurement or a field effect transistor (FET) measurement.

21. The method of claim 1, wherein the polynucleotide binding protein is derived from a helicase.

22. The method of claim 1, wherein the method further comprises removing the microparticle from the membrane.

23. The method of claim 22, wherein the method further comprises removing the microparticle from the membrane using a magnetic field or a flow-based method.

24. The method of claim 22, wherein the method further comprises
   (e) providing a second polynucleotide analyte in a second sample attached to a second microparticle after removal of the first microparticle from the membrane;
   (f) delivering the second microparticle towards the membrane and thereby delivering the second polynucleotide analyte to the transmembrane pore.

25. The method of claim 24, wherein the method further comprises, after step (f), allowing the second polynucleotide analyte to interact with the transmembrane pore and taking the measurements during the interaction, wherein the measurements are indicative of the presence, absence or characteristics of the second polynucleotide analyte.

\* \* \* \* \*

SEQUENCE LISTING

<160> NUMBER OF SEQ ID NOS: 25

<210> SEQ ID NO 1
<211> LENGTH: 558
<212> TYPE: DNA
<213> ORGANISM: Artificial Sequence
<220> FEATURE:
<223> OTHER INFORMATION: Synthetic polynucleotide

<400> SEQUENCE: 1

```
atgggtctgg ataatgaact gagcctggtg gacggtcaag atcgtaccct gacggtgcaa      60
caatgggata cctttctgaa tggcgttttt ccgctggatc gtaatcgcct gacccgtgaa     120
tggtttcatt ccggtcgcgc aaaatatatc gtcgcaggcc cgggtgctga cgaattcgaa     180
ggcacgctgg aactgggtta tcagattggc tttccgtggt cactgggcgt tggtatcaac     240
ttctcgtaca ccacgccgaa tattctgatc aacaatggta acattaccgc accgccgttt     300
ggcctgaaca gcgtgattac gccgaacctg tttccgggtg ttagcatctc tgcccgtctg     360
ggcaatggtc cgggcattca agaagtggca acctttagtg tgcgcgtttc cggcgctaaa     420
ggcggtgtcg cggtgtctaa cgcccacggt accgttacgg gcgcggccgg cggtgtcctg     480
ctgcgtccgt tcgcgcgcct gattgcctct accggcgaca gcgttacgac ctatggcgaa     540
ccgtggaata tgaactaa                                                   558
```

<210> SEQ ID NO 2
<211> LENGTH: 184
<212> TYPE: PRT
<213> ORGANISM: Artificial Sequence
<220> FEATURE:
<223> OTHER INFORMATION: Synthetic polypeptide

<400> SEQUENCE: 2

```
Gly Leu Asp Asn Glu Leu Ser Leu Val Asp Gly Gln Asp Arg Thr Leu
1               5                   10                  15

Thr Val Gln Gln Trp Asp Thr Phe Leu Asn Gly Val Phe Pro Leu Asp
            20                  25                  30

Arg Asn Arg Leu Thr Arg Glu Trp Phe His Ser Gly Arg Ala Lys Tyr
        35                  40                  45

Ile Val Ala Gly Pro Gly Ala Asp Glu Phe Glu Gly Thr Leu Glu Leu
    50                  55                  60

Gly Tyr Gln Ile Gly Phe Pro Trp Ser Leu Val Gly Ile Asn Phe
65                  70                  75                  80

Ser Tyr Thr Thr Pro Asn Ile Leu Ile Asn Asn Gly Asn Ile Thr Ala
                85                  90                  95

Pro Pro Phe Gly Leu Asn Ser Val Ile Thr Pro Asn Leu Phe Pro Gly
            100                 105                 110

Val Ser Ile Ser Ala Arg Leu Gly Asn Gly Pro Gly Ile Gln Glu Val
            115                 120                 125

Ala Thr Phe Ser Val Arg Val Ser Gly Ala Lys Gly Gly Val Ala Val
        130                 135                 140

Ser Asn Ala His Gly Thr Val Thr Gly Ala Ala Gly Gly Val Leu Leu
145                 150                 155                 160

Arg Pro Phe Ala Arg Leu Ile Ala Ser Thr Gly Asp Ser Val Thr Thr
                165                 170                 175

Tyr Gly Glu Pro Trp Asn Met Asn
            180
```

```
<210> SEQ ID NO 3
<211> LENGTH: 885
<212> TYPE: DNA
<213> ORGANISM: Artificial Sequence
<220> FEATURE:
<223> OTHER INFORMATION: Synthetic polynucleotide

<400> SEQUENCE: 3
atggcagatt ctgatattaa tattaaaacc ggtactacag atattggaag caatactaca      60
gtaaaaacag gtgatttagt cacttatgat aaagaaaatg gcatgcacaa aaaagtattt     120
tatagtttta tcgatgataa aaatcacaat aaaaaactgc tagttattag aacaaaaggt     180
accattgctg gtcaatatag agtttatagc gaagaaggtg ctaacaaaag tggtttagcc     240
tggccttcag cctttaaggt acagttgcaa ctacctgata tgaagtagc tcaaatatct      300
gattactatc caagaaattc gattgataca aaaaactata tgagtacttt aacttatgga     360
ttcaacggta atgttactgg tgatgataca ggaaaaattg gcggccttat tggtgcaaat     420
gtttcgattg tcatacact gaactatgtt caacctgatt tcaaaacaat tttagagagc      480
ccaactgata aaaagtagg ctggaaagtg atatttaaca atatggtgaa tcaaaattgg      540
ggaccatacg atcgagattc ttggaacccg gtatatggca atcaactttt catgaaaact     600
agaaatggtt ctatgaaagc agcagataac ttccttgatc ctaacaaagc aagttctcta     660
ttatcttcag ggttttcacc agacttcgct acagttatta ctatggatag aaaagcatcc     720
aaacaacaaa caaatataga tgtaatatac gaacgagttc gtgatgatta ccaattgcat     780
tggacttcaa caaattggaa aggtaccaat actaaagata aatggacaga tcgttcttca     840
gaaagatata aaatcgattg ggaaaaagaa gaaatgacaa attaa                     885
```

```
<210> SEQ ID NO 4
<211> LENGTH: 293
```

```
<212> TYPE: PRT
<213> ORGANISM: Artificial Sequence
<220> FEATURE:
<223> OTHER INFORMATION: Synthetic polypeptide

<400> SEQUENCE: 4

Ala Asp Ser Asp Ile Asn Ile Lys Thr Gly Thr Thr Asp Ile Gly Ser
1               5                   10                  15

Asn Thr Thr Val Lys Thr Gly Asp Leu Val Thr Tyr Asp Lys Glu Asn
                20                  25                  30

Gly Met His Lys Lys Val Phe Tyr Ser Phe Ile Asp Asp Lys Asn His
            35                  40                  45

Asn Lys Lys Leu Leu Val Ile Arg Thr Lys Gly Thr Ile Ala Gly Gln
50                  55                  60

Tyr Arg Val Tyr Ser Glu Glu Gly Ala Asn Lys Ser Gly Leu Ala Trp
65                  70                  75                  80

Pro Ser Ala Phe Lys Val Gln Leu Gln Leu Pro Asp Asn Glu Val Ala
                85                  90                  95

Gln Ile Ser Asp Tyr Tyr Pro Arg Asn Ser Ile Asp Thr Lys Asn Tyr
                100                 105                 110

Met Ser Thr Leu Thr Tyr Gly Phe Asn Gly Asn Val Thr Gly Asp Asp
            115                 120                 125

Thr Gly Lys Ile Gly Gly Leu Ile Gly Ala Asn Val Ser Ile Gly His
130                 135                 140

Thr Leu Asn Tyr Val Gln Pro Asp Phe Lys Thr Ile Leu Glu Ser Pro
145                 150                 155                 160

Thr Asp Lys Lys Val Gly Trp Lys Val Ile Phe Asn Asn Met Val Asn
                165                 170                 175

Gln Asn Trp Gly Pro Tyr Asp Arg Asp Ser Trp Asn Pro Val Tyr Gly
                180                 185                 190

Asn Gln Leu Phe Met Lys Thr Arg Asn Gly Ser Met Lys Ala Ala Asp
            195                 200                 205

Asn Phe Leu Asp Pro Asn Lys Ala Ser Ser Leu Leu Ser Ser Gly Phe
210                 215                 220

Ser Pro Asp Phe Ala Thr Val Ile Thr Met Asp Arg Lys Ala Ser Lys
225                 230                 235                 240

Gln Gln Thr Asn Ile Asp Val Ile Tyr Glu Arg Val Arg Asp Asp Tyr
                245                 250                 255

Gln Leu His Trp Thr Ser Thr Asn Trp Lys Gly Thr Asn Thr Lys Asp
            260                 265                 270

Lys Trp Thr Asp Arg Ser Ser Glu Arg Tyr Lys Ile Asp Trp Glu Lys
                275                 280                 285

Glu Glu Met Thr Asn
        290

<210> SEQ ID NO 5
<211> LENGTH: 184
<212> TYPE: PRT
<213> ORGANISM: Mycobacterium smegmatis

<400> SEQUENCE: 5

Gly Leu Asp Asn Glu Leu Ser Leu Val Asp Gly Gln Asp Arg Thr Leu
1               5                   10                  15

Thr Val Gln Gln Trp Asp Thr Phe Leu Asn Gly Val Phe Pro Leu Asp
                20                  25                  30

Arg Asn Arg Leu Thr Arg Glu Trp Phe His Ser Gly Arg Ala Lys Tyr
```

```
                35                  40                  45
Ile Val Ala Gly Pro Gly Ala Asp Glu Phe Glu Gly Thr Leu Glu Leu
 50                  55                  60
Gly Tyr Gln Ile Gly Phe Pro Trp Ser Leu Gly Val Gly Ile Asn Phe
 65                  70                  75                  80
Ser Tyr Thr Thr Pro Asn Ile Leu Ile Asp Asp Gly Asp Ile Thr Ala
                 85                  90                  95
Pro Pro Phe Gly Leu Asn Ser Val Ile Thr Pro Asn Leu Phe Pro Gly
                100                 105                 110
Val Ser Ile Ser Ala Asp Leu Gly Asn Gly Pro Gly Ile Gln Glu Val
                115                 120                 125
Ala Thr Phe Ser Val Asp Val Ser Gly Pro Ala Gly Val Ala Val
                130                 135                 140
Ser Asn Ala His Gly Thr Val Thr Gly Ala Ala Gly Val Leu Leu
145                 150                 155                 160
Arg Pro Phe Ala Arg Leu Ile Ala Ser Thr Gly Asp Ser Val Thr Thr
                165                 170                 175
Tyr Gly Glu Pro Trp Asn Met Asn
                180

<210> SEQ ID NO 6
<211> LENGTH: 184
<212> TYPE: PRT
<213> ORGANISM: Mycobacterium smegmatis

<400> SEQUENCE: 6

Gly Leu Asp Asn Glu Leu Ser Leu Val Asp Gly Gln Asp Arg Thr Leu
  1               5                  10                  15
Thr Val Gln Gln Trp Asp Thr Phe Leu Asn Gly Val Phe Pro Leu Asp
                 20                  25                  30
Arg Asn Arg Leu Thr Arg Glu Trp Phe His Ser Gly Arg Ala Lys Tyr
                 35                  40                  45
Ile Val Ala Gly Pro Gly Ala Asp Glu Phe Glu Gly Thr Leu Glu Leu
 50                  55                  60
Gly Tyr Gln Ile Gly Phe Pro Trp Ser Leu Gly Val Gly Ile Asn Phe
 65                  70                  75                  80
Ser Tyr Thr Thr Pro Asn Ile Leu Ile Asp Asp Gly Asp Ile Thr Gly
                 85                  90                  95
Pro Pro Phe Gly Leu Glu Ser Val Ile Thr Pro Asn Leu Phe Pro Gly
                100                 105                 110
Val Ser Ile Ser Ala Asp Leu Gly Asn Gly Pro Gly Ile Gln Glu Val
                115                 120                 125
Ala Thr Phe Ser Val Asp Val Ser Gly Pro Ala Gly Val Ala Val
                130                 135                 140
Ser Asn Ala His Gly Thr Val Thr Gly Ala Ala Gly Val Leu Leu
145                 150                 155                 160
Arg Pro Phe Ala Arg Leu Ile Ala Ser Thr Gly Asp Ser Val Thr Thr
                165                 170                 175
Tyr Gly Glu Pro Trp Asn Met Asn
                180

<210> SEQ ID NO 7
<211> LENGTH: 183
<212> TYPE: PRT
<213> ORGANISM: Mycobacterium smegmatis
```

<400> SEQUENCE: 7

```
Val Asp Asn Gln Leu Ser Val Val Asp Gly Gln Gly Arg Thr Leu Thr
1               5                   10                  15

Val Gln Gln Ala Glu Thr Phe Leu Asn Gly Val Phe Pro Leu Asp Arg
            20                  25                  30

Asn Arg Leu Thr Arg Glu Trp Phe His Ser Gly Arg Ala Thr Tyr His
        35                  40                  45

Val Ala Gly Pro Gly Ala Asp Glu Phe Glu Gly Thr Leu Glu Leu Gly
    50                  55                  60

Tyr Gln Val Gly Phe Pro Trp Ser Leu Gly Val Gly Ile Asn Phe Ser
65                  70                  75                  80

Tyr Thr Thr Pro Asn Ile Leu Ile Asp Gly Asp Ile Thr Gln Pro
                85                  90                  95

Pro Phe Gly Leu Asp Thr Ile Ile Thr Pro Asn Leu Phe Pro Gly Val
                100                 105                 110

Ser Ile Ser Ala Asp Leu Gly Asn Gly Pro Gly Ile Gln Glu Val Ala
            115                 120                 125

Thr Phe Ser Val Asp Val Lys Gly Ala Lys Gly Ala Val Ala Val Ser
130                 135                 140

Asn Ala His Gly Thr Val Thr Gly Ala Ala Gly Gly Val Leu Leu Arg
145                 150                 155                 160

Pro Phe Ala Arg Leu Ile Ala Ser Thr Gly Asp Ser Val Thr Thr Tyr
                165                 170                 175

Gly Glu Pro Trp Asn Met Asn
                180
```

<210> SEQ ID NO 8
<211> LENGTH: 1830
<212> TYPE: DNA
<213> ORGANISM: Bacillus subtilis phage phi29

<400> SEQUENCE: 8

```
atgaaacaca tgccgcgtaa aatgtatagc tgcgcgtttg aaaccacgac caaagtggaa      60
gattgtcgcg tttgggccta tggctacatg aacatcgaag atcattctga atacaaaatc    120
ggtaacagtc tggatgaatt tatggcatgg gtgctgaaag ttcaggcgga tctgtacttc    180
cacaacctga aatttgatgg cgcattcatt atcaactggc tggaacgtaa tggctttaaa    240
tggagcgcgg atggtctgcc gaacacgtat aataccatta tctctcgtat gggccagtgg    300
tatatgattg atatctgcct gggctacaaa ggtaaacgca aaattcatac cgtgatctat    360
gatagcctga aaaactgcc gtttccggtg aagaaaattg cgaaagattt caaactgacg    420
gttctgaaag cgatattga ttatcacaaa gaacgtccgg ttggttacaa aatcaccccg    480
gaagaatacg catacatcaa aaacgatatc cagatcatcg cagaagcgct gctgattcag    540
tttaaacagg gcctggatcg catgaccgcg ggcagtgata gcctgaaagg tttcaaagat    600
atcatcacga ccaaaaaatt caaaaaagtg ttcccgacgc tgagcctggg tctggataaa    660
gaagttcgtt atgcctaccg cggcggtttt acctggctga cgatcgttt caagaaaaaa    720
gaaattggcg agggtatggt gtttgatgtt aatagtctgt atccggcaca gatgtacagc    780
cgcctgctgc gtatggcga accgatcgtg ttcgagggta aatatgtttg ggatgaagat    840
tacccgctgc atattcagca catccgttgt gaatttgaac tgaaagaagg ctatattccg    900
accattcaga tcaaacgtag tcgcttctat aagggtaacg aatacctgaa agctctggc    960
ggtgaaatcg cggatctgtg gctgagtaac gtggatctgg aactgatgaa agaacactac   1020
```

```
gatctgtaca acgttgaata catcagcggc ctgaaattta aagccacgac cggtctgttc    1080
aaagatttca tcgataaatg gacctacatc aaaacgacct ctgaaggcgc gattaaacag    1140
ctggccaaac tgatgctgaa cagcctgtat ggcaaattcg cctctaatcc ggatgtgacc    1200
ggtaaagttc gtacctgaa agaaaatggc gcactgggtt ttcgcctggg cgaagaagaa     1260
acgaaagatc cggtgtatac cccgatgggt gttttcatta cggcctgggc acgttacacg    1320
accatcaccg cggcccaggc atgctatgat cgcattatct actgtgatac cgattctatt    1380
catctgacgg gcaccgaaat cccggatgtg attaagata tcgttgatcc gaaaaaactg     1440
ggttattggg cccacgaaag tacgtttaaa cgtgcaaaat acctgcgcca gaaaacctac    1500
atccaggata tctacatgaa agaagtggat ggcaaactgg ttgaaggttc tccggatgat    1560
tacaccgata tcaaattcag tgtgaaatgc gccggcatga cggataaaat caaaaaagaa    1620
gtgaccttcg aaaacttcaa agttggtttc agccgcaaaa tgaaaccgaa accggtgcag    1680
gttccgggcg gtgtggttct ggtggatgat acgtttacca ttaaatctgg cggtagtgcg    1740
tggagccatc cgcagttcga aaaaggcggt ggctctggtg gcggttctgg cggtagtgcc    1800
tggagccacc cgcagtttga aaataataa                                      1830

<210> SEQ ID NO 9
<211> LENGTH: 608
<212> TYPE: PRT
<213> ORGANISM: Bacillus subtilis phage phi29

<400> SEQUENCE: 9

Met Lys His Met Pro Arg Lys Met Tyr Ser Cys Ala Phe Glu Thr Thr
1               5                   10                  15

Thr Lys Val Glu Asp Cys Arg Val Trp Ala Tyr Gly Tyr Met Asn Ile
            20                  25                  30

Glu Asp His Ser Glu Tyr Lys Ile Gly Asn Ser Leu Asp Glu Phe Met
        35                  40                  45

Ala Trp Val Leu Lys Val Gln Ala Asp Leu Tyr Phe His Asn Leu Lys
    50                  55                  60

Phe Asp Gly Ala Phe Ile Ile Asn Trp Leu Glu Arg Asn Gly Phe Lys
65                  70                  75                  80

Trp Ser Ala Asp Gly Leu Pro Asn Thr Tyr Asn Thr Ile Ile Ser Arg
                85                  90                  95

Met Gly Gln Trp Tyr Met Ile Asp Ile Cys Leu Gly Tyr Lys Gly Lys
            100                 105                 110

Arg Lys Ile His Thr Val Ile Tyr Asp Ser Leu Lys Lys Leu Pro Phe
        115                 120                 125

Pro Val Lys Lys Ile Ala Lys Asp Phe Lys Leu Thr Val Leu Lys Gly
    130                 135                 140

Asp Ile Asp Tyr His Lys Glu Arg Pro Val Gly Tyr Lys Ile Thr Pro
145                 150                 155                 160

Glu Glu Tyr Ala Tyr Ile Lys Asn Asp Ile Gln Ile Ala Glu Ala
                165                 170                 175

Leu Leu Ile Gln Phe Lys Gln Gly Leu Asp Arg Met Thr Ala Gly Ser
            180                 185                 190

Asp Ser Leu Lys Gly Phe Lys Asp Ile Ile Thr Thr Lys Lys Phe Lys
        195                 200                 205

Lys Val Phe Pro Thr Leu Ser Leu Gly Leu Asp Lys Glu Val Arg Tyr
    210                 215                 220
```

```
Ala Tyr Arg Gly Gly Phe Thr Trp Leu Asn Asp Arg Phe Lys Glu Lys
225                 230                 235                 240

Glu Ile Gly Glu Gly Met Val Phe Asp Val Asn Ser Leu Tyr Pro Ala
            245                 250                 255

Gln Met Tyr Ser Arg Leu Leu Pro Tyr Gly Glu Pro Ile Val Phe Glu
        260                 265                 270

Gly Lys Tyr Val Trp Asp Glu Asp Tyr Pro Leu His Ile Gln His Ile
    275                 280                 285

Arg Cys Glu Phe Glu Leu Lys Glu Gly Tyr Ile Pro Thr Ile Gln Ile
290                 295                 300

Lys Arg Ser Arg Phe Tyr Lys Gly Asn Glu Tyr Leu Lys Ser Ser Gly
305                 310                 315                 320

Gly Glu Ile Ala Asp Leu Trp Leu Ser Asn Val Asp Leu Glu Leu Met
            325                 330                 335

Lys Glu His Tyr Asp Leu Tyr Asn Val Glu Tyr Ile Ser Gly Leu Lys
        340                 345                 350

Phe Lys Ala Thr Thr Gly Leu Phe Lys Asp Phe Ile Asp Lys Trp Thr
    355                 360                 365

Tyr Ile Lys Thr Thr Ser Glu Gly Ala Ile Lys Gln Leu Ala Lys Leu
370                 375                 380

Met Leu Asn Ser Leu Tyr Gly Lys Phe Ala Ser Asn Pro Asp Val Thr
385                 390                 395                 400

Gly Lys Val Pro Tyr Leu Lys Glu Asn Gly Ala Leu Gly Phe Arg Leu
            405                 410                 415

Gly Glu Glu Glu Thr Lys Asp Pro Val Tyr Thr Pro Met Gly Val Phe
        420                 425                 430

Ile Thr Ala Trp Ala Arg Tyr Thr Thr Ile Thr Ala Ala Gln Ala Cys
    435                 440                 445

Tyr Asp Arg Ile Ile Tyr Cys Asp Thr Asp Ser Ile His Leu Thr Gly
450                 455                 460

Thr Glu Ile Pro Asp Val Ile Lys Asp Ile Val Asp Pro Lys Lys Leu
465                 470                 475                 480

Gly Tyr Trp Ala His Glu Ser Thr Phe Lys Arg Ala Lys Tyr Leu Arg
            485                 490                 495

Gln Lys Thr Tyr Ile Gln Asp Ile Tyr Met Lys Glu Val Asp Gly Lys
        500                 505                 510

Leu Val Glu Gly Ser Pro Asp Asp Tyr Thr Asp Ile Lys Phe Ser Val
    515                 520                 525

Lys Cys Ala Gly Met Thr Asp Lys Ile Lys Lys Glu Val Thr Phe Glu
530                 535                 540

Asn Phe Lys Val Gly Phe Ser Arg Lys Met Lys Pro Lys Pro Val Gln
545                 550                 555                 560

Val Pro Gly Gly Val Val Leu Val Asp Asp Thr Phe Thr Ile Lys Ser
            565                 570                 575

Gly Gly Ser Ala Trp Ser His Pro Gln Phe Glu Lys Gly Gly Gly Ser
        580                 585                 590

Gly Gly Gly Ser Gly Gly Ser Ala Trp Ser His Pro Gln Phe Glu Lys
    595                 600                 605
```

<210> SEQ ID NO 10
<211> LENGTH: 1390
<212> TYPE: DNA
<213> ORGANISM: Escherichia coli

<400> SEQUENCE: 10

```
atgatgaacg atggcaaaca gcagagcacc ttcctgtttc atgattatga aaccttcggt      60
acccatccgg ccctggatcg tccggcgcag tttgcggcca ttcgcaccga tagcgaattc     120
aatgtgattg gcgaaccgga agtgttttat tgcaaaccgg ccgatgatta tctgccgcag     180
ccgggtgcgg tgctgattac cggtattacc ccgcaggaag cgcgcgcgaa aggtgaaaac     240
gaagcggcgt ttgccgcgcg cattcatagc ctgtttaccg tgccgaaaac ctgcattctg     300
ggctataaca atgtgcgctt cgatgatgaa gttacccgta atatctttta tcgtaacttt     360
tatgatccgt atgcgtggag ctggcagcat gataacagcc gttgggatct gctggatgtg     420
atgcgcgcgt gctatgcgct cgcccggaa ggcattaatt ggccggaaaa cgatgatggc     480
ctgccgagct ttcgtctgga acatctgacc aaagccaacg gcattgaaca tagcaatgcc     540
catgatgcga tggccgatgt ttatgcgacc attgcgatgg cgaaactggt taaaacccgt     600
cagccgcgcc tgtttgatta tctgtttacc caccgtaaca acacaaaact gatggcgctg     660
attgatgttc cgcagatgaa accgctggtg catgtgagcg gcatgtttgg cgcctggcgc     720
ggcaacacca gctgggtggc cccgctggcc tggcacccgg aaaatcgtaa cgccgtgatt     780
atggttgatc tggccggtga tattagcccg ctgctggaac tggatagcga tacccctgcgt     840
gaacgcctgt ataccgccaa aaccgatctg gcgataatg ccgccgtgcc ggtgaaactg     900
gttcacatta caaatgccc ggtgctggcc caggcgaaca ccctgcgccc ggaagatgcg     960
gatcgtctgg gtattaatcg ccagcattgt ctggataatc tgaaaatcct gcgtgaaaac    1020
ccgcaggtgc gtgaaaaagt ggtggcgatc ttcgcggaag cggaaccgtt caccccgagc    1080
gataacgtgg atgcgcagct gtataacggc ttctttagcg atgccgatcg cgcggcgatg    1140
aaaatcgttc tggaaaccga accgcgcaat ctgccggcgc tggatattac ctttgttgat    1200
aaacgtattg aaaaactgct gtttaattat cgtgcgcgca ttttccggg tacccctggat    1260
tatgccgaac agcagcgttg gctggaacat cgtcgtcagg ttttcacccc ggaatttctg    1320
cagggttatg cggatgaact gcagatgctg gttcagcagt atgccgatga taagaaaaaa    1380
gtggcgctgc                                                            1390
```

<210> SEQ ID NO 11
<211> LENGTH: 485
<212> TYPE: PRT
<213> ORGANISM: Escherichia coli

<400> SEQUENCE: 11

```
Met Met Asn Asp Gly Lys Gln Gln Ser Thr Phe Leu Phe His Asp Tyr
1               5                   10                  15

Glu Thr Phe Gly Thr His Pro Ala Leu Asp Arg Pro Ala Gln Phe Ala
            20                  25                  30

Ala Ile Arg Thr Asp Ser Glu Phe Asn Val Ile Gly Glu Pro Glu Val
        35                  40                  45

Phe Tyr Cys Lys Pro Ala Asp Asp Tyr Leu Pro Gln Pro Gly Ala Val
    50                  55                  60

Leu Ile Thr Gly Ile Thr Pro Gln Glu Ala Arg Ala Lys Gly Glu Asn
65                  70                  75                  80

Glu Ala Ala Phe Ala Ala Arg Ile His Ser Leu Phe Thr Val Pro Lys
                85                  90                  95

Thr Cys Ile Leu Gly Tyr Asn Asn Val Arg Phe Asp Asp Glu Val Thr
            100                 105                 110

Arg Asn Ile Phe Tyr Arg Asn Phe Tyr Asp Pro Tyr Ala Trp Ser Trp
```

```
            115                 120                 125
Gln His Asp Asn Ser Arg Trp Asp Leu Leu Asp Val Met Arg Ala Cys
            130                 135                 140
Tyr Ala Leu Arg Pro Glu Gly Ile Asn Trp Pro Glu Asn Asp Asp Gly
145                 150                 155                 160
Leu Pro Ser Phe Arg Leu Glu His Leu Thr Lys Ala Asn Gly Ile Glu
                165                 170                 175
His Ser Asn Ala His Asp Ala Met Ala Asp Val Tyr Ala Thr Ile Ala
            180                 185                 190
Met Ala Lys Leu Val Lys Thr Arg Gln Pro Arg Leu Phe Asp Tyr Leu
            195                 200                 205
Phe Thr His Arg Asn Lys His Lys Leu Met Ala Leu Ile Asp Val Pro
210                 215                 220
Gln Met Lys Pro Leu Val His Val Ser Gly Met Phe Gly Ala Trp Arg
225                 230                 235                 240
Gly Asn Thr Ser Trp Val Ala Pro Leu Ala Trp His Pro Glu Asn Arg
                245                 250                 255
Asn Ala Val Ile Met Val Asp Leu Ala Gly Asp Ile Ser Pro Leu Leu
            260                 265                 270
Glu Leu Asp Ser Asp Thr Leu Arg Glu Arg Leu Tyr Thr Ala Lys Thr
            275                 280                 285
Asp Leu Gly Asp Asn Ala Ala Val Pro Val Lys Leu Val His Ile Asn
            290                 295                 300
Lys Cys Pro Val Leu Ala Gln Ala Asn Thr Leu Arg Pro Glu Asp Ala
305                 310                 315                 320
Asp Arg Leu Gly Ile Asn Arg Gln His Cys Leu Asp Asn Leu Lys Ile
                325                 330                 335
Leu Arg Glu Asn Pro Gln Val Arg Glu Lys Val Val Ala Ile Phe Ala
            340                 345                 350
Glu Ala Glu Pro Phe Thr Pro Ser Asp Asn Val Asp Ala Gln Leu Tyr
            355                 360                 365
Asn Gly Phe Phe Ser Asp Ala Asp Arg Ala Ala Met Lys Ile Val Leu
370                 375                 380
Glu Thr Glu Pro Arg Asn Leu Pro Ala Leu Asp Ile Thr Phe Val Asp
385                 390                 395                 400
Lys Arg Ile Glu Lys Leu Leu Phe Asn Tyr Arg Ala Arg Asn Phe Pro
                405                 410                 415
Gly Thr Leu Asp Tyr Ala Glu Gln Gln Arg Trp Leu Glu His Arg Arg
            420                 425                 430
Gln Val Phe Thr Pro Glu Phe Leu Gln Gly Tyr Ala Asp Glu Leu Gln
            435                 440                 445
Met Leu Val Gln Gln Tyr Ala Asp Asp Lys Glu Lys Val Ala Leu Leu
            450                 455                 460
Lys Ala Leu Trp Gln Tyr Ala Glu Glu Ile Val Ser Gly Ser Gly His
465                 470                 475                 480
His His His His His
                485

<210> SEQ ID NO 12
<211> LENGTH: 804
<212> TYPE: DNA
<213> ORGANISM: Escherichia coli

<400> SEQUENCE: 12
```

```
atgaaatttg tctcttttaa tatcaacggc ctgcgcgcca gacctcacca gcttgaagcc    60
atcgtcgaaa agcaccaacc ggatgtgatt ggcctgcagg agacaaaagt tcatgacgat   120
atgtttccgc tcgaagaggt ggcgaagctc ggctacaacg tgttttatca cgggcagaaa   180
ggccattatg gcgtggcgct gctgaccaaa gagacgccga ttgccgtgcg tcgcggcttt   240
cccggtgacg acgaagaggc gcagcggcgg attattatgg cggaaatccc ctcactgctg   300
ggtaatgtca ccgtgatcaa cggttacttc ccgcagggtg aaagccgcga ccatccgata   360
aaattcccgg caaaagcgca gttttatcag aatctgcaaa actacctgga aaccgaactc   420
aaacgtgata tccggtact gattatgggc gatatgaata tcagccctac agatctggat   480
atcggcattg gcgaagaaaa ccgtaagcgc tggctgcgta ccggtaaatg ctcttttcctg   540
ccggaagagc gcgaatggat ggacaggctg atgagctggg ggttggtcga taccttccgc   600
catgcgaatc cgcaaacagc agatcgtttc tcatggtttg attaccgctc aaaaggtttt   660
gacgataacc gtggtctgcg catcgacctg ctgctcgcca gccaaccgct ggcagaatgt   720
tgcgtagaaa ccggcatcga ctatgaaatc cgcagcatgg aaaaaccgtc cgatcacgcc   780
cccgtctggg cgaccttccg ccgc                                          804
```

<210> SEQ ID NO 13
<211> LENGTH: 268
<212> TYPE: PRT
<213> ORGANISM: Escherichia coli

<400> SEQUENCE: 13

```
Met Lys Phe Val Ser Phe Asn Ile Asn Gly Leu Arg Ala Arg Pro His
1               5                   10                  15

Gln Leu Glu Ala Ile Val Glu Lys His Gln Pro Asp Val Ile Gly Leu
            20                  25                  30

Gln Glu Thr Lys Val His Asp Asp Met Phe Pro Leu Glu Glu Val Ala
        35                  40                  45

Lys Leu Gly Tyr Asn Val Phe Tyr His Gly Gln Lys Gly His Tyr Gly
    50                  55                  60

Val Ala Leu Leu Thr Lys Glu Thr Pro Ile Ala Val Arg Arg Gly Phe
65                  70                  75                  80

Pro Gly Asp Asp Glu Glu Ala Gln Arg Arg Ile Ile Met Ala Glu Ile
                85                  90                  95

Pro Ser Leu Leu Gly Asn Val Thr Val Ile Asn Gly Tyr Phe Pro Gln
            100                 105                 110

Gly Glu Ser Arg Asp His Pro Ile Lys Phe Pro Ala Lys Ala Gln Phe
        115                 120                 125

Tyr Gln Asn Leu Gln Asn Tyr Leu Glu Thr Glu Leu Lys Arg Asp Asn
    130                 135                 140

Pro Val Leu Ile Met Gly Asp Met Asn Ile Ser Pro Thr Asp Leu Asp
145                 150                 155                 160

Ile Gly Ile Gly Glu Glu Asn Arg Lys Arg Trp Leu Arg Thr Gly Lys
                165                 170                 175

Cys Ser Phe Leu Pro Glu Glu Arg Glu Trp Met Asp Arg Leu Met Ser
            180                 185                 190

Trp Gly Leu Val Asp Thr Phe Arg His Ala Asn Pro Gln Thr Ala Asp
        195                 200                 205

Arg Phe Ser Trp Phe Asp Tyr Arg Ser Lys Gly Phe Asp Asp Asn Arg
    210                 215                 220

Gly Leu Arg Ile Asp Leu Leu Leu Ala Ser Gln Pro Leu Ala Glu Cys
```

```
                225                 230                 235                 240
            Cys Val Glu Thr Gly Ile Asp Tyr Glu Ile Arg Ser Met Glu Lys Pro
                            245                 250                 255

Ser Asp His Ala Pro Val Trp Ala Thr Phe Arg Arg
                        260                 265

<210> SEQ ID NO 14
<211> LENGTH: 1275
<212> TYPE: DNA
<213> ORGANISM: Thermus thermophilus

<400> SEQUENCE: 14
atgtttcgtc gtaaagaaga tctggatccg ccgctggcac tgctgccgct gaaaggcctg      60
cgcgaagccg ccgcactgct ggaagaagcg ctgcgtcaag gtaaacgcat tcgtgttcac     120
ggcgactatg atgcggatgg cctgaccggc accgcgatcc tggttcgtgg tctggccgcc     180
ctgggtgcgg atgttcatcc gtttatcccg caccgcctgg aagaaggcta tggtgtcctg     240
atggaacgcg tcccggaaca tctggaagcc tcggacctgt ttctgaccgt tgactgcggc     300
attaccaacc atgcggaact gcgcgaactg ctggaaaatg cgtggaagt cattgttacc      360 gatcatcata cgccgggcaa aacgccgccg ccgggtctgg tcgtgcatcc ggcgctgacg     420
ccggatctga agaaaaaacc gaccggcgca ggcgtggcgt ttctgctgct gtgggcactg     480
catgaacgcc tgggcctgcc gccgccgctg gaatacgcgg acctggcagc cgttggcacc     540
attgccgacg ttgccccgct gtggggttgg aatcgtgcac tggtgaaaga aggtctggca     600
cgcatcccgg cttcatcttg ggtgggcctg cgtctgctgg ctgaagccgt gggctatacc     660
ggcaaagcgg tcgaagtcgc tttccgcatc gcgccgcgca tcaatgcggc ttcccgcctg     720
ggcgaagcgg aaaaagccct gcgcctgctg ctgacggatg atgcggcaga agctcaggcg     780
ctggtcggcg aactgcaccg tctgaacgcc gtcgtcaga ccctggaaga agcgatgctg      840
cgcaaactgc tgccgcaggc cgacccggaa gcgaaagcca tcgttctgct ggacccggaa     900
ggccatccgg tgttatggg tattgtggcc tctcgcatcc tggaagcgac cctgcgcccg      960
gtctttctgg tgcccaggg caaaggcacc gtgcgttcgc tggctccgat tccgccgtc      1020 gaagcactgc gcagcgcgga agatctgctg ctgcgttatg gtggtcataa agaagcggcg    1080
ggtttcgcaa tggatgaagc gctgtttccg gcgttcaaag cacgcgttga agcgtatgcc    1140
gcacgtttcc cggatccggt tcgtgaagtg gcactgctgg atctgctgcc ggaaccgggc    1200
ctgctgccgc aggtgttccg tgaactggca ctgctggaac gtatggtga aggtaacccg     1260 gaaccgctgt tcctg                                                     1275

<210> SEQ ID NO 15
<211> LENGTH: 425
<212> TYPE: PRT
<213> ORGANISM: Thermus thermophilus

<400> SEQUENCE: 15

Met Phe Arg Arg Lys Glu Asp Leu Asp Pro Pro Leu Ala Leu Leu Pro
1               5                   10                  15

Leu Lys Gly Leu Arg Glu Ala Ala Ala Leu Leu Glu Glu Ala Leu Arg
            20                  25                  30

Gln Gly Lys Arg Ile Arg Val His Gly Asp Tyr Asp Ala Asp Gly Leu
        35                  40                  45

Thr Gly Thr Ala Ile Leu Val Arg Gly Leu Ala Ala Leu Gly Ala Asp
    50                  55                  60
```

Val His Pro Phe Ile Pro His Arg Leu Glu Glu Gly Tyr Gly Val Leu
 65                  70                  75                  80

Met Glu Arg Val Pro Glu His Leu Glu Ala Ser Asp Leu Phe Leu Thr
             85                  90                  95

Val Asp Cys Gly Ile Thr Asn His Ala Glu Leu Arg Glu Leu Leu Glu
            100                 105                 110

Asn Gly Val Glu Val Ile Val Thr Asp His His Thr Pro Gly Lys Thr
        115                 120                 125

Pro Pro Pro Gly Leu Val Val His Pro Ala Leu Thr Pro Asp Leu Lys
130                 135                 140

Glu Lys Pro Thr Gly Ala Gly Val Ala Phe Leu Leu Trp Ala Leu
145                 150                 155                 160

His Glu Arg Leu Gly Leu Pro Pro Leu Glu Tyr Ala Asp Leu Ala
                165                 170                 175

Ala Val Gly Thr Ile Ala Asp Val Ala Pro Leu Trp Gly Trp Asn Arg
            180                 185                 190

Ala Leu Val Lys Glu Gly Leu Ala Arg Ile Pro Ala Ser Ser Trp Val
        195                 200                 205

Gly Leu Arg Leu Leu Ala Glu Ala Val Gly Tyr Thr Gly Lys Ala Val
210                 215                 220

Glu Val Ala Phe Arg Ile Ala Pro Arg Ile Asn Ala Ala Ser Arg Leu
225                 230                 235                 240

Gly Glu Ala Glu Lys Ala Leu Arg Leu Leu Thr Asp Asp Ala Ala
                245                 250                 255

Glu Ala Gln Ala Leu Val Gly Glu Leu His Arg Leu Asn Ala Arg Arg
            260                 265                 270

Gln Thr Leu Glu Glu Ala Met Leu Arg Lys Leu Leu Pro Gln Ala Asp
        275                 280                 285

Pro Glu Ala Lys Ala Ile Val Leu Leu Asp Pro Glu Gly His Pro Gly
    290                 295                 300

Val Met Gly Ile Val Ala Ser Arg Ile Leu Glu Ala Thr Leu Arg Pro
305                 310                 315                 320

Val Phe Leu Val Ala Gln Gly Lys Gly Thr Val Arg Ser Leu Ala Pro
                325                 330                 335

Ile Ser Ala Val Glu Ala Leu Arg Ser Ala Glu Asp Leu Leu Leu Arg
            340                 345                 350

Tyr Gly Gly His Lys Glu Ala Ala Gly Phe Ala Met Asp Glu Ala Leu
        355                 360                 365

Phe Pro Ala Phe Lys Ala Arg Val Glu Ala Tyr Ala Ala Arg Phe Pro
    370                 375                 380

Asp Pro Val Arg Glu Val Ala Leu Leu Asp Leu Leu Pro Glu Pro Gly
385                 390                 395                 400

Leu Leu Pro Gln Val Phe Arg Glu Leu Ala Leu Leu Glu Pro Tyr Gly
                405                 410                 415

Glu Gly Asn Pro Glu Pro Leu Phe Leu
            420                 425

<210> SEQ ID NO 16
<211> LENGTH: 738
<212> TYPE: DNA
<213> ORGANISM: Bacteriophage lambda

<400> SEQUENCE: 16
tccggaagcg gctctggtag tggttctggc atgacaccgg acattatcct gcagcgtacc    60

```
gggatcgatg tgagagctgt cgaacagggg gatgatgcgt ggcacaaatt acggctcggc    120
gtcatcaccg cttcagaagt tcacaacgtg atagcaaaac cccgctccgg aaagaagtgg    180
cctgacatga aaatgtccta cttccacacc ctgcttgctg aggtttgcac cggtgtggct    240
ccggaagtta acgctaaagc actggcctgg gaaaacagt acgagaacga cgccagaacc    300
ctgtttgaat tcacttccgg cgtgaatgtt actgaatccc cgatcatcta tcgcgacgaa    360
agtatgcgta ccgcctgctc tcccgatggt ttatgcagtg acgcaacgg ccttgaactg    420
aaatgcccgt ttacctcccg ggatttcatg aagttccggc tcggtggttt cgaggccata    480
aagtcagctt acatggccca ggtgcagtac agcatgtggg tgacgcgaaa aaatgcctgg    540
tactttgcca actatgaccc gcgtatgaag cgtgaaggcc tgcattatgt cgtgattgag    600
cgggatgaaa agtacatggc gagttttgac gagatcgtgc cggagttcat cgaaaaaatg    660
gacgaggcac tggctgaaat tggttttgta tttggggagc aatggcgatc tggctctggt    720
tccggcagcg gttccgga                                                  738
```

<210> SEQ ID NO 17
<211> LENGTH: 226
<212> TYPE: PRT
<213> ORGANISM: Bacteriophage lambda
<400> SEQUENCE: 17

```
Met Thr Pro Asp Ile Ile Leu Gln Arg Thr Gly Ile Asp Val Arg Ala
1               5                   10                  15

Val Glu Gln Gly Asp Asp Ala Trp His Lys Leu Arg Leu Gly Val Ile
            20                  25                  30

Thr Ala Ser Glu Val His Asn Val Ile Ala Lys Pro Arg Ser Gly Lys
        35                  40                  45

Lys Trp Pro Asp Met Lys Met Ser Tyr Phe His Thr Leu Leu Ala Glu
    50                  55                  60

Val Cys Thr Gly Val Ala Pro Glu Val Asn Ala Lys Ala Leu Ala Trp
65                  70                  75                  80

Gly Lys Gln Tyr Glu Asn Asp Ala Arg Thr Leu Phe Glu Phe Thr Ser
                85                  90                  95

Gly Val Asn Val Thr Glu Ser Pro Ile Ile Tyr Arg Asp Glu Ser Met
            100                 105                 110

Arg Thr Ala Cys Ser Pro Asp Gly Leu Cys Ser Asp Gly Asn Gly Leu
        115                 120                 125

Glu Leu Lys Cys Pro Phe Thr Ser Arg Asp Phe Met Lys Phe Arg Leu
    130                 135                 140

Gly Gly Phe Glu Ala Ile Lys Ser Ala Tyr Met Ala Gln Val Gln Tyr
145                 150                 155                 160

Ser Met Trp Val Thr Arg Lys Asn Ala Trp Tyr Phe Ala Asn Tyr Asp
                165                 170                 175

Pro Arg Met Lys Arg Glu Gly Leu His Tyr Val Val Ile Glu Arg Asp
            180                 185                 190

Glu Lys Tyr Met Ala Ser Phe Asp Glu Ile Val Pro Glu Phe Ile Glu
        195                 200                 205

Lys Met Asp Glu Ala Leu Ala Glu Ile Gly Phe Val Phe Gly Glu Gln
    210                 215                 220

Trp Arg
225
```

<210> SEQ ID NO 18
<211> LENGTH: 760
<212> TYPE: PRT
<213> ORGANISM: Methanococcoides burtonii

<400> SEQUENCE: 18

```
Met Met Ile Arg Glu Leu Asp Ile Pro Arg Asp Ile Ile Gly Phe Tyr
1               5                   10                  15

Glu Asp Ser Gly Ile Lys Glu Leu Tyr Pro Pro Gln Ala Glu Ala Ile
            20                  25                  30

Glu Met Gly Leu Leu Glu Lys Lys Asn Leu Leu Ala Ala Ile Pro Thr
        35                  40                  45

Ala Ser Gly Lys Thr Leu Leu Ala Glu Leu Ala Met Ile Lys Ala Ile
    50                  55                  60

Arg Glu Gly Gly Lys Ala Leu Tyr Ile Val Pro Leu Arg Ala Leu Ala
65                  70                  75                  80

Ser Glu Lys Phe Glu Arg Phe Lys Glu Leu Ala Pro Phe Gly Ile Lys
                85                  90                  95

Val Gly Ile Ser Thr Gly Asp Leu Asp Ser Arg Ala Asp Trp Leu Gly
            100                 105                 110

Val Asn Asp Ile Ile Val Ala Thr Ser Glu Lys Thr Asp Ser Leu Leu
        115                 120                 125

Arg Asn Gly Thr Ser Trp Met Asp Glu Ile Thr Thr Val Val Val Asp
    130                 135                 140

Glu Ile His Leu Leu Asp Ser Lys Asn Arg Gly Pro Thr Leu Glu Val
145                 150                 155                 160

Thr Ile Thr Lys Leu Met Arg Leu Asn Pro Asp Val Gln Val Val Ala
                165                 170                 175

Leu Ser Ala Thr Val Gly Asn Ala Arg Glu Met Ala Asp Trp Leu Gly
            180                 185                 190

Ala Ala Leu Val Leu Ser Glu Trp Arg Pro Thr Asp Leu His Glu Gly
        195                 200                 205

Val Leu Phe Gly Asp Ala Ile Asn Phe Pro Gly Ser Gln Lys Lys Ile
    210                 215                 220

Asp Arg Leu Glu Lys Asp Asp Ala Val Asn Leu Val Leu Asp Thr Ile
225                 230                 235                 240

Lys Ala Glu Gly Gln Cys Leu Val Phe Glu Ser Ser Arg Arg Asn Cys
                245                 250                 255

Ala Gly Phe Ala Lys Thr Ala Ser Ser Lys Val Ala Lys Ile Leu Asp
            260                 265                 270

Asn Asp Ile Met Ile Lys Leu Ala Gly Ile Ala Glu Glu Val Glu Ser
        275                 280                 285

Thr Gly Glu Thr Asp Thr Ala Ile Val Leu Ala Asn Cys Ile Arg Lys
    290                 295                 300

Gly Val Ala Phe His His Ala Gly Leu Asn Ser Asn His Arg Lys Leu
305                 310                 315                 320

Val Glu Asn Gly Phe Arg Gln Asn Leu Ile Lys Val Ile Ser Ser Thr
                325                 330                 335

Pro Thr Leu Ala Ala Gly Leu Asn Leu Pro Ala Arg Arg Val Ile Ile
            340                 345                 350

Arg Ser Tyr Arg Arg Phe Asp Ser Asn Phe Gly Met Gln Pro Ile Pro
        355                 360                 365

Val Leu Glu Tyr Lys Gln Met Ala Gly Arg Ala Gly Arg Pro His Leu
    370                 375                 380
```

Asp Pro Tyr Gly Glu Ser Val Leu Leu Ala Lys Thr Tyr Asp Glu Phe
385                 390                 395                 400

Ala Gln Leu Met Glu Asn Tyr Val Glu Ala Asp Ala Glu Asp Ile Trp
            405                 410                 415

Ser Lys Leu Gly Thr Glu Asn Ala Leu Arg Thr His Val Leu Ser Thr
            420                 425                 430

Ile Val Asn Gly Phe Ala Ser Thr Arg Gln Glu Leu Phe Asp Phe Phe
            435                 440                 445

Gly Ala Thr Phe Phe Ala Tyr Gln Gln Asp Lys Trp Met Leu Glu Glu
            450                 455                 460

Val Ile Asn Asp Cys Leu Glu Phe Leu Ile Asp Lys Ala Met Val Ser
465                 470                 475                 480

Glu Thr Glu Asp Ile Glu Asp Ala Ser Lys Leu Phe Leu Arg Gly Thr
                485                 490                 495

Arg Leu Gly Ser Leu Val Ser Met Leu Tyr Ile Asp Pro Leu Ser Gly
                500                 505                 510

Ser Lys Ile Val Asp Gly Phe Lys Asp Ile Gly Lys Ser Thr Gly Gly
            515                 520                 525

Asn Met Gly Ser Leu Glu Asp Asp Lys Gly Asp Asp Ile Thr Val Thr
            530                 535                 540

Asp Met Thr Leu Leu His Leu Val Cys Ser Thr Pro Asp Met Arg Gln
545                 550                 555                 560

Leu Tyr Leu Arg Asn Thr Asp Tyr Thr Ile Val Asn Glu Tyr Ile Val
                565                 570                 575

Ala His Ser Asp Glu Phe His Glu Ile Pro Asp Lys Leu Lys Glu Thr
            580                 585                 590

Asp Tyr Glu Trp Phe Met Gly Glu Val Lys Thr Ala Met Leu Leu Glu
            595                 600                 605

Glu Trp Val Thr Glu Val Ser Ala Glu Asp Ile Thr Arg His Phe Asn
610                 615                 620

Val Gly Glu Gly Asp Ile His Ala Leu Ala Asp Thr Ser Glu Trp Leu
625                 630                 635                 640

Met His Ala Ala Ala Lys Leu Ala Glu Leu Leu Gly Val Glu Tyr Ser
                645                 650                 655

Ser His Ala Tyr Ser Leu Glu Lys Arg Ile Arg Tyr Gly Ser Gly Leu
            660                 665                 670

Asp Leu Met Glu Leu Val Gly Ile Arg Gly Val Gly Arg Val Arg Ala
            675                 680                 685

Arg Lys Leu Tyr Asn Ala Gly Phe Val Ser Val Ala Lys Leu Lys Gly
            690                 695                 700

Ala Asp Ile Ser Val Leu Ser Lys Leu Val Gly Pro Lys Val Ala Tyr
705                 710                 715                 720

Asn Ile Leu Ser Gly Ile Gly Val Arg Val Asn Asp Lys His Phe Asn
                725                 730                 735

Ser Ala Pro Ile Ser Ser Asn Thr Leu Asp Thr Leu Leu Asp Lys Asn
            740                 745                 750

Gln Lys Thr Phe Asn Asp Phe Gln
            755                 760

<210> SEQ ID NO 19
<211> LENGTH: 707
<212> TYPE: PRT
<213> ORGANISM: Cenarchaeum symbiosum

<400> SEQUENCE: 19

-continued

```
Met Arg Ile Ser Glu Leu Asp Ile Pro Arg Pro Ala Ile Glu Phe Leu
 1               5                  10                  15

Glu Gly Glu Gly Tyr Lys Lys Leu Tyr Pro Pro Gln Ala Ala Ala Ala
                20                  25                  30

Lys Ala Gly Leu Thr Asp Gly Lys Ser Val Leu Val Ser Ala Pro Thr
                35                  40                  45

Ala Ser Gly Lys Thr Leu Ile Ala Ala Ile Ala Met Ile Ser His Leu
    50                  55                  60

Ser Arg Asn Arg Gly Lys Ala Val Tyr Leu Ser Pro Leu Arg Ala Leu
 65                  70                  75                  80

Ala Ala Glu Lys Phe Ala Glu Phe Gly Lys Ile Gly Ile Pro Leu
                85                  90                  95

Gly Arg Pro Val Arg Val Gly Val Ser Thr Gly Asp Phe Glu Lys Ala
                100                 105                 110

Gly Arg Ser Leu Gly Asn Asn Asp Ile Leu Val Leu Thr Asn Glu Arg
                115                 120                 125

Met Asp Ser Leu Ile Arg Arg Arg Pro Asp Trp Met Asp Glu Val Gly
                130                 135                 140

Leu Val Ile Ala Asp Glu Ile His Leu Ile Gly Asp Arg Ser Arg Gly
145                 150                 155                 160

Pro Thr Leu Glu Met Val Leu Thr Lys Leu Arg Gly Leu Arg Ser Ser
                165                 170                 175

Pro Gln Val Val Ala Leu Ser Ala Thr Ile Ser Asn Ala Asp Glu Ile
                180                 185                 190

Ala Gly Trp Leu Asp Cys Thr Leu Val His Ser Thr Trp Arg Pro Val
                195                 200                 205

Pro Leu Ser Glu Gly Val Tyr Gln Asp Gly Glu Val Ala Met Gly Asp
                210                 215                 220

Gly Ser Arg His Glu Val Ala Ala Thr Gly Gly Pro Ala Val Asp
225                 230                 235                 240

Leu Ala Ala Glu Ser Val Ala Glu Gly Gly Gln Ser Leu Ile Phe Ala
                245                 250                 255

Asp Thr Arg Ala Arg Ser Ala Ser Leu Ala Ala Lys Ala Ser Ala Val
                260                 265                 270

Ile Pro Glu Ala Lys Gly Ala Asp Ala Ala Lys Leu Ala Ala Ala Ala
                275                 280                 285

Lys Lys Ile Ile Ser Ser Gly Glu Thr Lys Leu Ala Lys Thr Leu
                290                 295                 300

Ala Glu Leu Val Glu Lys Gly Ala Ala Phe His His Ala Gly Leu Asn
305                 310                 315                 320

Gln Asp Cys Arg Ser Val Val Glu Glu Phe Arg Ser Gly Arg Ile
                325                 330                 335

Arg Leu Leu Ala Ser Thr Pro Thr Leu Ala Ala Gly Val Asn Leu Pro
                340                 345                 350

Ala Arg Arg Val Val Ile Ser Ser Val Met Arg Tyr Asn Ser Ser Ser
                355                 360                 365

Gly Met Ser Glu Pro Ile Ser Ile Leu Glu Tyr Lys Gln Leu Cys Gly
                370                 375                 380

Arg Ala Gly Arg Pro Gln Tyr Asp Lys Ser Gly Glu Ala Ile Val Val
385                 390                 395                 400

Gly Gly Val Asn Ala Asp Glu Ile Phe Asp Arg Tyr Ile Gly Gly Glu
                405                 410                 415
```

-continued

```
Pro Glu Pro Ile Arg Ser Ala Met Val Asp Asp Arg Ala Leu Arg Ile
            420                 425                 430

His Val Leu Ser Leu Val Thr Thr Ser Pro Gly Ile Lys Glu Asp Asp
        435                 440                 445

Val Thr Glu Phe Phe Leu Gly Thr Leu Gly Gly Gln Gln Ser Gly Glu
    450                 455                 460

Ser Thr Val Lys Phe Ser Val Ala Val Ala Leu Arg Phe Leu Gln Glu
465                 470                 475                 480

Glu Gly Met Leu Gly Arg Arg Gly Gly Arg Leu Ala Ala Thr Lys Met
                485                 490                 495

Gly Arg Leu Val Ser Arg Leu Tyr Met Asp Pro Met Thr Ala Val Thr
            500                 505                 510

Leu Arg Asp Ala Val Gly Glu Ala Ser Pro Gly Arg Met His Thr Leu
        515                 520                 525

Gly Phe Leu His Leu Val Ser Glu Cys Ser Glu Phe Met Pro Arg Phe
    530                 535                 540

Ala Leu Arg Gln Lys Asp His Glu Val Ala Glu Met Met Leu Glu Ala
545                 550                 555                 560

Gly Arg Gly Glu Leu Leu Arg Pro Val Tyr Ser Tyr Glu Cys Gly Arg
                565                 570                 575

Gly Leu Leu Ala Leu His Arg Trp Ile Gly Glu Ser Pro Glu Ala Lys
            580                 585                 590

Leu Ala Glu Asp Leu Lys Phe Glu Ser Gly Asp Val His Arg Met Val
        595                 600                 605

Glu Ser Ser Gly Trp Leu Leu Arg Cys Ile Trp Glu Ile Ser Lys His
    610                 615                 620

Gln Glu Arg Pro Asp Leu Leu Gly Glu Leu Asp Val Leu Arg Ser Arg
625                 630                 635                 640

Val Ala Tyr Gly Ile Lys Ala Glu Leu Val Pro Leu Val Ser Ile Lys
                645                 650                 655

Gly Ile Gly Arg Val Arg Ser Arg Arg Leu Phe Arg Gly Gly Ile Lys
            660                 665                 670

Gly Pro Gly Asp Leu Ala Ala Val Pro Val Glu Arg Leu Ser Arg Val
        675                 680                 685

Glu Gly Ile Gly Ala Thr Leu Ala Asn Asn Ile Lys Ser Gln Leu Arg
    690                 695                 700

Lys Gly Gly
705

<210> SEQ ID NO 20
<211> LENGTH: 720
<212> TYPE: PRT
<213> ORGANISM: Thermococcus gammatolerans

<400> SEQUENCE: 20

Met Lys Val Asp Glu Leu Pro Val Asp Glu Arg Leu Lys Ala Val Leu
1               5                   10                  15

Lys Glu Arg Gly Ile Glu Glu Leu Tyr Pro Pro Gln Ala Glu Ala Leu
                20                  25                  30

Lys Ser Gly Ala Leu Glu Gly Arg Asn Leu Val Leu Ala Ile Pro Thr
            35                  40                  45

Ala Ser Gly Lys Thr Leu Val Ser Glu Ile Val Met Val Asn Lys Leu
        50                  55                  60

Ile Gln Glu Gly Gly Lys Ala Val Tyr Leu Val Pro Leu Lys Ala Leu
65                  70                  75                  80
```

```
Ala Glu Glu Lys Tyr Arg Glu Phe Lys Glu Trp Lys Leu Gly Leu
                85                  90                  95
Lys Val Ala Ala Thr Thr Gly Asp Tyr Asp Ser Thr Asp Asp Trp Leu
            100                 105                 110
Gly Arg Tyr Asp Ile Ile Val Ala Thr Ala Glu Lys Phe Asp Ser Leu
            115                 120                 125
Leu Arg His Gly Ala Arg Trp Ile Asn Asp Val Lys Leu Val Val Ala
        130                 135                 140
Asp Glu Val His Leu Ile Gly Ser Tyr Asp Arg Gly Ala Thr Leu Glu
145                 150                 155                 160
Met Ile Leu Thr His Met Leu Gly Arg Ala Gln Ile Leu Ala Leu Ser
                165                 170                 175
Ala Thr Val Gly Asn Ala Glu Glu Leu Ala Glu Trp Leu Asp Ala Ser
            180                 185                 190
Leu Val Val Ser Asp Trp Arg Pro Val Gln Leu Arg Arg Gly Val Phe
        195                 200                 205
His Leu Gly Thr Leu Ile Trp Glu Asp Gly Lys Val Glu Ser Tyr Pro
        210                 215                 220
Glu Asn Trp Tyr Ser Leu Val Val Asp Ala Val Lys Arg Gly Lys Gly
225                 230                 235                 240
Ala Leu Val Phe Val Asn Thr Arg Arg Ser Ala Glu Lys Glu Ala Leu
                245                 250                 255
Ala Leu Ser Lys Leu Val Ser Ser His Leu Thr Lys Pro Glu Lys Arg
            260                 265                 270
Ala Leu Glu Ser Leu Ala Ser Gln Leu Glu Asp Asn Pro Thr Ser Glu
        275                 280                 285
Lys Leu Lys Arg Ala Leu Arg Gly Gly Val Ala Phe His His Ala Gly
290                 295                 300
Leu Ser Arg Val Glu Arg Thr Leu Ile Glu Asp Ala Phe Arg Glu Gly
305                 310                 315                 320
Leu Ile Lys Val Ile Thr Ala Thr Pro Thr Leu Ser Ala Gly Val Asn
                325                 330                 335
Leu Pro Ser Phe Arg Val Ile Ile Arg Asp Thr Lys Arg Tyr Ala Gly
            340                 345                 350
Phe Gly Trp Thr Asp Ile Pro Val Leu Glu Ile Gln Gln Met Met Gly
        355                 360                 365
Arg Ala Gly Arg Pro Arg Tyr Asp Lys Tyr Gly Glu Ala Ile Ile Val
        370                 375                 380
Ala Arg Thr Asp Glu Pro Gly Lys Leu Met Glu Arg Tyr Ile Arg Gly
385                 390                 395                 400
Lys Pro Glu Lys Leu Phe Ser Met Leu Ala Asn Glu Gln Ala Phe Arg
                405                 410                 415
Ser Gln Val Leu Ala Leu Ile Thr Asn Phe Gly Ile Arg Ser Phe Pro
            420                 425                 430
Glu Leu Val Arg Phe Leu Glu Arg Thr Phe Tyr Ala His Gln Arg Lys
        435                 440                 445
Asp Leu Ser Ser Leu Glu Tyr Lys Ala Lys Glu Val Val Tyr Phe Leu
450                 455                 460
Ile Glu Asn Glu Phe Ile Asp Leu Asp Leu Glu Asp Arg Phe Ile Pro
465                 470                 475                 480
Leu Pro Phe Gly Lys Arg Thr Ser Gln Leu Tyr Ile Asp Pro Leu Thr
                485                 490                 495
```

Ala Lys Lys Phe Lys Asp Ala Phe Pro Ala Ile Glu Arg Asn Pro Asn
            500                 505                 510

Pro Phe Gly Ile Phe Gln Leu Ile Ala Ser Thr Pro Asp Met Ala Thr
        515                 520                 525

Leu Thr Ala Arg Arg Glu Met Glu Asp Tyr Leu Asp Leu Ala Tyr
    530                 535                 540

Glu Leu Glu Asp Lys Leu Tyr Ala Ser Ile Pro Tyr Tyr Glu Asp Ser
545                 550                 555                 560

Arg Phe Gln Gly Phe Leu Gly Gln Val Lys Thr Ala Lys Val Leu Leu
                565                 570                 575

Asp Trp Ile Asn Glu Val Pro Glu Ala Arg Ile Tyr Glu Thr Tyr Ser
            580                 585                 590

Ile Asp Pro Gly Asp Leu Tyr Arg Leu Leu Glu Leu Ala Asp Trp Leu
            595                 600                 605

Met Tyr Ser Leu Ile Glu Leu Tyr Lys Leu Phe Glu Pro Lys Glu Glu
            610                 615                 620

Ile Leu Asn Tyr Leu Arg Asp Leu His Leu Arg Leu His Gly Val
625                 630                 635                 640

Arg Glu Glu Leu Leu Glu Leu Val Arg Leu Pro Asn Ile Gly Arg Lys
                645                 650                 655

Arg Ala Arg Ala Leu Tyr Asn Ala Gly Phe Arg Ser Val Glu Ala Ile
            660                 665                 670

Ala Asn Ala Lys Pro Ala Glu Leu Leu Ala Val Glu Gly Ile Gly Ala
            675                 680                 685

Lys Ile Leu Asp Gly Ile Tyr Arg His Leu Gly Ile Glu Lys Arg Val
            690                 695                 700

Thr Glu Glu Lys Pro Lys Arg Lys Gly Thr Leu Glu Asp Phe Leu Arg
705                 710                 715                 720

<210> SEQ ID NO 21
<211> LENGTH: 799
<212> TYPE: PRT
<213> ORGANISM: Methanospirillum hungatei

<400> SEQUENCE: 21

Met Glu Ile Ala Ser Leu Pro Leu Pro Asp Ser Phe Ile Arg Ala Cys
1               5                   10                  15

His Ala Lys Gly Ile Arg Ser Leu Tyr Pro Pro Gln Ala Glu Cys Ile
            20                  25                  30

Glu Lys Gly Leu Leu Glu Gly Lys Asn Leu Leu Ile Ser Ile Pro Thr
        35                  40                  45

Ala Ser Gly Lys Thr Leu Leu Ala Glu Met Ala Met Trp Ser Arg Ile
    50                  55                  60

Ala Ala Gly Gly Lys Cys Leu Tyr Ile Val Pro Leu Arg Ala Leu Ala
65                  70                  75                  80

Ser Glu Lys Tyr Asp Glu Phe Ser Lys Lys Gly Val Ile Arg Val Gly
                85                  90                  95

Ile Ala Thr Gly Asp Leu Asp Arg Thr Asp Ala Tyr Leu Gly Glu Asn
            100                 105                 110

Asp Ile Ile Val Ala Thr Ser Glu Lys Thr Asp Ser Leu Leu Arg Asn
            115                 120                 125

Arg Thr Pro Trp Leu Ser Gln Ile Thr Cys Ile Val Leu Asp Glu Val
        130                 135                 140

His Leu Ile Gly Ser Glu Asn Arg Gly Ala Thr Leu Glu Met Val Ile
145                 150                 155                 160

-continued

```
Thr Lys Leu Arg Tyr Thr Asn Pro Val Met Gln Ile Ile Gly Leu Ser
            165                 170                 175

Ala Thr Ile Gly Asn Pro Ala Gln Leu Ala Glu Trp Leu Asp Ala Thr
            180                 185                 190

Leu Ile Thr Ser Thr Trp Arg Pro Val Asp Leu Arg Gln Gly Val Tyr
            195                 200                 205

Tyr Asn Gly Lys Ile Arg Phe Ser Asp Ser Glu Arg Pro Ile Gln Gly
        210                 215                 220

Lys Thr Lys His Asp Asp Leu Asn Leu Cys Leu Asp Thr Ile Glu Glu
225                 230                 235                 240

Gly Gly Gln Cys Leu Val Phe Val Ser Arg Arg Asn Ala Glu Gly
            245                 250                 255

Phe Ala Lys Lys Ala Ala Gly Ala Leu Lys Ala Gly Ser Pro Asp Ser
            260                 265                 270

Lys Ala Leu Ala Gln Glu Leu Arg Arg Leu Arg Asp Arg Asp Glu Gly
            275                 280                 285

Asn Val Leu Ala Asp Cys Val Glu Arg Gly Ala Ala Phe His His Ala
            290                 295                 300

Gly Leu Ile Arg Gln Glu Arg Thr Ile Ile Glu Glu Gly Phe Arg Asn
305                 310                 315                 320

Gly Tyr Ile Glu Val Ile Ala Ala Thr Pro Thr Leu Ala Ala Gly Leu
            325                 330                 335

Asn Leu Pro Ala Arg Arg Val Ile Arg Asp Tyr Asn Arg Phe Ala
            340                 345                 350

Ser Gly Leu Gly Met Val Pro Ile Pro Val Gly Glu Tyr His Gln Met
            355                 360                 365

Ala Gly Arg Ala Gly Arg Pro His Leu Asp Pro Tyr Gly Glu Ala Val
            370                 375                 380

Leu Leu Ala Lys Asp Ala Pro Ser Val Glu Arg Leu Phe Glu Thr Phe
385                 390                 395                 400

Ile Asp Ala Glu Ala Glu Arg Val Asp Ser Gln Cys Val Asp Asp Ala
            405                 410                 415

Ser Leu Cys Ala His Ile Leu Ser Leu Ile Ala Thr Gly Phe Ala His
            420                 425                 430

Asp Gln Glu Ala Leu Ser Ser Phe Met Glu Arg Thr Phe Tyr Phe Phe
            435                 440                 445

Gln His Pro Lys Thr Arg Ser Leu Pro Arg Leu Val Ala Asp Ala Ile
            450                 455                 460

Arg Phe Leu Thr Thr Ala Gly Met Val Glu Glu Arg Glu Asn Thr Leu
465                 470                 475                 480

Ser Ala Thr Arg Leu Gly Ser Leu Val Ser Arg Leu Tyr Leu Asn Pro
            485                 490                 495

Cys Thr Ala Arg Leu Ile Leu Asp Ser Leu Lys Ser Cys Lys Thr Pro
            500                 505                 510

Thr Leu Ile Gly Leu Leu His Val Ile Cys Val Ser Pro Asp Met Gln
            515                 520                 525

Arg Leu Tyr Leu Lys Ala Ala Asp Thr Gln Leu Leu Arg Thr Phe Leu
            530                 535                 540

Phe Lys His Lys Asp Asp Leu Ile Leu Pro Leu Pro Phe Glu Gln Glu
545                 550                 555                 560

Glu Glu Glu Leu Trp Leu Ser Gly Leu Lys Thr Ala Leu Val Leu Thr
            565                 570                 575
```

```
Asp Trp Ala Asp Glu Phe Ser Glu Gly Met Ile Glu Glu Arg Tyr Gly
            580                 585                 590

Ile Gly Ala Gly Asp Leu Tyr Asn Ile Val Asp Ser Gly Lys Trp Leu
        595                 600                 605

Leu His Gly Thr Glu Arg Leu Val Ser Val Glu Met Pro Glu Met Ser
    610                 615                 620

Gln Val Val Lys Thr Leu Ser Val Arg Val His His Gly Val Lys Ser
625                 630                 635                 640

Glu Leu Leu Pro Leu Val Ala Leu Arg Asn Ile Gly Arg Val Arg Ala
                645                 650                 655

Arg Thr Leu Tyr Asn Ala Gly Tyr Pro Asp Pro Glu Ala Val Ala Arg
            660                 665                 670

Ala Gly Leu Ser Thr Ile Ala Arg Ile Ile Gly Glu Gly Ile Ala Arg
        675                 680                 685

Gln Val Ile Asp Glu Ile Thr Gly Val Lys Arg Ser Gly Ile His Ser
    690                 695                 700

Ser Asp Asp Tyr Gln Gln Lys Thr Pro Glu Leu Leu Thr Asp Ile
705                 710                 715                 720

Pro Gly Ile Gly Lys Lys Met Ala Glu Lys Leu Gln Asn Ala Gly Ile
                725                 730                 735

Ile Thr Val Ser Asp Leu Leu Thr Ala Asp Glu Val Leu Leu Ser Asp
            740                 745                 750

Val Leu Gly Ala Ala Arg Ala Arg Lys Val Leu Ala Phe Leu Ser Asn
        755                 760                 765

Ser Glu Lys Glu Asn Ser Ser Asp Lys Thr Glu Glu Ile Pro Asp
    770                 775                 780

Thr Gln Lys Ile Arg Gly Gln Ser Ser Trp Glu Asp Phe Gly Cys
785                 790                 795

<210> SEQ ID NO 22
<211> LENGTH: 1756
<212> TYPE: PRT
<213> ORGANISM: Escherichia coli

<400> SEQUENCE: 22

Met Met Ser Ile Ala Gln Val Arg Ser Ala Gly Ser Ala Gly Asn Tyr
1               5                   10                  15

Tyr Thr Asp Lys Asp Asn Tyr Tyr Val Leu Gly Ser Met Gly Glu Arg
            20                  25                  30

Trp Ala Gly Lys Gly Ala Glu Gln Leu Gly Leu Gln Gly Ser Val Asp
        35                  40                  45

Lys Asp Val Phe Thr Arg Leu Leu Glu Gly Arg Leu Pro Asp Gly Ala
    50                  55                  60

Asp Leu Ser Arg Met Gln Asp Gly Ser Asn Lys His Arg Pro Gly Tyr
65                  70                  75                  80

Asp Leu Thr Phe Ser Ala Pro Lys Ser Val Ser Met Met Ala Met Leu
                85                  90                  95

Gly Gly Asp Lys Arg Leu Ile Asp Ala His Asn Gln Ala Val Asp Phe
            100                 105                 110

Ala Val Arg Gln Val Glu Ala Leu Ala Ser Thr Arg Val Met Thr Asp
        115                 120                 125

Gly Gln Ser Glu Thr Val Leu Thr Gly Asn Leu Val Met Ala Leu Phe
    130                 135                 140

Asn His Asp Thr Ser Arg Asp Gln Glu Pro Gln Leu His Thr His Ala
145                 150                 155                 160
```

Val Val Ala Asn Val Thr Gln His Asn Gly Glu Trp Lys Thr Leu Ser
            165                 170                 175

Ser Asp Lys Val Gly Lys Thr Gly Phe Ile Glu Asn Val Tyr Ala Asn
            180                 185                 190

Gln Ile Ala Phe Gly Arg Leu Tyr Arg Glu Lys Leu Lys Glu Gln Val
            195                 200                 205

Glu Ala Leu Gly Tyr Glu Thr Glu Val Val Gly Lys His Gly Met Trp
            210                 215                 220

Glu Met Pro Gly Val Pro Val Glu Ala Phe Ser Gly Arg Ser Gln Ala
225                 230                 235                 240

Ile Arg Glu Ala Val Gly Glu Asp Ala Ser Leu Lys Ser Arg Asp Val
            245                 250                 255

Ala Ala Leu Asp Thr Arg Lys Ser Lys Gln His Val Asp Pro Glu Ile
            260                 265                 270

Arg Met Ala Glu Trp Met Gln Thr Leu Lys Glu Thr Gly Phe Asp Ile
            275                 280                 285

Arg Ala Tyr Arg Asp Ala Ala Asp Gln Arg Thr Glu Ile Arg Thr Gln
            290                 295                 300

Ala Pro Gly Pro Ala Ser Gln Asp Gly Pro Asp Val Gln Gln Ala Val
305                 310                 315                 320

Thr Gln Ala Ile Ala Gly Leu Ser Glu Arg Lys Val Gln Phe Thr Tyr
            325                 330                 335

Thr Asp Val Leu Ala Arg Thr Val Gly Ile Leu Pro Pro Glu Asn Gly
            340                 345                 350

Val Ile Glu Arg Ala Arg Ala Gly Ile Asp Glu Ala Ile Ser Arg Glu
            355                 360                 365

Gln Leu Ile Pro Leu Asp Arg Glu Lys Gly Leu Phe Thr Ser Gly Ile
            370                 375                 380

His Val Leu Asp Glu Leu Ser Val Arg Ala Leu Ser Arg Asp Ile Met
385                 390                 395                 400

Lys Gln Asn Arg Val Thr Val His Pro Glu Lys Ser Val Pro Arg Thr
            405                 410                 415

Ala Gly Tyr Ser Asp Ala Val Ser Val Leu Ala Gln Asp Arg Pro Ser
            420                 425                 430

Leu Ala Ile Val Ser Gly Gln Gly Gly Ala Ala Gly Gln Arg Glu Arg
            435                 440                 445

Val Ala Glu Leu Val Met Met Ala Arg Glu Gln Gly Arg Glu Val Gln
            450                 455                 460

Ile Ile Ala Ala Asp Arg Arg Ser Gln Met Asn Leu Lys Gln Asp Glu
465                 470                 475                 480

Arg Leu Ser Gly Glu Leu Ile Thr Gly Arg Arg Gln Leu Leu Glu Gly
            485                 490                 495

Met Ala Phe Thr Pro Gly Ser Thr Val Ile Val Asp Gln Gly Glu Lys
            500                 505                 510

Leu Ser Leu Lys Glu Thr Leu Thr Leu Leu Asp Gly Ala Ala Arg His
            515                 520                 525

Asn Val Gln Val Leu Ile Thr Asp Ser Gly Gln Arg Thr Gly Thr Gly
            530                 535                 540

Ser Ala Leu Met Ala Met Lys Asp Ala Gly Val Asn Thr Tyr Arg Trp
545                 550                 555                 560

Gln Gly Gly Glu Gln Arg Pro Ala Thr Ile Ile Ser Glu Pro Asp Arg
            565                 570                 575

```
Asn Val Arg Tyr Ala Arg Leu Ala Gly Asp Phe Ala Ala Ser Val Lys
            580                 585                 590

Ala Gly Glu Glu Ser Val Ala Gln Val Ser Gly Val Arg Glu Gln Ala
        595                 600                 605

Ile Leu Thr Gln Ala Ile Arg Ser Glu Leu Lys Thr Gln Gly Val Leu
    610                 615                 620

Gly His Pro Glu Val Thr Met Thr Ala Leu Ser Pro Val Trp Leu Asp
625                 630                 635                 640

Ser Arg Ser Arg Tyr Leu Arg Asp Met Tyr Arg Pro Gly Met Val Met
                645                 650                 655

Glu Gln Trp Asn Pro Glu Thr Arg Ser His Asp Arg Tyr Val Ile Asp
            660                 665                 670

Arg Val Thr Ala Gln Ser His Ser Leu Thr Leu Arg Asp Ala Gln Gly
        675                 680                 685

Glu Thr Gln Val Val Arg Ile Ser Ser Leu Asp Ser Ser Trp Ser Leu
    690                 695                 700

Phe Arg Pro Glu Lys Met Pro Val Ala Asp Gly Glu Arg Leu Arg Val
705                 710                 715                 720

Thr Gly Lys Ile Pro Gly Leu Arg Val Ser Gly Gly Asp Arg Leu Gln
                725                 730                 735

Val Ala Ser Val Ser Glu Asp Ala Met Thr Val Val Pro Gly Arg
            740                 745                 750

Ala Glu Pro Ala Ser Leu Pro Val Ser Asp Ser Pro Phe Thr Ala Leu
        755                 760                 765

Lys Leu Glu Asn Gly Trp Val Glu Thr Pro His Ser Val Ser Asp
770                 775                 780

Ser Ala Thr Val Phe Ala Ser Val Thr Gln Met Ala Met Asp Asn Ala
785                 790                 795                 800

Thr Leu Asn Gly Leu Ala Arg Ser Gly Arg Asp Val Arg Leu Tyr Ser
                805                 810                 815

Ser Leu Asp Glu Thr Arg Thr Ala Glu Lys Leu Ala Arg His Pro Ser
            820                 825                 830

Phe Thr Val Val Ser Glu Gln Ile Lys Ala Arg Ala Gly Glu Thr Leu
        835                 840                 845

Leu Glu Thr Ala Ile Ser Leu Gln Lys Ala Gly Leu His Thr Pro Ala
850                 855                 860

Gln Gln Ala Ile His Leu Ala Leu Pro Val Leu Glu Ser Lys Asn Leu
865                 870                 875                 880

Ala Phe Ser Met Val Asp Leu Leu Thr Glu Ala Lys Ser Phe Ala Ala
                885                 890                 895

Glu Gly Thr Gly Phe Thr Glu Leu Gly Gly Glu Ile Asn Ala Gln Ile
            900                 905                 910

Lys Arg Gly Asp Leu Leu Tyr Val Asp Val Ala Lys Gly Tyr Gly Thr
        915                 920                 925

Gly Leu Leu Val Ser Arg Ala Ser Tyr Glu Ala Glu Lys Ser Ile Leu
930                 935                 940

Arg His Ile Leu Glu Gly Lys Glu Ala Val Thr Pro Leu Met Glu Arg
945                 950                 955                 960

Val Pro Gly Glu Leu Met Glu Thr Leu Thr Ser Gly Gln Arg Ala Ala
                965                 970                 975

Thr Arg Met Ile Leu Glu Thr Ser Asp Arg Phe Thr Val Val Gln Gly
            980                 985                 990

Tyr Ala Gly Val Gly Lys Thr Thr  Gln Phe Arg Ala Val  Met Ser Ala
```

-continued

```
            995                 1000                1005
Val Asn Met Leu Pro Ala Ser Glu Arg Pro Arg Val Val Gly Leu
        1010                1015                1020
Gly Pro Thr His Arg Ala Val Gly Glu Met Arg Ser Ala Gly Val
        1025                1030                1035
Asp Ala Gln Thr Leu Ala Ser Phe Leu His Asp Thr Gln Leu Gln
        1040                1045                1050
Gln Arg Ser Gly Glu Thr Pro Asp Phe Ser Asn Thr Leu Phe Leu
        1055                1060                1065
Leu Asp Glu Ser Ser Met Val Gly Asn Thr Glu Met Ala Arg Ala
        1070                1075                1080
Tyr Ala Leu Ile Ala Ala Gly Gly Gly Arg Ala Val Ala Ser Gly
        1085                1090                1095
Asp Thr Asp Gln Leu Gln Ala Ile Ala Pro Gly Gln Ser Phe Arg
        1100                1105                1110
Leu Gln Gln Thr Arg Ser Ala Ala Asp Val Val Ile Met Lys Glu
        1115                1120                1125
Ile Val Arg Gln Thr Pro Glu Leu Arg Glu Ala Val Tyr Ser Leu
        1130                1135                1140
Ile Asn Arg Asp Val Glu Arg Ala Leu Ser Gly Leu Glu Ser Val
        1145                1150                1155
Lys Pro Ser Gln Val Pro Arg Leu Glu Gly Ala Trp Ala Pro Glu
        1160                1165                1170
His Ser Val Thr Glu Phe Ser His Ser Gln Glu Ala Lys Leu Ala
        1175                1180                1185
Glu Ala Gln Gln Lys Ala Met Leu Lys Gly Glu Ala Phe Pro Asp
        1190                1195                1200
Ile Pro Met Thr Leu Tyr Glu Ala Ile Val Arg Asp Tyr Thr Gly
        1205                1210                1215
Arg Thr Pro Glu Ala Arg Glu Gln Thr Leu Ile Val Thr His Leu
        1220                1225                1230
Asn Glu Asp Arg Arg Val Leu Asn Ser Met Ile His Asp Ala Arg
        1235                1240                1245
Glu Lys Ala Gly Glu Leu Gly Lys Glu Gln Val Met Val Pro Val
        1250                1255                1260
Leu Asn Thr Ala Asn Ile Arg Asp Gly Glu Leu Arg Arg Leu Ser
        1265                1270                1275
Thr Trp Glu Lys Asn Pro Asp Ala Leu Ala Leu Val Asp Asn Val
        1280                1285                1290
Tyr His Arg Ile Ala Gly Ile Ser Lys Asp Asp Gly Leu Ile Thr
        1295                1300                1305
Leu Gln Asp Ala Glu Gly Asn Thr Arg Leu Ile Ser Pro Arg Glu
        1310                1315                1320
Ala Val Ala Glu Gly Val Thr Leu Tyr Thr Pro Asp Lys Ile Arg
        1325                1330                1335
Val Gly Thr Gly Asp Arg Met Arg Phe Thr Lys Ser Asp Arg Glu
        1340                1345                1350
Arg Gly Tyr Val Ala Asn Ser Val Trp Thr Val Thr Ala Val Ser
        1355                1360                1365
Gly Asp Ser Val Thr Leu Ser Asp Gly Gln Gln Thr Arg Val Ile
        1370                1375                1380
Arg Pro Gly Gln Glu Arg Ala Glu Gln His Ile Asp Leu Ala Tyr
        1385                1390                1395
```

Ala Ile Thr Ala His Gly Ala Gln Gly Ala Ser Glu Thr Phe Ala
    1400                1405                1410

Ile Ala Leu Glu Gly Thr Glu Gly Asn Arg Lys Leu Met Ala Gly
    1415                1420                1425

Phe Glu Ser Ala Tyr Val Ala Leu Ser Arg Met Lys Gln His Val
    1430                1435                1440

Gln Val Tyr Thr Asp Asn Arg Gln Gly Trp Thr Asp Ala Ile Asn
    1445                1450                1455

Asn Ala Val Gln Lys Gly Thr Ala His Asp Val Leu Glu Pro Lys
    1460                1465                1470

Pro Asp Arg Glu Val Met Asn Ala Gln Arg Leu Phe Ser Thr Ala
    1475                1480                1485

Arg Glu Leu Arg Asp Val Ala Ala Gly Arg Ala Val Leu Arg Gln
    1490                1495                1500

Ala Gly Leu Ala Gly Gly Asp Ser Pro Ala Arg Phe Ile Ala Pro
    1505                1510                1515

Gly Arg Lys Tyr Pro Gln Pro Tyr Val Ala Leu Pro Ala Phe Asp
    1520                1525                1530

Arg Asn Gly Lys Ser Ala Gly Ile Trp Leu Asn Pro Leu Thr Thr
    1535                1540                1545

Asp Asp Gly Asn Gly Leu Arg Gly Phe Ser Gly Glu Gly Arg Val
    1550                1555                1560

Lys Gly Ser Gly Asp Ala Gln Phe Val Ala Leu Gln Gly Ser Arg
    1565                1570                1575

Asn Gly Glu Ser Leu Leu Ala Asp Asn Met Gln Asp Gly Val Arg
    1580                1585                1590

Ile Ala Arg Asp Asn Pro Asp Ser Gly Val Val Val Arg Ile Ala
    1595                1600                1605

Gly Glu Gly Arg Pro Trp Asn Pro Gly Ala Ile Thr Gly Gly Arg
    1610                1615                1620

Val Trp Gly Asp Ile Pro Asp Asn Ser Val Gln Pro Gly Ala Gly
    1625                1630                1635

Asn Gly Glu Pro Val Thr Ala Glu Val Leu Ala Gln Arg Gln Ala
    1640                1645                1650

Glu Glu Ala Ile Arg Arg Glu Thr Glu Arg Arg Ala Asp Glu Ile
    1655                1660                1665

Val Arg Lys Met Ala Glu Asn Lys Pro Asp Leu Pro Asp Gly Lys
    1670                1675                1680

Thr Glu Leu Ala Val Arg Asp Ile Ala Gly Gln Glu Arg Asp Arg
    1685                1690                1695

Ser Ala Ile Ser Glu Arg Glu Thr Ala Leu Pro Glu Ser Val Leu
    1700                1705                1710

Arg Glu Ser Gln Arg Glu Glu Ala Val Arg Glu Val Ala Arg
    1715                1720                1725

Glu Asn Leu Leu Gln Glu Arg Leu Gln Gln Met Glu Arg Asp Met
    1730                1735                1740

Val Arg Asp Leu Gln Lys Glu Lys Thr Leu Gly Gly Asp
    1745                1750                1755

<210> SEQ ID NO 23
<211> LENGTH: 726
<212> TYPE: PRT
<213> ORGANISM: Methanococcoides burtonii

<400> SEQUENCE: 23

```
Met Ser Asp Lys Pro Ala Phe Met Lys Tyr Phe Thr Gln Ser Ser Cys
1               5                   10                  15

Tyr Pro Asn Gln Gln Glu Ala Met Asp Arg Ile His Ser Ala Leu Met
            20                  25                  30

Gln Gln Gln Leu Val Leu Phe Glu Gly Ala Cys Gly Thr Gly Lys Thr
        35                  40                  45

Leu Ser Ala Leu Val Pro Ala Leu His Val Gly Lys Met Leu Gly Lys
    50                  55                  60

Thr Val Ile Ile Ala Thr Asn Val His Gln Gln Met Val Gln Phe Ile
65                  70                  75                  80

Asn Glu Ala Arg Asp Ile Lys Lys Val Gln Asp Val Lys Val Ala Val
                85                  90                  95

Ile Lys Gly Lys Thr Ala Met Cys Pro Gln Glu Ala Asp Tyr Glu Glu
            100                 105                 110

Cys Ser Val Lys Arg Glu Asn Thr Phe Glu Leu Met Glu Thr Glu Arg
        115                 120                 125

Glu Ile Tyr Leu Lys Arg Gln Glu Leu Asn Ser Ala Arg Asp Ser Tyr
    130                 135                 140

Lys Lys Ser His Asp Pro Ala Phe Val Thr Leu Arg Asp Glu Leu Ser
145                 150                 155                 160

Lys Glu Ile Asp Ala Val Glu Glu Lys Ala Arg Gly Leu Arg Asp Arg
                165                 170                 175

Ala Cys Asn Asp Leu Tyr Glu Val Leu Arg Ser Asp Ser Glu Lys Phe
            180                 185                 190

Arg Glu Trp Leu Tyr Lys Glu Val Arg Ser Pro Glu Glu Ile Asn Asp
        195                 200                 205

His Ala Ile Lys Asp Gly Met Cys Gly Tyr Glu Leu Val Lys Arg Glu
    210                 215                 220

Leu Lys His Ala Asp Leu Leu Ile Cys Asn Tyr His His Val Leu Asn
225                 230                 235                 240

Pro Asp Ile Phe Ser Thr Val Leu Gly Trp Ile Glu Lys Glu Pro Gln
                245                 250                 255

Glu Thr Ile Val Ile Phe Asp Glu Ala His Asn Leu Glu Ser Ala Ala
            260                 265                 270

Arg Ser His Ser Ser Leu Ser Leu Thr Glu His Ser Ile Glu Lys Ala
        275                 280                 285

Ile Thr Glu Leu Glu Ala Asn Leu Asp Leu Leu Ala Asp Asp Asn Ile
    290                 295                 300

His Asn Leu Phe Asn Ile Phe Leu Glu Val Ile Ser Asp Thr Tyr Asn
305                 310                 315                 320

Ser Arg Phe Lys Phe Gly Glu Arg Glu Val Arg Lys Asn Trp Tyr
                325                 330                 335

Asp Ile Arg Ile Ser Asp Pro Tyr Glu Arg Asn Asp Ile Val Arg Gly
            340                 345                 350

Lys Phe Leu Arg Gln Ala Lys Gly Asp Phe Gly Glu Lys Asp Ile
        355                 360                 365

Gln Ile Leu Leu Ser Glu Ala Ser Glu Leu Gly Ala Lys Leu Asp Glu
    370                 375                 380

Thr Tyr Arg Asp Gln Tyr Lys Lys Gly Leu Ser Ser Val Met Lys Arg
385                 390                 395                 400

Ser His Ile Arg Tyr Val Ala Asp Phe Met Ser Ala Tyr Ile Glu Leu
                405                 410                 415
```

-continued

Ser His Asn Leu Asn Tyr Tyr Pro Ile Leu Asn Val Arg Arg Asp Met
        420                 425                 430

Asn Asp Glu Ile Tyr Gly Arg Val Glu Leu Phe Thr Cys Ile Pro Lys
        435                 440                 445

Asn Val Thr Glu Pro Leu Phe Asn Ser Leu Phe Ser Val Ile Leu Met
450                 455                 460

Ser Ala Thr Leu His Pro Phe Glu Met Val Lys Lys Thr Leu Gly Ile
465                 470                 475                 480

Thr Arg Asp Thr Cys Glu Met Ser Tyr Gly Thr Ser Phe Pro Glu Glu
                485                 490                 495

Lys Arg Leu Ser Ile Ala Val Ser Ile Pro Pro Leu Phe Ala Lys Asn
            500                 505                 510

Arg Asp Asp Arg His Val Thr Glu Leu Leu Glu Gln Val Leu Leu Asp
        515                 520                 525

Ser Ile Glu Asn Ser Lys Gly Asn Val Ile Leu Phe Phe Gln Ser Ala
    530                 535                 540

Phe Glu Ala Lys Arg Tyr Tyr Ser Lys Ile Glu Pro Leu Val Asn Val
545                 550                 555                 560

Pro Val Phe Leu Asp Glu Val Gly Ile Ser Ser Gln Asp Val Arg Glu
                565                 570                 575

Glu Phe Phe Ser Ile Gly Glu Glu Asn Gly Lys Ala Val Leu Leu Ser
            580                 585                 590

Tyr Leu Trp Gly Thr Leu Ser Glu Gly Ile Asp Tyr Arg Asp Gly Arg
        595                 600                 605

Gly Arg Thr Val Ile Ile Gly Val Gly Tyr Pro Ala Leu Asn Asp
    610                 615                 620

Arg Met Asn Ala Val Glu Ser Ala Tyr Asp His Val Phe Gly Tyr Gly
625                 630                 635                 640

Ala Gly Trp Glu Phe Ala Ile Gln Val Pro Thr Ile Arg Lys Ile Arg
                645                 650                 655

Gln Ala Met Gly Arg Val Val Arg Ser Pro Thr Asp Tyr Gly Ala Arg
            660                 665                 670

Ile Leu Leu Asp Gly Arg Phe Leu Thr Asp Ser Lys Lys Arg Phe Gly
        675                 680                 685

Lys Phe Ser Val Phe Glu Val Phe Pro Pro Ala Glu Arg Ser Glu Phe
    690                 695                 700

Val Asp Val Asp Pro Lys Val Lys Tyr Ser Leu Met Asn Phe Phe
705                 710                 715                 720

Met Asp Asn Asp Glu Gln
                725

<210> SEQ ID NO 24
<211> LENGTH: 439
<212> TYPE: PRT
<213> ORGANISM: Enterobacteria phage T4

<400> SEQUENCE: 24

Met Thr Phe Asp Asp Leu Thr Glu Gly Gln Lys Asn Ala Phe Asn Ile
1               5                   10                  15

Val Met Lys Ala Ile Lys Glu Lys Lys His Val Thr Ile Asn Gly
            20                  25                  30

Pro Ala Gly Thr Gly Lys Thr Thr Leu Thr Lys Phe Ile Ile Glu Ala
        35                  40                  45

Leu Ile Ser Thr Gly Glu Thr Gly Ile Ile Leu Ala Ala Pro Thr His

```
                 50                  55                  60
Ala Ala Lys Lys Ile Leu Ser Lys Leu Ser Gly Lys Glu Ala Ser Thr
 65                  70                  75                  80

Ile His Ser Ile Leu Lys Ile Asn Pro Val Thr Tyr Glu Glu Asn Val
                     85                  90                  95

Leu Phe Glu Gln Lys Glu Val Pro Asp Leu Ala Lys Cys Arg Val Leu
                100                 105                 110

Ile Cys Asp Glu Val Ser Met Tyr Asp Arg Lys Leu Phe Lys Ile Leu
                115                 120                 125

Leu Ser Thr Ile Pro Pro Trp Cys Thr Ile Gly Ile Gly Asp Asn
130                 135                 140

Lys Gln Ile Arg Pro Val Asp Pro Gly Glu Asn Thr Ala Tyr Ile Ser
145                 150                 155                 160

Pro Phe Phe Thr His Lys Asp Phe Tyr Gln Cys Glu Leu Thr Glu Val
                165                 170                 175

Lys Arg Ser Asn Ala Pro Ile Ile Asp Val Ala Thr Asp Val Arg Asn
                180                 185                 190

Gly Lys Trp Ile Tyr Asp Lys Val Asp Gly His Gly Val Arg Gly
                195                 200                 205

Phe Thr Gly Asp Thr Ala Leu Arg Asp Phe Met Val Asn Tyr Phe Ser
210                 215                 220

Ile Val Lys Ser Leu Asp Asp Leu Phe Glu Asn Arg Val Met Ala Phe
225                 230                 235                 240

Thr Asn Lys Ser Val Asp Lys Leu Asn Ser Ile Ile Arg Lys Lys Ile
                245                 250                 255

Phe Glu Thr Asp Lys Asp Phe Ile Val Gly Glu Ile Ile Val Met Gln
                260                 265                 270

Glu Pro Leu Phe Lys Thr Tyr Lys Ile Asp Gly Lys Pro Val Ser Glu
                275                 280                 285

Ile Ile Phe Asn Gly Gln Leu Val Arg Ile Ile Glu Ala Glu Tyr
290                 295                 300

Thr Ser Thr Phe Val Lys Ala Arg Gly Val Pro Gly Glu Tyr Leu Ile
305                 310                 315                 320

Arg His Trp Asp Leu Thr Val Glu Thr Tyr Gly Asp Asp Glu Tyr Tyr
                325                 330                 335

Arg Glu Lys Ile Lys Ile Ser Ser Asp Glu Glu Leu Tyr Lys Phe
                340                 345                 350

Asn Leu Phe Leu Gly Lys Thr Ala Glu Thr Tyr Lys Asn Trp Asn Lys
                355                 360                 365

Gly Gly Lys Ala Pro Trp Ser Asp Phe Trp Asp Ala Lys Ser Gln Phe
370                 375                 380

Ser Lys Val Lys Ala Leu Pro Ala Ser Thr Phe His Lys Ala Gln Gly
385                 390                 395                 400

Met Ser Val Asp Arg Ala Phe Ile Tyr Thr Pro Cys Ile His Tyr Ala
                405                 410                 415

Asp Val Glu Leu Ala Gln Gln Leu Leu Tyr Val Gly Val Thr Arg Gly
                420                 425                 430

Arg Tyr Asp Val Phe Tyr Val
                435

<210> SEQ ID NO 25
<211> LENGTH: 970
<212> TYPE: PRT
<213> ORGANISM: Clostridium botulinum
```

<400> SEQUENCE: 25

Met Leu Ser Val Ala Asn Val Arg Ser Pro Ser Ala Ala Ser Tyr
1               5                   10                  15

Phe Ala Ser Asp Asn Tyr Tyr Ala Ser Ala Asp Ala Asp Arg Ser Gly
            20                  25                  30

Gln Trp Ile Gly Asp Gly Ala Lys Arg Leu Gly Leu Glu Gly Lys Val
        35                  40                  45

Glu Ala Arg Ala Phe Asp Ala Leu Leu Arg Gly Glu Leu Pro Asp Gly
    50                  55                  60

Ser Ser Val Gly Asn Pro Gly Gln Ala His Arg Pro Gly Thr Asp Leu
65                  70                  75                  80

Thr Phe Ser Val Pro Lys Ser Trp Ser Leu Leu Ala Leu Val Gly Lys
                85                  90                  95

Asp Glu Arg Ile Ile Ala Ala Tyr Arg Glu Ala Val Val Glu Ala Leu
            100                 105                 110

His Trp Ala Glu Lys Asn Ala Ala Glu Thr Arg Val Val Glu Lys Gly
        115                 120                 125

Met Val Val Thr Gln Ala Thr Gly Asn Leu Ala Ile Gly Leu Phe Gln
    130                 135                 140

His Asp Thr Asn Arg Asn Gln Glu Pro Asn Leu His Phe His Ala Val
145                 150                 155                 160

Ile Ala Asn Val Thr Gln Gly Lys Asp Gly Lys Trp Arg Thr Leu Lys
                165                 170                 175

Asn Asp Arg Leu Trp Gln Leu Asn Thr Thr Leu Asn Ser Ile Ala Met
            180                 185                 190

Ala Arg Phe Arg Val Ala Val Glu Lys Leu Gly Tyr Glu Pro Gly Pro
        195                 200                 205

Val Leu Lys His Gly Asn Phe Glu Ala Arg Gly Ile Ser Arg Glu Gln
    210                 215                 220

Val Met Ala Phe Ser Thr Arg Arg Lys Glu Val Leu Glu Ala Arg Arg
225                 230                 235                 240

Gly Pro Gly Leu Asp Ala Gly Arg Ile Ala Ala Leu Asp Thr Arg Ala
                245                 250                 255

Ser Lys Glu Gly Ile Glu Asp Arg Ala Thr Leu Ser Lys Gln Trp Ser
            260                 265                 270

Glu Ala Ala Gln Ser Ile Gly Leu Asp Leu Lys Pro Leu Val Asp Arg
        275                 280                 285

Ala Arg Thr Lys Ala Leu Gly Gln Gly Met Glu Ala Thr Arg Ile Gly
    290                 295                 300

Ser Leu Val Glu Arg Gly Arg Ala Trp Leu Ser Arg Phe Ala Ala His
305                 310                 315                 320

Val Arg Gly Asp Pro Ala Asp Pro Leu Val Pro Ser Val Leu Lys
                325                 330                 335

Gln Asp Arg Gln Thr Ile Ala Ala Gln Ala Val Ala Ser Ala Val
            340                 345                 350

Arg His Leu Ser Gln Arg Glu Ala Ala Phe Glu Arg Thr Ala Leu Tyr
        355                 360                 365

Lys Ala Ala Leu Asp Phe Gly Leu Pro Thr Thr Ile Ala Asp Val Glu
    370                 375                 380

Lys Arg Thr Arg Ala Leu Val Arg Ser Gly Asp Leu Ile Ala Gly Lys
385                 390                 395                 400

Gly Glu His Lys Gly Trp Leu Ala Ser Arg Asp Ala Val Val Thr Glu

```
                405                 410                 415
Gln Arg Ile Leu Ser Glu Val Ala Ala Gly Lys Gly Asp Ser Ser Pro
            420                 425                 430

Ala Ile Thr Pro Gln Lys Ala Ala Ser Val Gln Ala Ala Ala Leu
            435                 440                 445

Thr Gly Gln Gly Phe Arg Leu Asn Glu Gly Gln Leu Ala Ala Arg
    450                 455                 460

Leu Ile Leu Ile Ser Lys Asp Arg Thr Ile Ala Val Gln Gly Ile Ala
465                 470                 475                 480

Gly Ala Gly Lys Ser Ser Val Leu Lys Pro Val Ala Glu Val Leu Arg
                485                 490                 495

Asp Glu Gly His Pro Val Ile Gly Leu Ala Ile Gln Asn Thr Leu Val
            500                 505                 510

Gln Met Leu Glu Arg Asp Thr Gly Ile Gly Ser Gln Thr Leu Ala Arg
            515                 520                 525

Phe Leu Gly Gly Trp Asn Lys Leu Leu Asp Asp Pro Gly Asn Val Ala
    530                 535                 540

Leu Arg Ala Glu Ala Gln Ala Ser Leu Lys Asp His Val Leu Val Leu
545                 550                 555                 560

Asp Glu Ala Ser Met Val Ser Asn Glu Asp Lys Glu Lys Leu Val Arg
                565                 570                 575

Leu Ala Asn Leu Ala Gly Val His Arg Leu Val Leu Ile Gly Asp Arg
            580                 585                 590

Lys Gln Leu Gly Ala Val Asp Ala Gly Lys Pro Phe Ala Leu Leu Gln
            595                 600                 605

Arg Ala Gly Ile Ala Arg Ala Glu Met Ala Thr Asn Leu Arg Ala Arg
    610                 615                 620

Asp Pro Val Val Arg Glu Ala Gln Ala Ala Gln Ala Gly Asp Val
625                 630                 635                 640

Arg Lys Ala Leu Arg His Leu Lys Ser His Thr Val Glu Ala Arg Gly
                645                 650                 655

Asp Gly Ala Gln Val Ala Ala Glu Thr Trp Leu Ala Leu Asp Lys Glu
            660                 665                 670

Thr Arg Ala Arg Thr Ser Ile Tyr Ala Ser Gly Arg Ala Ile Arg Ser
            675                 680                 685

Ala Val Asn Ala Ala Val Gln Gln Gly Leu Leu Ala Ser Arg Glu Ile
    690                 695                 700

Gly Pro Ala Lys Met Lys Leu Glu Val Leu Asp Arg Val Asn Thr Thr
705                 710                 715                 720

Arg Glu Glu Leu Arg His Leu Pro Ala Tyr Arg Ala Gly Arg Val Leu
                725                 730                 735

Glu Val Ser Arg Lys Gln Ala Leu Gly Leu Phe Ile Gly Glu Tyr
            740                 745                 750

Arg Val Ile Gly Gln Asp Arg Lys Gly Lys Leu Val Glu Val Glu Asp
            755                 760                 765

Lys Arg Gly Lys Arg Phe Arg Phe Asp Pro Ala Arg Ile Arg Ala Gly
    770                 775                 780

Lys Gly Asp Asp Asn Leu Thr Leu Leu Glu Pro Arg Lys Leu Glu Ile
785                 790                 795                 800

His Glu Gly Asp Arg Ile Arg Trp Thr Arg Asn Asp His Arg Arg Gly
                805                 810                 815

Leu Phe Asn Ala Asp Gln Ala Arg Val Val Glu Ile Ala Asn Gly Lys
            820                 825                 830
```

```
Val Thr Phe Glu Thr Ser Lys Gly Asp Leu Val Glu Leu Lys Lys Asp
        835             840                 845
Asp Pro Met Leu Lys Arg Ile Asp Leu Ala Tyr Ala Leu Asn Val His
    850                 855                 860
Met Ala Gln Gly Leu Thr Ser Asp Arg Gly Ile Ala Val Met Asp Ser
865                 870                 875                 880
Arg Glu Arg Asn Leu Ser Asn Gln Lys Thr Phe Leu Val Thr Val Thr
                885                 890                 895
Arg Leu Arg Asp His Leu Thr Leu Val Val Asp Ser Ala Asp Lys Leu
                900                 905                 910
Gly Ala Ala Val Ala Arg Asn Lys Gly Glu Lys Ala Ser Ala Ile Glu
            915                 920                 925
Val Thr Gly Ser Val Lys Pro Thr Ala Thr Lys Gly Ser Gly Val Asp
    930                 935                 940
Gln Pro Lys Ser Val Glu Ala Asn Lys Ala Glu Lys Glu Leu Thr Arg
945                 950                 955                 960
Ser Lys Ser Lys Thr Leu Asp Phe Gly Ile
                965                 970
```